United States Patent
Shaheen et al.

(10) Patent No.: US 9,365,846 B2
(45) Date of Patent: Jun. 14, 2016

(54) SURFACE, ANCHORED FC-BAIT ANTIBODY DISPLAY SYSTEM

(75) Inventors: Hussam Hisham Shaheen, Lebanon, NH (US); Dongxing Zha, Etna, NH (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 348 days.

(21) Appl. No.: 13/990,941

(22) PCT Filed: Nov. 29, 2011

(86) PCT No.: PCT/US2011/062286
§ 371 (c)(1),
(2), (4) Date: Aug. 6, 2013

(87) PCT Pub. No.: WO2012/074948
PCT Pub. Date: Jun. 7, 2012

(65) Prior Publication Data
US 2014/0186334 A1    Jul. 3, 2014

Related U.S. Application Data

(60) Provisional application No. 61/458,771, filed on Dec. 1, 2010.

(51) Int. Cl.
*C40B 40/10* (2006.01)
*C12N 15/10* (2006.01)
*C07K 16/00* (2006.01)
*C07K 16/32* (2006.01)
(Continued)

(52) U.S. Cl.
CPC ............ *C12N 15/1037* (2013.01); *C07K 16/00* (2013.01); *C07K 16/32* (2013.01); *C07K 16/40* (2013.01); *C07K 16/46* (2013.01); *C07K 2317/14* (2013.01); *C07K 2317/21* (2013.01); *C07K 2317/35* (2013.01); *C07K 2317/41* (2013.01); *C07K 2317/52* (2013.01); *C40B 40/10* (2013.01)

(58) Field of Classification Search
None
See application file for complete search history.

(56) References Cited

U.S. PATENT DOCUMENTS

2007/0105199 A1    5/2007    Yan et al.
2009/0163379 A1    6/2009    Wang et al.
(Continued)

FOREIGN PATENT DOCUMENTS

EP    1743938    1/2007
WO    WO2008100816    8/2008
(Continued)

OTHER PUBLICATIONS

Shaheen et al., A dual-mode surface display system for the maturation and production of monoclonal antibodies in glyco-engineered Pichia Pastoris., PLOS ONE, 2013, 1-10, 8-7, US.

*Primary Examiner* — Christian Boesen

(57) ABSTRACT

The present invention provides, in part, an antibody display system that simultaneously uses a secretion and a display mode. A bait complexed with a monovalent antibody fragment can be expressed on the surface of the host cell wherein the fragment may be assayed for antigen binding while full antibody is simultaneously secreted from the host cell. Methods of using the system for identifying antibodies that bind specifically to an antigen of interest are also provided. Polypeptides, polynucleotides and host cells useful for making the antibody display system are also provided along with methods of use thereof.

40 Claims, 13 Drawing Sheets

(51) Int. Cl.
*C07K 16/40* (2006.01)
*C07K 16/46* (2006.01)

(56) References Cited

U.S. PATENT DOCUMENTS

2010/0009866 A1  1/2010  Prinz et al.

2010/0075326 A1  3/2010  Jin et al.
2010/0331192 A1  12/2010  Zha et al.

FOREIGN PATENT DOCUMENTS

WO  WO 2009/111183 A1 *  9/2009  ........... G01N 33/567
WO  WO2009111183  9/2009
WO  WO2011100566  8/2011

* cited by examiner

BP550-Fc-Sed1p

| | | AX189 Ctrl | Presorted Library | | | | | | Round 2 100nM (S2) Sorted Library | | | |
|---|---|---|---|---|---|---|---|---|---|---|---|---|
| | SID | μg/mL | 2 | 3 | 4 | 5 | 6 | 7 | 8 | 9 | 10 | 11 | 12 |
| Kappa ELISA | A | 250 | 5.2 | 4.3 | 3.9 | 1.5 | 1.9 | 4.8 | 0.4 | 4.1 | 3.1 | 3.2 | 2.4 |
| | B | 83 | 4.0 | 2.1 | 5.9 | 4.5 | 4.7 | 6.8 | 2.3 | 2.5 | 3.6 | 3.8 | 3.8 |
| | C | 27.8 | 4.1 | 2.5 | 4.4 | 6.6 | 3.9 | 6.4 | 7.2 | 3.2 | 2.7 | 2.9 | 3.0 |
| | D | 9.3 | 3.5 | 6.1 | 3.9 | 1.6 | 0.5 | 4.0 | 3.4 | 3.2 | 4.3 | 1.0 | 2.2 |
| | E | 3.1 | 4.1 | 3.8 | 7.5 | 3.4 | 8.4 | 6.2 | 3.3 | 0.4 | 1.5 | 2.9 | 3.0 |
| | F | 1.0 | 3.5 | 5.3 | 6.8 | 1.8 | 4.0 | 4.1 | 3.1 | 2.7 | 3.7 | 4.3 | 0.4 |
| | G | 0.3 | 2.9 | 4.8 | 5.0 | 2.7 | 3.4 | 2.2 | 2.6 | 4.4 | 5.5 | 6.6 | 3.2 |
| | H | 0.1 | 2.2 | 2.6 | 2.5 | 1.5 | 4.4 | 3.8 | 2.1 | 1.9 | 4.1 | 2.3 | 2.4 |

| | SID | μg/mL | 2 | 3 | 4 | 5 | 6 | 7 | 8 | 9 | 10 | 11 | 12 |
|---|---|---|---|---|---|---|---|---|---|---|---|---|---|
| PCSK9 ELISA | A | 100 | 59.8 | 0.4 | 0.3 | 0.1 | 0.0 | 0.8 | 1.7 | >Max | 267.9 | 243.5 | 34.0 |
| | B | 33 | 147.8 | <Min | 0.3 | <Min | 0.4 | 0.3 | 86.4 | 67.7 | 217.6 | >Max | 49.6 |
| | C | 11.1 | 111.1 | 0.0 | 1.0 | <Min | 0.1 | 2.8 | 309.4 | 74.3 | 252.8 | 797.7 | 32.8 |
| | D | 3.7 | 120.8 | 0.0 | <Min | <Min | <Min | 0.5 | 22.9 | 120.1 | 80.3 | 7.2 | 45.8 |
| | E | 1.2 | 128.3 | 0.1 | 0.2 | <Min | <Min | 0.2 | 53.6 | 0.9 | 26.7 | 181.8 | 231.0 |
| | F | 0.4 | 1370.7 | 22.6 | <Min | <Min | 0.0 | <Min | 55.7 | 85.3 | 87.7 | 371.3 | 0.6 |
| | G | 0.1 | 135.2 | <Min | <Min | <Min | <Min | 1.6 | 105.6 | 463.6 | 195.6 | 585.5 | 118.6 |
| | H | 0.0 | 3353.4 | <Min | <Min | <Min | 0.6 | <Min | 53.6 | 204.8 | 590.3 | 111.7 | 58.1 |

FIG.7a

BP551-Fc-Sed1p

| | | AX189 Ctrl | Presorted Library | | | | | Round 2 100nM (S2) Sorted Library | | | | |
|---|---|---|---|---|---|---|---|---|---|---|---|---|
| | SID | µg/mL | 2 | 3 | 4 | 5 | 6 | 7 | 8 | 9 | 10 | 11 | 12 |
| Kappa ELISA | A | 250 | 5.0 | 5.4 | 0.9 | 2.3 | 0.3 | 1.4 | 5.9 | 3.6 | 4.3 | 5.0 | 4.9 |
| | B | 83 | 5.1 | 2.4 | 0.1 | 2.9 | 2.0 | 4.5 | 3.2 | 2.9 | 7.9 | 5.9 | 2.8 |
| | C | 27.8 | 4.0 | 4.9 | 1.9 | 3.7 | 3.6 | 3.9 | 3.5 | 0.2 | 0.1 | 8.6 | 0.1 |
| | D | 9.3 | 3.7 | 5.5 | 3.3 | 1.9 | 3.7 | 0.1 | 7.2 | 7.4 | 0.1 | 5.4 | 0.1 |
| | E | 3.1 | 5.0 | 0.3 | 0.2 | 3.0 | 3.8 | 2.8 | 2.9 | 3.9 | 4.8 | 4.4 | 3.5 |
| | F | 1.0 | 2.7 | 0.1 | 3.2 | 3.8 | 3.5 | 3.9 | 6.4 | 2.8 | 4.7 | 6.3 | 4.3 |
| | G | 0.3 | 2.8 | 0.1 | 1.9 | 2.1 | 2.0 | 3.4 | 3.9 | 3.0 | 2.6 | 2.7 | 3.5 |
| | H | 0.1 | 2.2 | 1.9 | 0.3 | 1.4 | 1.5 | 1.5 | 2.4 | 1.7 | 4.5 | 3.9 | 3.9 |

| | SID | µg/mL | 2 | 3 | 4 | 5 | 6 | 7 | 8 | 9 | 10 | 11 | 12 |
|---|---|---|---|---|---|---|---|---|---|---|---|---|---|
| PCSK9 ELISA | A | 100 | 73.3 | 15.4 | 0.5 | 0.0 | 0.2 | 0.3 | 281.9 | 170.6 | 58.2 | 49.9 | 55.3 |
| | B | 33 | 202.0 | 0.4 | 0.1 | 0.1 | 0.3 | 0.4 | 210.7 | 147.9 | 720.9 | 228.1 | 32.7 |
| | C | 11.1 | 102.6 | 0.5 | 1.3 | 8.1 | 0.0 | 1.6 | 42.9 | 167.5 | 83.7 | 855.9 | 138.5 |
| | D | 3.7 | 143.5 | 0.0 | <Min | 0.1 | 0.0 | 0.1 | 97.3 | >Max | 592.4 | 67.2 | 115.6 |
| | E | 1.2 | 207.1 | 0.1 | 0.2 | 0.0 | 0.6 | 0.2 | 14.1 | 249.2 | 252.6 | 190.0 | 270.1 |
| | F | 0.4 | 173.0 | 0.0 | <Min | <Min | 9.3 | 9.5 | 132.3 | 32.5 | 43.3 | 286.8 | 87.0 |
| | G | 0.1 | 93.3 | 0.2 | 0.1 | 0.1 | 0.2 | 0.9 | 296.2 | 108.8 | 33.6 | 48.6 | 181.1 |
| | H | 0.0 | 95.4 | <Min | <Min | <Min | 0.1 | <Min | 125.6 | 42.8 | 172.3 | 150.6 | 70.5 |

SURFACE, ANCHORED FC-BAIT ANTIBODY DISPLAY SYSTEM

The present application claims the benefit of U.S. provisional patent application No. 61/458,771, filed Dec. 1, 2011, which is herein incorporated by reference in its entirety.

FIELD OF THE INVENTION

The field of the invention relates to antibody display systems and methods of use for identifying antibodies that bind specifically to an antigen.

BACKGROUND OF THE INVENTION

A technique for constructing and screening antibody libraries is phage display, whereby the protein of interest is expressed as a polypeptide fusion to a bacteriophage coat protein and subsequently screened by binding to immobilized or soluble biotinylated ligand.

Phage display, however, has several shortcomings. For example, some eukaryotic secreted proteins and cell surface proteins require post-translational modifications such as glycosylation or extensive disulfide isomerization, which are unavailable in bacterial cells.

Current yeast surface antibody display systems, such as cold capture, also suffer from various drawbacks. In the cold capture antibody display system, at low temperatures, the process of antibody release from host cell transport vesicles is delayed, so that the secreted antibody can be assayed on the cell surface for antigen binding. The cold capture method suffers from a low signal-to-noise ratio and identification of an antibody with specificity for the target antigen depends heavily on cellular expression levels of the antibody.

The affinity matrix system couples antibodies to the host cell surface, e.g., by biotin, where they can be assayed for antigen binding. The affinity matrix system exhibits a high incidence of cross-contamination between antibody clones. Antibodies may become decoupled from the host cell and, thus lose their link to the polynucleotides encoding their immunoglobulin chains.

Full length antibody display systems tether the full length antibody on the host cell surface by binding an immunoglobulin binding protein, such as protein A, that is fused to a cell surface anchor protein. The host cell contains polynucleotides encoding the antibody immunoglobulin chains. Typically, binding of the antibody occurs after the immunoglobulin binding protein is expressed on the cell surface. This system, thus, leads to some erroneous binding of the antibody to host cells that do not express the antibody.

SUMMARY OF THE INVENTION

The present invention provides, in part, an antibody display system that does not suffer from shortcomings of currently available systems. The present invention also allows coupling of antibody display to production strain selection. The strain discovered by surface display screening can be turned into the production strain while preserving the antibody sequence and integrity. This method enables screening for parameters such as antibody folding and expression.

The present invention provides an antibody display system comprising: (a) an isolated eukaryotic host cell (e.g., a *Pichia* cell such as *Pichia pastoris*); (b) a bait comprising a Fc immunoglobulin domain or functional fragment thereof (e.g., comprising a CH3, CH2-CH3 or VH—CH1 polypeptide) (e.g., human) fused to a surface anchor polypeptide or functional fragment thereof (e.g., wherein the cell comprises a polynucleotide encoding the bait); (c) one or more polynucleotides encoding an immunoglobulin light chain variable region; and (d) one or more polynucleotides encoding an immunoglobulin heavy chain variable region. Optionally, the antibody display system further comprises a non-tethered full antibody comprising said immunoglobulin light and heavy chains; and/or monovalent antibody fragment which is complexed with the Fc moiety of the bait. In an embodiment of the invention, said one or more polynucleotides encoding an immunoglobulin light chain variable region is from a genetically diverse population of immunoglobulin light chain variable regions (e.g., an immunoglobulin library); and/or, wherein said one or more polynucleotides encoding an immunoglobulin heavy chain variable region is from a genetically diverse population of immunoglobulin heavy chain variable regions (e.g., an immunoglobulin library). In an embodiment of the invention, the host cell comprises a polynucleotide encoding the bait which is operably associated with a regulatable promoter (e.g., a GUT1 promoter, a GADPH promoter or a PCK1 promoter).

The present invention also provides an isolated bait polypeptide, e.g., comprising an Fc immunoglobulin domain or functional fragment thereof (e.g., wherein the Fc is derived from an IgG1, IgG2, IgG3 or IgG4 immunoglobulin; e.g., human, e.g., comprising a VH—CH1, a CH2-CH3 or a CH3 polypeptide) fused to a surface anchor polypeptide (e.g., SED1) or functional fragment thereof. Any isolated polynucleotide encoding such a polypeptide; vectors including the polynucleotides and isolated host cells comprising the polynucleotides and vectors form part of the present invention. The scope of the present invention includes an isolated host cell (e.g., a eukaryotic host cell such as *Pichia*, e.g., *Pichia pastoris*) further comprising one or more polynucleotides encoding an immunoglobulin light chain variable region (e.g., from a library); and/or one or more polynucleotides encoding an immunoglobulin heavy chain variable region (e.g., from a library). In an embodiment of the invention, a host cell of the present invention includes the polypeptide located on the surface of the cell, e.g., on the cell membrane.

The present invention comprises an isolated host cell (e.g., *Pichia* such as *Pichia pastoris*) comprising a bait polypeptide complexed with an Fc/antigen-binding fragment, e.g., located at the host cell surface by a cell surface anchor (such as SED1) that is part of the bait; optionally wherein the Fc/antigen-binding fragment is bound to an antigen; optionally comprising an antibody or antigen-binding fragment thereof that comprises the light and heavy chain immunoglobulins of the Fc/antigen-binding fragment; for example, wherein the host cell comprises one or more polynucleotides encoding e.g., the bait, the light chain immunoglobulin and/or the heavy chain immunoglobulin.

The present invention also provides a composition comprising the host cell of the present invention (see e.g., above), further comprising a non-tethered full antibody comprising said immunoglobulin light and heavy chains; and/or an Fc/antigen-binding fragment of an antibody (e.g., a monovalent antibody fragment) which is complexed with the Fc moiety of the bait. In an embodiment of the invention, said full antibody or Fc/antigen-binding fragment is complexed with an antigen.

The present invention provides a method for determining if an antibody or antigen-binding fragment thereof specifically binds to an antigen comprising contacting an antibody display system with said antigen; wherein the antibody display system comprises: (a) an isolated eukaryotic host cell (e.g.,

*Pichia* such as *Pichia pastoris*) comprising a polynucleotide encoding an immunoglobulin light chain (e.g., from a library); and a polynucleotide encoding an immunoglobulin heavy chain (e.g., from a library); and (b) a bait comprising an Fc immunoglobulin domain or functional fragment thereof (e.g., human, e.g., comprising a VH—CH1, CH2-CH3 or CH3 polypeptide) fused to a surface anchor polypeptide or functional fragment thereof (e.g., SED1) on the surface of said eukaryotic host cell; wherein the Fc of said bait complexes with an Fc/antigen-binding fragment (e.g., a monovalent antibody fragment) comprising said immunoglobulin heavy and immunoglobulin light chains on the surface of the host cell; and determining if said Fc/antigen-binding fragment (e.g., monovalent antibody fragment) specifically binds to said antigen; wherein the antibody is determined to specifically bind said antigen if the monovalent antibody fragment specifically binds to said antigen. In an embodiment of the invention, the method further comprises isolating the polynucleotide(s) and, optionally, determining the nucleotide sequence. In an embodiment of the invention, the method further comprises inhibiting expression of said bait, then determining the affinity of said identified antibody or antigen-binding fragment thereof for said antigen. In an embodiment of the invention, the method further comprises recombinantly expressing the immunoglobulin chains encoded by the polynucleotides and, optionally, isolating an antibody or antigen-binding fragment thereof comprising said immunoglobulins and, optionally, producing a pharmaceutical formulation comprising combining said antibody or antigen-binding fragment thereof and a pharmaceutically acceptable carrier.

The present invention also provides a method for identifying: (i) an antibody or antigen-binding fragment thereof that binds specifically to an antigen; or (ii) a polynucleotide encoding an immunoglobulin heavy chain of said antibody or fragment (e.g., from a library) and/or a polynucleotide encoding an immunoglobulin light chain of said antibody or fragment (e.g., from a library); comprising contacting an antibody display system with said antigen wherein the antibody display system comprises: (a) an isolated eukaryotic host cell (e.g., *Pichia* such as *Pichia pastoris*) comprising a polynucleotide encoding an immunoglobulin light chain; and a polynucleotide encoding an immunoglobulin heavy chain; and (b) a bait comprising an Fc immunoglobulin domain or functional fragment thereof (e.g., human; e.g., comprising a VH—CH1, CH2-CH3 or CH3 polypeptide) fused to a surface anchor polypeptide or functional fragment thereof (e.g., SED1) on the surface of said eukaryotic host cell; wherein the Fc of said bait complexes with an Fc/antigen-binding fragment (e.g., a monovalent antibody fragment) comprising said immunoglobulin heavy and immunoglobulin light chains on the surface of the host cell; and determining if said Fc/antigen-binding fragment (e.g., monovalent antibody fragment) specifically binds to said antigen; wherein the antibody or fragment or polynucleotide is identified if said specific binding to said antigen is observed. In an embodiment of the invention, the method further comprises isolating the polynucleotide(s) and, optionally, determining the nucleotide sequence. In an embodiment of the invention, the method further comprises inhibiting expression of said bait, then determining the affinity of said identified antibody or antigen-binding fragment thereof for said antigen. In an embodiment of the invention, the method further comprises recombinantly expressing the immunoglobulin chains encoded by the polynucleotides and, optionally, isolating an antibody or antigen-binding fragment thereof comprising said immunoglobulins and, optionally, producing a pharmaceutical formulation comprising combining said antibody or antigen-binding fragment thereof and a pharmaceutically acceptable carrier.

The present invention also provides a method for making an antibody display system comprising: (a) an isolated eukaryotic host cell (e.g., *Pichia* such as *Pichia pastoris*); (b) a bait comprising a human Fc immunoglobulin domain or functional fragment thereof (e.g., human; e.g., comprising a VH—CH1, CH2-CH3 or CH3 polypeptide) fused to a surface anchor polypeptide or functional fragment thereof (e.g., SED1); (c) one or more polynucleotides encoding an immunoglobulin light chain variable region (e.g., from a library); (d) one or more polynucleotides encoding an immunoglobulin heavy chain variable region (e.g., from a library); comprising introducing, into said eukaryotic host cell, a polynucleotide encoding said bait, said one or more polynucleotides encoding an immunoglobulin light chain variable region; and said one or more polynucleotides encoding an immunoglobulin heavy chain variable region.

The present invention also provides a method for making an antibody or antigen-binding fragment thereof comprising introducing, into an isolated eukaryotic host cell (e.g., *Pichia* such as *Pichia pastoris*) comprising a bait that includes a human Fc immunoglobulin domain or functional fragment thereof (e.g., human; e.g., comprising a VH—CH1, CH2-CH3 or CH3 polypeptide) fused to a surface anchor polypeptide or functional fragment thereof (e.g., SED1), one or more polynucleotides encoding an immunoglobulin light chain variable region; and/or one or more polynucleotides encoding an immunoglobulin heavy chain variable region; and culturing the host cell under condition whereby the polynucleotides encoding the immunoglobulin chains are expressed and an antibody or antigen-binding fragment thereof is formed from said chains; wherein said bait is operably associated with a regulatable promoter (e.g., a GUT1 promoter, a GADPH promoter or a PCK1 promoter) and bait expression is inhibited when said immunoglobulin chains are expressed.

The present invention further comprises a method for making an antibody or antigen binding fragment thereof comprising culturing an isolated eukaryotic host cell (e.g., *Pichia pastoris*) in a growth medium under conditions allowing expression of an immunoglobulin light chain and an immunoglobulin heavy chain of said antibody or fragment; wherein the eukaryotic host cell comprises: (i) a polynucleotide encoding said immunoglobulin light chain; and a polynucleotide encoding said immunoglobulin heavy chain of said antibody or fragment (e.g., wherein said chains are encoded by one common polynucleotide or two separate polynucleotides; and/or, wherein said one or both of said polynucleotides were obtained from a library or from a single clonal source); and (ii) a bait comprising an Fc immunoglobulin domain or functional fragment thereof (e.g., human; e.g., comprising a VH—CH1, CH2-CH3 or CH3 polypeptide) fused to a surface anchor polypeptide or functional fragment thereof on the surface of said eukaryotic host cell; wherein the Fc of said bait complexes with an Fc/antigen-binding fragment (e.g., an monovalent antibody fragment) comprising said immunoglobulin heavy and immunoglobulin light chains on the surface of the host cell; and wherein the expression of the bait is optionally inhibited; wherein said antibody or fragment is optionally secreted from said eukaryotic host cell; optionally comprising isolating said antibody or fragment from said eukaryotic host cell and medium.

The present invention further provides a method for determining the effect of a sugar (e.g., an O-glycan and/or an N-glycan, e.g., any of those discussed herein) on an antibody or antigen-binding fragment thereof which specifically binds to an antigen comprising contacting an antibody display system with said antigen; wherein the antibody display system comprises: (a) an isolated eukaryotic controlled glycosylation host cell (e.g., *Pichia pastoris*) comprising a polynucleotide encoding an immunoglobulin light chain; and a polynucleotide encoding an immunoglobulin heavy chain; and (b) a bait comprising an Fc immunoglobulin domain or functional fragment thereof (e.g., human; e.g., comprising a VH—CH1, CH2-CH3 or CH3 polypeptide) comprising said sugar fused to a surface anchor polypeptide or functional fragment thereof on the surface of said host cell;
wherein the Fc of said bait complexes with the Fc/antigen-binding fragment comprising said immunoglobulin heavy and immunoglobulin light chains on the surface of the host cell; wherein said heavy and/or light chain comprises said sugar;
determining if said Fc/antigen-binding fragment specifically binds to said antigen; determining the binding affinity of the antibody or antigen-binding fragment thereof comprising said sugar for the antigen; and comparing the affinity of the antibody or antigen-binding fragment thereof for the antigen with affinity for the antigen of an otherwise identical antibody or antigen-binding fragment thereof which lacks said sugar; wherein the sugar is determined to increase affinity for the antigen if the affinity of the antibody or antigen-binding fragment thereof comprising said sugar is higher than the affinity of the antibody or antigen-binding fragment thereof which lacks the sugar, and/or wherein the sugar is determined to decrease affinity for the antigen if the affinity of antibody or antigen-binding fragment thereof comprising said sugar is lower than the affinity of the antibody or antigen-binding fragment thereof which lacks the sugar.

BRIEF DESCRIPTION OF THE FIGURES

FIG. 7. PCSK9 and Kappa ELISA analysis of presorted BP550 and BP551 library and round 2 sorted pools thereof.

DETAILED DESCRIPTION OF THE INVENTION

Figure 1:
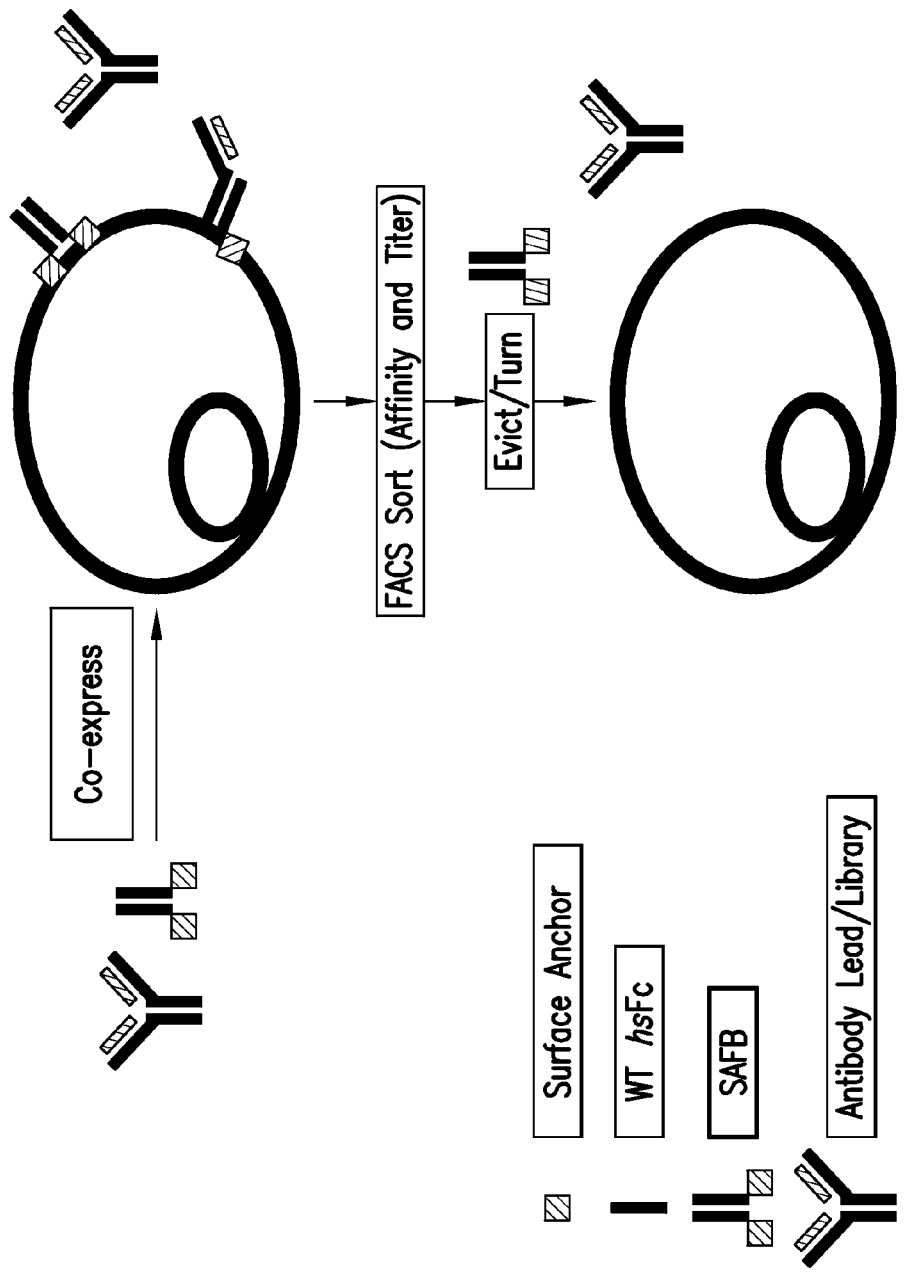
FIG. 1. Antibody display system of the present invention and a method of use thereof. Polynucleotide encoding an antibody and bait are co-expressed in *Pichia pastoris*. The polynucleotide encoding one or both of the antibody immunoglobulin chains can be from a library or can be from a single clonal source. The *Pichia* cell expresses the bait on the cell surface, some of such baits are bound by a monovalent antibody fragment (comprising one heavy and one light chain) of the antibody that is also expressed. Some expressed antibody escapes bait binding and is, thus, soluble. Expression of the antibody on the cell can be confirmed by FAVS analysis and a titer of the cellular antibody expression level can also be determined. The bait expression is turned off or the polynucleotide encoding the bait is evicted (or knocked-out) from the cell. The resulting cell expresses only the polynucleotide encoding the antibody heavy and light chains and produces only full soluble antibody. Cellular expression levels of the antibody can then be confirmed and a determination of the antibody affinity can also be performed.

The present invention provides a method and system for antibody surface display that simultaneously features a display mode and full antibody secretion mode. Host cells secrete full antibody and display Fc/antigen-binding fragments on the cell surface. This method utilizes an Fc fusion (e.g., fused at the N- or C-terminus) with a cell surface protein as "bait" that is covalently coupled to the cell surface (e.g., the cell wall) or embedded (partially or fully) in the cell membrane (e.g., as a transmembrane protein) and that is co-expressed with an antibody (e.g., a single specific antibody from a clonal source or an antibody from a library). In the endoplasmic reticulum, where antibody molecules normally dimerize to form the full antibody molecule, a surface anchored Fc fusion "bait" heterodimerizes with a monovalent antibody fragment creating a complex that is displayed on the cell surface. Monovalent antibody fragments on the cell surface can bind antigen.

The antibody system of the present invention can be employed in any host cell (e.g., yeast, mammalian cells, bacteria) wherein a bait can be expressed on the host cell surface and an Fc/antigen-binding fragment can bind to the bait.

Homodimerization of full antibody still occurs allowing secretion of full antibody molecules into the culture supernatant. The secreted full antibody can be used, e.g., for preclinical studies, e.g., after isolation.

If desired, bait can be knocked-out or mutated or its expression can be turned off to create a strain producing only the full antibody.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Barnes & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A library is, typically, a collection of related but diverse polynucleotides that are, in general, in a common vector backbone. For example, a light chain or heavy chain immunoglobulin library may contain polynucleotides, in a common vector backbone, that encode light and/or heavy chain immunoglobulins which are diverse but related in their nucleotide sequence; for example, which immunoglobulins are functionally diverse in their abilities to form complexes with other immunoglobulins, e.g., in an antibody display system of the present invention, and bind a particular antigen.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be spliced (if it contains introns) and translated into a protein encoded by the coding sequence. Thus, a bait gene can be operably associated with a promoter, such as a regulatable promoter or a constitutive promoter.

Polynucleotides discussed herein form part of the present invention. A "polynucleotide", "nucleic acid" or "nucleic acid molecule" include DNA and RNA, single or double stranded.

Polynucleotides e.g., encoding an immunoglobulin chain or component of the antibody display system of the present invention (e.g., a bait), may, in an embodiment of the invention, be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, and 3'-non-coding regions, and the like.

Polynucleotides e.g., encoding an immunoglobulin chain or component of the antibody display system of the present invention, may be operably associated with a promoter. A "promoter" or "promoter sequence" is, in an embodiment of the invention, a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, at al., (1981) Nature 290:304-310), the promoter contained in the 3' long terminal repeat of Rous sarcoma virus (Yamamoto, at al., (1980) Cell 22:787-797), the herpes thymidine kinase promoter (Wagner, at al., (1981) Proc. Natl. Acad. Sci. USA 78:1441-1445), the regulatory sequences of the metallothionein gene (Brinster, at al., (1982) Nature 296:39-42); prokaryotic expression vectors such as the β-lactamase promoter (ViIla-Komaroff, et al., (1978) Proc. Natl. Acad. Sci. USA 75:3727-3731), or the tac promoter (DeBoer, at al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

The terms "vector", "cloning vector" and "expression vector" include a vehicle (e.g., a plasmid) by which a DNA or RNA sequence can be introduced into a host cell, so as to transform the host and, optionally, promote expression and/or replication of the introduced sequence. Polynucleotides encoding an immunoglobulin chain or component of the antibody display system of the present invention (e.g., a bait) may, in an embodiment of the invention, be in a vector.

A host cell that may be used in a composition or method of the present invention, as is discussed herein, includes eukaryotes such a lower and higher eukaryotic cells as well as prokaryotics. Higher eukaryote cells include mammalian, insect (e.g., *Spodoptera frugiperda* cells), and plant cells (e.g., Protalix cells). In an embodiment of the invention, the host cell is a lower eukaryote such as a yeast or filamentous fungi cell, which, for example, is selected from the group consisting of any *Pichia cell, Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia, Saccharomyces cerevisiae, Saccharomyces, Hanspnula polymorpha, Kluyveromyces, Kluyveromyces lactis, Candida albicans, Aspergillus nidulans, Aspergillus niger, Aspergillus oryzae, Trichoderma reesei, Chrysosporium lucknowense, Fusarium, Fusatum gramineum, Fusarium venenatum* and *Neuraspora crassa*. A higher eukaryotic host cell includes a mammalian host cell for example a Chinese hamster ovary (CHO) cell, a BHK cell, or an NSO cell. A prokaryotic host cell can be, for example, a bacterial cell such as *Escherichia, Enterobacter, Azotobacter, Erwinia, Bacillus, Pseudomonas, Klebsiella, Proteus, Salmonella, Serratia, Shigella, Rhizobia, Vitreoscilla*, and *Paracoccus. E. coli* host cells include DHB4, BL21 (which are deficient in both Lon (Phillips et al. (1984) J. Bacteriol. 159:

283) and OmpT proteases), HB101, BL21 DE3, *E. coli* AD494, *E. coli* W3110 (ATCC 27,325), *E. coli* 294 (ATCC 31,446), *E. coli*. B, and *E. coli* X1776 (ATCC 31,537). Other strains include *E. coli* B834 which are methionine deficient (Leahy et al. (1992) Science 258, 987); other strains include the BLR strain, and the K-12 strains HMS174 and NovaBlue, which are recA-derivative that improve plasmid monomer yields and may help stabilize target plasmids containing repetitive sequences (these strains can be obtained from Novagen). See also U.S. Pat. Nos. 4,952,496, 5,693,489 and 5,869,320 and in Davanloo, P., et al., (1984) Proc. Natl. Acad. Sci. USA 81, 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259. Prokaryotic cells can also be cultured, for example, in a medium under conditions allowing for recombinant expression of a polypeptide, such as an immunoglobulin polypeptide and/or a bait. Such methods and host cells comprising such genes and proteins are part of the present invention. A prokaryotic host cell can also be used as a host cell in the antibody display system of the present invention, as discussed herin.

As used herein, the terms "N-glycan" and "glycoform" are used interchangeably and refer to an N-linked oligosaccharide, e.g., one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. Predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)).

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ ("$Man_3$") core structure which is also referred to as the "triammnose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms." "PNGase", or "glycanase" or "glucosidase" refer to peptide N-glycosidase F (EC 3.2.2.18).

In an embodiment of the invention, O-glycosylation of glycoproteins in a "eukaryotic host cell" is controlled. The scope of the present invention includes isolated eukaryotic host cells (e.g., *Pichia pastoris*) wherein O-glycosylation is controlled (as discussed herein) as well as antibody display systems comprising such eukaryotic host cells and methods of use thereof (as discussed herein). For example, wherein O-glycan occupancy and mannose chain length are reduced. In lower eukaryote host cells such as yeast, O-glycosylation can be controlled by deleting the genes encoding one or more protein O-mannosyltransferases (Dol-PMan: Protein (Ser/Thr) Mannosyl Transferase genes) (PMTs) or by growing the host in a medium containing one or more Pmtp inhibitors. Thus, the present invention includes isolated eukaryotic host cells, antibody display systems and methods of use thereof (as is discussed herein), e.g., comprising a deletion of one or more of the genes encoding PMTs, and/or, e.g., wherein the host cell can be cultivated in a medium that includes one or more Pmtp inhibitors. Pmtp inhibitors include but are not limited to a benzylidene thiazolidinedione. Examples of benzylidene thiazolidinediones are 5-[[3,4bis(phenylmethoxy)phenyl]methylene]-4-oxo-2-thioxo-3-thiazolidineacetic Acid; 5-[[3-(1-25 Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy))phenyl]methylene]-4-oxo-2-thioxo3-thiazolidineacetic acid.

In an embodiment of the invention, a "eukaryotic host cell" includes a nucleic acid that encodes an alpha-1,2-mannosidase that has a signal peptide that directs it for secretion. For example, in an embodiment of the invention, the host cell is engineered to express an exogenous alpha-1,2-mannosidase enzyme having an optimal pH between 5.1 and 8.0, preferably between 5.9 and 7.5. In an embodiment of the invention, the exogenous enzyme is targeted to the endoplasmic reticulum or Golgi apparatus of the host cell, where it trims N-glycans such as $Man_8GlcNAc_2$ to yield $Man_3GlcNAc_2$. See U.S. Pat. No. 7,029,872.

The scope of the present invention includes such an isolated eukaryotic host cell (e.g., *Pichia pastoris*) as well as antibody display systems comprising such eukaryotic host cells and methods of use thereof (as discussed herein).

"Eukaryotic host cells" are, in an embodiment of the invention, lower eukaryote cells (e.g., yeast such as *Pichia pastoris*) that are genetically engineered to eliminate glycoproteins having alpha-mannosidase-resistant N-glycans by deleting or disrupting one or more of the beta-mannosyltransferasegenes (e.g., BMT1, BMT2, BMT3, and BMT4) (See, U.S. Published Patent Application No. 2006/0211085) or abrogating translation of RNAs encoding one or more of the beta-mannosyltransferasesusinginterfering RNA, antisense RNA, or the like. The scope of the present invention includes such an isolated eukaryotic host cell (e.g., *Pichia pastoris*) as well as antibody display systems comprising such eukaryotic host cells and methods of use thereof (as discussed herein).

"Eukaryotic host cells" also include lower eukaryote cells (e.g., yeast and filamentous fungi such as *Pichia pastoris*) that are genetically engineered to eliminate glycoproteins having phosphomannose residues, e.g., by deleting or disrupting one or both of the phosphomannosyl transferase genes PNO1 and MNN4B (See for example, U.S. Pat. Nos. 7,198,921 and 7,259,007), which can include deleting or disrupting the MNN4A gene or abrogating translation of RNAs encoding one or more of the phosphomannosyltransferases using interfering RNA, antisense RNA, or the like. In an embodiment of the invention, a "eukaryotic host cell" has been genetically modified to produce glycoproteins that have predominantly an N-glycan selected from the group consisting of complex N-glycans, hybrid N-glycans, and high mannose N-glycans wherein complex N-glycans are, in an embodiment of the invention, selected from the group consisting of $Man_3GlcNAc_2$, $GlcNAC_{(1-4)}Man_3GlcNAc_2$, $NANA_{(1-4)}GlcNAc_{(1-4)}Man_3GlcNAc_2$, and $NANA_{(1-4)}Gal_{(1-4)}Man_3GlcNAc_2$; hybrid N-glycans are, in an embodiment of the invention, selected from the group consisting of Man$_5$GlcNAc$_2$, GlcNAcMan$_5$GlcNAc$_2$, GalGlcNAcMan$_5$GlcNAc$_2$, and NANAGalGlcNAcMan$_5$GlcNAc$_2$; and high mannose N-glycans are, in an embodiment of the invention, selected from the group consisting of Man$_6$GlcNAc$_2$, Man$_7$GlcNAc$_2$, Man$_8$lcNAc$_2$, and Man$_9$GlcNAc$_2$. The scope of the present invention includes such an isolated eukaryotic host cell (e.g., *Pichia pastoris*) as well as antibody display systems comprising such eukaryotic host cells and methods of use thereof (as discussed herein).

As used herein, the term "essentially free of" as it relates to lack of a particular sugar residue, such as fucose, or galactose or the like, on a glycoprotein, is used to indicate that the glycoprotein composition is substantially devoid of N-glycans which contain such residues. Expressed in terms of purity, essentially free means that the amount of N-glycan structures containing such sugar residues does not exceed 10%, and preferably is below 5%, more preferably below 1%, most preferably below 0.5%, wherein the percentages are by weight or by mole percent.

As used herein, a glycoprotein composition "lacks" or "is lacking" a particular sugar residue, such as fucose or galactose, when no detectable amount of such sugar residue is present on the N-glycan structures. For example, in preferred embodiments of the present invention, the glycoprotein compositions are produced by lower eukaryotic organisms, as discussed herein, and will "lack fucose," because the cells of these organisms do not have the enzymes needed to produce fucosylated N-glycan structures. Thus, the term "essentially free of fucose" encompasses the term "lacking fucose." However, a composition may be "essentially free of fucose" even if the composition at one time contained fucosylated N-glycan structures or contains limited, but detectable amounts of fucosylated N-glycan structures as described above.

For example, a host cell which introduces, eliminates or modifies sugar residues on an immunoglobulin expressed in the host cell, e.g., as is discussed herein, may, in certain instances, be referred to herein as a "controlled glycosylation host cell."

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. During the cell sorting process, the cell suspension is entrained in the center of a narrow, rapidly flowing stream of liquid. The flow is arranged so that there is a separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately-prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off. The present invention encompasses methods of using the antibody display system of the present invention, e.g., as discussed herein, wherein the eukaryotic host cells that are bound to an antigen of interest (by the Fc/antigen-binding fragment) are sorted from unbound cells or cells without sufficient levels of binding, by FACS sorting, based on whether the cells are labeled with a detectable fluorescent label (e.g., wherein the antigen itself or a secondary antibody is labeled). Such sorted labeled host cells and compositions comprising such sorted labeled host cells are also part of the present invention.

A regulatable promoter is a promoter whose expression can be induced or inhibited. Embodiments of the invention include the antibody display system wherein expression of the bait is controlled by a regulatable promoter as well as methods of use thereof as discussed herein. Polynucleotides encoding the bait, operably associated with a regulatable promoter also form part of the present invention along with isolated eukaryotic host cells including the polynucleotides. Examples of regulatable promoters that occur in yeast include the GUT1 promoter, GADPH promoter and the PCK1 promoter.

In an embodiment of the invention, expression of a polynucleotide (e.g., the bait) in a eukaryotic host cell (e.g., a bait) is inhibited by exposing the cells to anti-sense RNA or by RNA interference (e.g., microRNA (miRNA) or small interfering RNA (siRNA)). Embodiments of the invention include methods of using antibody display system (e.g., as discussed herein) wherein expression of the bait is inhibited by RNA interference or anti-sense RNA. Isolated eukaryotic host cells of the present invention (e.g., as discussed herein) comprising bait and further comprising an anti-sense or RNA interference molecule that inhibits bait expression are part of the present invention.

Antibodies

Antibodies or antigen-binding fragments thereof identified in connection with use of the present invention (e.g., use of the antibody display system of the present invention) may be reformatted into any suitable form. For example, CDRs from a full antibody isolated using the antibody display system can be incorporated into a different framework (e.g., a human framework) to generate a distinct antibody or antigen-binding fragment comprising the CDRs isolated from the antibody display system of the present invention. Methods for producing chimeric, humanized and human antibodies are well known in the art. See, e.g., U.S. Pat. No. 5,530,101, issued to Queen at al., U.S. Pat. No. 5,225,539, issued to Winter et al., U.S. Pat. No. 4,816,397 issued to Boss at al. Such methods for reformatting an antibody or antigen-binding fragment or for relocating CDRs from one framework to another are conventional and well known in the art. For example, the CDRs of an antibody or antigen-binding fragment can be used to generate monoclonal antibodies, polyclonal antibodies, bispecific antibodies, chimeric antibodies, recombinant antibodies, anti-idiotypic antibodies, humanized antibodies and bispecific antibodies; or antigen-binding fragments thereof such as nanobodies, Fab, Fab', F(ab')$_2$, Fv fragments; dsFv; (dsFv)$_2$, ds diabodies; dsFv-dsFv'; single-chain antibody molecules, e.g., sc-Fv, sc-Fv dimers (bivalent diabodies); and bispecific diabodies.

A full antibody comprises a tetramer of subunits. Each tetramer has two identical pairs of polypeptide chains, each pair having one "light" chain (LC) (about 25 kDa) and one "heavy" chain (HC) (about 50-70 kDa). The amino-terminal portion of each chain includes a variable region of about 100 to 110 or more amino acids primarily responsible for antigen recognition. The carboxy-terminal portion of each chain defines a constant domain, in part, responsible for effector function. Light chains (LCs) are classified as either kappa or lambda based on the type of constant domain in the light chain. Heavy chains (HCs) are classified as gamma, mu, alpha, delta, or epsilon, based on the type of constant domain in the heavy chain, and define the antibody's isotype as IgG (e.g., IgG1, IgG2, IgG2a, IgG2b, IgG3 or IgG4), IgM, IgA (e.g., IgA1 or IgA2), IgD or IgE, respectively.

The present invention encompasses methods for making an antibody or antigen-binding fragment thereof comprising introducing, into an isolated host cell (e.g., a eukaryotic host cell such as *Pichia*, e.g., *Pichia pastoris*) comprising a bait that includes a human Fc immunoglobulin domain or functional fragment thereof (e.g., human; e.g., comprising a VH—CH1, CH2-CH3 or CH3 polypeptide) fused to a surface anchor polypeptide or functional fragment thereof, one or more polynucleotides encoding an immunoglobulin light chain variable region; and/or one or more polynucleotides encoding an immunoglobulin heavy chain variable region and culturing the host cell under condition whereby the polynucleotides encoding the immunoglobulin chains are expressed and an antibody or antigen-binding fragment thereof is formed from said chains.

In an embodiment of the invention, said bait is operably associated with a regulatable promoter and the bait expression is inhibited when said immunoglobulin chains are expressed. In an embodiment of the invention, bait expression is inhibited with anti-sense RNA or by RNA interference.

The present invention also provides a method for determining the quantity of an antibody or antigen-binding fragment thereof, e.g., by enzyme linked immunosorbent assay (ELISA). For example, in an embodiment of the invention, the method comprises culturing a eukaryotic host cell comprising an isolated polypeptide comprising a bait polypeptide (Fc immunoglobulin domain or functional fragment thereof (e.g., human; e.g., comprising a VH—CH1, CH2-CH3 or CH3 polypeptide) fused to a surface anchor polypeptide or functional fragment thereof); wherein the host cell secretes full antibody or antigen-binding fragment thereof (optionally, the antibody or fragment is isolated from the host cell and/or culture medium); and determining the quantity of the antibody or antigen-binding fragment thereof by ELISA. In an embodiment of the invention, expression of the bait is inhibited before quantitation such that the host cell expresses and secretes only full antibody. Bait polynucleotide can be operably associated with a regulatable promoter which is inhibited so as to inhibit bait expression. For example, in an embodiment of the invention, ELISA comprises coating the antigen on a solid substrate; binding the antibody or antigen-binding fragment thereof to the antigen; binding a detectably labeled secondary antibody to the antibody or fragment; and detecting the secondary antibody. In an embodiment of the invention, the secondary antibody is labeled with alkaline phosphatase or horse radish peroxidase. In an embodiment of the invention, the label is detected by binding the alkaline phosphatase (AP) or horse radish peroxidase (HRP) with substrate and measuring absorbance of the plate (e.g., HRP substrate 3,3',5,5'-tetramethylbenzidine (TMB); HRP substrate 3,3'-diaminobenzidine (DAB); or HRP substrate 2,2'-azino-bis(3-ethylbenzthiazoline-6-sulphonic acid) (ABTS); or AP substrate para-nitrophenylphosphate).

The present invention also provides a method for determining the affinity of an antibody or antigen-binding fragment thereof, that is secreted from a eukaryotic host cell in the antibody display system of the present invention, for an antigen. For example, the affinity can be determined by standard affinity ELISA, Biacore analysis or competition assays.

Antibody Display System

The present invention provides an antibody display system, composition or kit comprising (1) a eukaryotic host cell and (2) a bait comprising an Fc (e.g., a human Fc, e.g., comprising a VH—CH1, a CH3, or a CH2-CH3 polypeptide) fused, at the N- or C-terminus, (optionally, by a peptide linker such as GGG) to a surface anchor which bait is optionally linked to a signal sequence (e.g., an alpha mating factor signal sequence, e.g., from *Saccharomyces cerevisiae*); which system may be used, for example, in the identification of antibodies. Thus, in an embodiment of the invention, the host cell in the system expresses one or more immunoglobulin chains (e.g., light and heavy chains, e.g., wherein one or more of the chains are from a library source) of an antibody and/or of an Fc/antigen-binding fragment thereof. In an embodiment of the invention, the immunoglobulin chains of an antibody and/or of an Fc/antigen-binding fragment thereof comprises an identical or different CH2-CH3 polypeptide from that of the bait.

An Fc/antigen-binding fragment of an antibody (1) complexes with the Fc moiety of the bait (e.g., a human Fc, e.g., comprising a VH—CH1, CH3 or CH2-CH3 polypeptide) and (2) binds to an antigen when complexed with the bait on the surface of the host cell. An example of an Fc/antigen-binding fragment is a monovalent fragment of a full antibody (i.e., a monovalent antibody fragment). In an embodiment of the invention, the bait comprises a CH2-CH3 polypeptide or functional fragment thereof that differs at one or more residues from the CH2-CH3 of the Fc/antigen-binding fragment of an antibody. In such an embodiment of the invention, when the bait and the Fc/antigen-binding fragment of an antibody bind, a heterodimeric Fc domain is formed.

A "monovalent antibody fragment" comprises one half of an antibody, i.e., the antibody heavy chain (VH—CH1-CH2-CH3) bound to the antibody light chain (VL-CL) comprising three paired CDRs, e.g., wherein CH1 and CL are bound by a disulfide bridge, which monovalent antibody fragment is capable of detectably binding an antigen.

The "bait" comprises an Fc domain (e.g., human, rat, rabbit, goat or mouse Fc, e.g., any part of the heavy chain (e.g., human, rat, rabbit, goat or mouse) such as, for example, a CH3 polypeptide, a VH—CH1 polypeptide or a CH2-CH3 polypeptide) fused, e.g., at the amino-terminus or carboxy-terminus, to a surface anchor, which bait possesses functional properties described herein (e.g., as set forth below) that enable the bait to function in the antibody display system of the present invention. The Fc domain can, in an embodiment of the invention, be mutated so as to improve its ability to function in the antibody display system of the present invention, for example, cysteines or other residues may be added or moved to allow for more extensive disulfide bridges to form when complexed with a human IgG Fc or Fc/antigen-binding fragment. An Fc suitable for use in the bait comprises an Fc (i.e., comprising the CH1 and/or CH2 and/or CH3 domains) or functional fragment thereof (e.g., from an IgG1, IgG2, IgG3 or IgG4 or a mutant thereof) that is capable of dimerizing, when fused to a surface anchor protein, with, for example, a human IgG Fc or with the Fc/antigen-binding fragment on the surface of a eukaryotic host cell. In an embodiment of the invention, the term "Fc" refers to the "fragment crystallized" C-terminal region of an antibody containing the CH2 and CH3 domains. In an embodiment of the invention, dimerization between the bait Fc and the Fc/antigen-binding fragment occurs intracellularly, prior to routing to the cell surface, wherein the Fc and an Fc/antigen-binding fragment remain associated once at the cell surface. In general, in the absence of the Fc/antigen-binding fragment, the bait homodimerizes; thus comprising two surface anchors and two Fc domains. In an embodiment of the invention, a full antibody that is co-expressed with the bait comprises light and heavy chains capable of dimerizing with each other to form a monovalent antibody fragment, which monovalent antibody fragment dimerizes with the Fc of the bait.

An antigen can be any immunogenic molecule or substance, for example, a polypeptide (e.g., an oligopeptide), a cell membrane, cell extract or a whole cell. Polypeptide antigens include, for example, the following polypeptides: chemokines, cytokines (e.g., inflammatory cytokines or chemokines), receptors, PCSK9, granulocyte-CSF; coagulation factors such as factor VIII, factor IX, and human protein C; soluble IgE receptor alpha-chain; urokinase; chymase and urea trypsin inhibitor; IGF-binding protein; insulin-like growth factor-1 receptor, vascular epidermal growth factor, epidermal growth factor; growth hormone-releasing factor; GITR (glucocorticoid-induced TNFR-related protein), annexin V fusion protein; IL-23p19, IL-23p40, IL-23R, IL12R-beta 1, TNF alpha (tumor necrosis factor alpha), TGF beta (transforming growth factor beta), IL-10, IL-17, TSLP (Thymic stromal lymphopoietin), angiostatin; vascular endothelial growth factor-2; myeloid progenitor inhibitory factor-1; osteoprotegerin (OPG), RANK (receptor activator for nuclear factor kappa B) or RANKL (receptor activator for nuclear factor kappa B ligand); any of which can be, in an embodiment of the invention, human.

A "surface anchor" is any polypeptide that, when fused with an Fc or functional fragment thereof, is expressed and located to the cell surface where an Fc/antigen-binding fragment can complex with the Fc or functional fragment thereof. An example of a cell surface anchor is a protein such as, but not limited to, SED-1, α-agglutinin, Cwp1, Cwp2, Gas1, Yap3, FloIp1 Crh2, Pir1, Pir4, Tip1, Wpi, Hpwp1, Als3, and Rbt5; for example, *Saccharomyces cerevisiae* CWP1, CWP2, SED1, or GAS1; *Pichia pastoris* SP1 or GAS1; or *H. polymorpha* TIP1. In an embodiment of the invention, the surface anchor is any glycosylphosphatidylinositol-anchored (GPI) protein. A functional fragment of a surface anchor comprises a fragment of a full surface anchor polypeptide that is capable of forming a functional bait when fused to an Fc or functional fragment thereof; e.g., wherein the fragment, when expressed in a eukaryotic host cell as a Fc fusion, is located on the cell surface wherein the Fc is capable of forming a complex with an Fc/antigen-binding fragment (e.g., a monovalent antibody fragment).

As discussed herein, a suitable eukaryotic host cell for use in the antibody display system of the present invention is a *Pichia* cell such as *Pichia pastoris*.

The scope of the present invention encompasses an isolated eukaryotic host cell (e.g., *Pichia pastoris*) comprising a bait (i.e., comprising the human Fc domain or functional fragment thereof fused, e.g., at the amino-terminus or carboxy-terminus, to the surface anchor or functional fragment thereof) on the cell surface wherein the bait is dimerized with an Fc/antigen-binding fragment, e.g., by binding between the bait Fc and the heavy chain of a monovalent antibody fragment (e.g., between the CH2-CH3 polypeptides in the bait and the Fc/antigen-binding fragment). The present invention also includes a composition comprising a eukaryotic host cell comprising a bait and secreted antibody or antigen-binding fragment thereof and/or Fc/antigen-binding fragment thereof, e.g., in a liquid culture medium.

The present invention provides, for example, a method for identifying (i) an antibody or Fc/antigen-binding fragment thereof that binds specifically to an antigen of interest and/or (ii) a polynucleotide encoding an immunoglobulin heavy chain of said antibody or fragment and/or a polynucleotide encoding an immunoglobulin light chain of said antibody or fragment. The method comprises, in an embodiment of the invention:

(a) co-expressing a bait (e.g., comprising a polypeptide comprising a CH3, VH—CH1 or CH2-CH3 polypeptide that is linked to a cell surface anchor, such as SED1) and one or more heavy and light immunoglobulin chains (e.g., wherein one or more of such chains are encoded by a polynucleotide from a library source) in an isolated eukaryotic host cell (e.g., *Pichia pastoris*) such that a complex between the Fc moiety of the bait (e.g., comprising a VH—CH1, CH3 or CH2-CH3 polypeptide) and an Fc/antigen-binding fragment (e.g., a monovalent antibody fragment) comprising the immunoglobulin chains forms, and is located at the cell surface; for example, wherein the host cell is transformed with one or more polynucleotides encoding the bait and the immunoglobulin chains;

(b) identifying a eukaryotic host cell expressing the bait, dimerized with the Fc/antigen-binding fragment of the antibody (e.g., a monovalent antibody fragment), which has detectable affinity (e.g., acceptable affinity) for the antigen (e.g., which detectably binds to the antigen); for example, wherein the bait, and light and heavy chain immunoglobulins are encoded by the polynucleotides in the eukaryotic host cell;

In an embodiment of the invention, non-tethered, secreted full antibodies comprising light and heavy chain immunoglobulin variable domains identical to those complexed with the bait (e.g., immunoglobulins that are expressed from the host cell) are analyzed to determine if they possess detectable affinity.

In an embodiment of the invention, the full antibodies are secreted from the host cell into the medium. In an embodiment of the invention, the full antibodies are isolated from the host cell.

In an embodiment of the invention, after step (b), expression of the bait in the host cell is inhibited, but expression of the full antibodies is not inhibited. In this embodiment of the invention, the host cell expresses only the full antibody but does not express the bait at any significant quantity. Once expression of the bait is inhibited, in an embodiment of the invention, the full antibody produced from the host cell is analyzed to determine if it possesses detectable affinity (e.g., acceptable affinity); and, (c) identifying said antibodies or antigen-binding fragments or polynucleotides if detectable binding of the Fc/antigen-binding fragment is observed, e.g., wherein one or more of the polynucleotides encoding the light and/or heavy chain immunoglobulin are optionally isolated from the host cell. In an embodiment of the invention, the nucleotide sequence of the polynucleotide is determined.

In an embodiment of the invention, a population of host cells express a common bait and a common immunoglobulin heavy chain as well a variety of different light chain immunoglobulins, e.g., from a library source, wherein individual light chain immunoglobulins that form Fc/antigen-binding fragments and full antibodies that are tethered to the bait and which exhibit antigen binding can be identified. Similarly, in an embodiment of the invention, a population of host cells express a common bait and a common immunoglobulin light chain as well a variety of different heavy chain immunoglobulins, e.g., from a library source, wherein individual heavy chain immunoglobulins that form Fc/antigen-binding fragments and full antibodies that are tethered to the bait and which exhibit antigen binding can be identified.

In an embodiment of the invention, the host cell possessing polynucleotides encoding the heavy and light chain immunoglobulins can be further used to express the secreted non-tethered antibody (e.g., full antibody) or an antigen-binding fragment thereof in culture. For example, in this embodiment of the invention, expression of the bait is optionally inhibited so that bait expression at significant quantities does not occur. The host cell is then cultured in a culture medium under conditions whereby secreted, non-tethered antibody (e.g., full antibody) or antigen-binding fragment thereof is expressed and secreted from the host cell. The non-tethered antibody or antigen-binding fragment thereof can optionally be isolated from the host cell and culture medium. In an embodiment of the invention, the immunoglobulin chains are transferred to a separate host cell (e.g., lacking the antibody display system components) for recombinant expression.

The present invention provides, for example, a method for identifying (i) an antibody or Fc/antigen-binding fragment thereof that binds specifically to an antigen of interest which comprises a second CH2-CH3 that differs from a first CH2-CH3 of a bait at one or more residues or (ii) a polynucleotide encoding an immunoglobulin heavy chain of said antibody or fragment and/or a polynucleotide encoding an immunoglobulin light chain of said antibody or fragment. The method comprises, in an embodiment of the invention:

(a) co-expressing a bait comprising a first CH2-CH3 polypeptide; along with a heavy immunoglobulin chain comprising said second CH2-CH3 polypeptide (e.g., wherein said heavy immunoglobulin chain is from a library source) and a light immunoglobulin chain (e.g., VL-CL), in an isolated eukaryotic host cell (e.g., Pichia pastoris) such that a complex between the first CH2-CH3 polypeptide of the bait and the second CH2-CH3 polypeptide of a Fc/antigen-binding fragment binds and is located at the cell surface; for example, wherein the host cell is transformed with one or more polynucleotides encoding the bait and the immunoglobulin chains;

(b) identifying a eukaryotic host cell expressing the bait, dimerized with the Fc/antigen-binding fragment which has detectable affinity (e.g., acceptable affinity) for the antigen; for example, wherein the bait, and light and heavy chain immunoglobulins are encoded by the polynucleotides in the eukaryotic host cell; and, optionally, (c) identifying said antibodies or antigen-binding fragments or polynucleotides if detectable binding of the Fc/antigen-binding fragment is observed, e.g., wherein one or more of the polynucleotides encoding the light and/or heavy chain immunoglobulin are optionally isolated from the host cell. In an embodiment of the invention, the nucleotide sequence of the polynucleotide is determined.

The antibody display system of the present invention may be use to evaluate the effects of a given glycosylation pattern on the affinity of an antibody or antigen-binding fragment thereof for an antigen. In general, the ability of the Fc/antigen-binding fragment comprising an altered glyosylation pattern may be evaluated for binding to the antigen, after which affinity of the full antibody or antigen-binding fragment thereof can be evaluated. Glycosylation patterns can be modified on the immunoglobulin chains expressed in the antibody display system, for example, by using a host cell, e.g., as is discussed herein, that modifies the glycosylation patterns when the chains are expressed and/or by culturing a host under conditions whereby the glycosylation pattern is modified, e.g., as discussed herein. For example, in an embodiment of the invention, the method comprise contacting an antibody display system with said antigen; wherein the antibody display system comprises: (a) an isolated eukaryotic controlled glycosylation host cell comprising a polynucleotide encoding an immunoglobulin light chain; and a polynucleotide encoding an immunoglobulin heavy chain; and (b) a bait comprising an Fc immunoglobulin domain or functional fragment thereof fused to a surface anchor polypeptide or functional fragment thereof on the surface of said eukaryotic host cell; wherein the Fc of said bait complexes with an Fc/antigen-binding fragment comprising said immunoglobulin heavy and immunoglobulin light chains on the surface of the host cell; wherein said heavy or light chain comprises said sugar; determining if said Fc/antigen-binding fragment specifically binds to said antigen; determining the binding affinity of the antibody or antigen-binding fragment thereof comprising said sugar for the antigen; and comparing the affinity of the antibody or antigen-binding fragment thereof with affinity of an otherwise identical antibody or antigen-binding fragment thereof which lacks said sugar; wherein the sugar is determined to increase affinity for the antigen if the affinity of the antibody or antigen-binding fragment thereof comprising said sugar is higher than the affinity of the antibody or antigen-binding fragment thereof which lacks the sugar, and/or wherein the sugar is determined to decrease affinity for the antigen if the affinity of antibody or antigen-binding fragment thereof comprising said sugar is lower than the affinity of the antibody or antigen-binding fragment thereof which lacks the sugar. For example, the affinity of the antibody or antigen-binding fragment thereof lacking the sugar can be determined in a similar manner in the antibody display system of the present invention or the affinity or it can be determined directly by measuring affinity by a known method such as ELISA, biacore assay or a competition assay.

Bait expression can be inhibited by any of several acceptable means. For example, the polynucleotides encoding the bait (e.g., the surface anchor and/or Fc) can be expressed by a regulatable promoter whose expression can be inhibited in the host cell. In an embodiment of the invention, bait expression is inhibited by RNA interference, anti-sense RNA, mutation or removal of the polynucleotide encoding the bait (e.g., surface anchor and/or Fc) from the host cell or genetic mutation of the polynucleotide so that the host cell does not express a functional bait.

"Acceptable affinity" refers to antibody or antigen-binding fragment affinity for the antigen which is at least $10^{-3}$ M or a greater affinity (lower number), e.g., $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M or $10^{-12}$ M.

In an embodiment of the present invention, polynucleotides encoding the antibody or Fc/antigen-binding fragment (e.g., monovalent antibody fragment) heavy and light chain are in one or more libraries of polynucleotides that encode light and/or heavy chain immunoglobulins (e.g., one library encoding light chains and one library encoding heavy chains). The particular immunoglobulin chains of interest are, in this embodiment, distinguished from the other chains in the library when the surface-anchored Fc/antigen-binding fragment on the host cell surface is observed to bind to an antigen of interest.

In an embodiment of the invention, the heavy or light chain immunoglobulin expressed in the antibody display system is from a library source and the other immunoglobulin chain is known (i.e., a single chain from a clonal source). In this embodiment of the invention, the antibody display system can be used, as discussed herein, to identify a new library chain that forms desirable antibodies or antigen-binding fragments thereof when coupled with the known chain. Alternatively, the antibody display system can be used to analyze expression and binding characteristics of an antibody or antigen-binding fragment thereof comprising two known immunoglobulin chains.

In an embodiment of the invention, cells expressing Fc/antigen-binding fragments tethered to the cell by an anchor such as SED1 that bind to an antigen can be detected by incubating the cells with fluorescently labeled antigen (e.g., biotin label) and sorting/selecting cells that specifically bind the antigen by fluorescence-activated cell sorting (FACS).

In an embodiment of the invention, the eukaryotic host cells expressing the bait dimerized with the Fc/antigen-binding fragment are identified and sorted using fluorescence-activated cell sorting (FACS). For example, in an embodiment of the invention, cells expressing the bait dimerized with the Fc/antigen-binding fragment on the cell surface are labeled with a fluorescent antigen or fluorescent secondary antibody that also binds to the antigen. The fluorescent label is detected during the FACS sorting and used as the signal for sorting. Labeled cells indicate the presence of a cell surface expressed bait/Fc/antigen-binding fragment/antigen complex and are collected in one vessel whereas cells not expressing signal are collected in a separate vessel. The present invention, accordingly, includes the a method comprising the following steps for determining if an antibody or antigen-binding fragment thereof from a library specifically binds to an antigen:

(1) Transform:
  (i) one or more immunoglobulin libraries, containing polynucleotides encoding light and heavy chain immunoglobulins;
  (ii) one or more immunoglobulin libraries, containing polynucleotides encoding light chain immunoglobulins and a single clonal heavy chain immunoglobulin; or
  (iii) one or more immunoglobulin libraries, containing polynucleotides encoding heavy chain immunoglobulins and a single clonal light chain immunoglobulin;
  wherein, said chains are capable of forming an antibody or antigen-binding fragment thereof, into a eukaryotic host cell comprising polynucleotides encoding the bait (e.g., *Pichia pastoris*);
(2) Grow transformed cells in a liquid culture medium;
(3) Allow expression of the bait on the surface of the cells;
(4) Label the cells with fluorescently labeled antigen or antigen bound to a fluorescently labeled secondary antibody;
(5) Sort and isolate fluorescently labeled cells using FACS for one round;
(6) Regrow the labeled, sorted cells;
(7) Allow expression of the bait in the cells;
(8) Label the cells with fluorescently labeled antigen or antigen bound to a fluorescently labeled secondary antibody;
(9) Sort and isolate fluorescently labeled cells using FACS for a second round;
(10) Regrow the labeled, sorted cells on solid culture medium so that individual cellular clones grow into discrete cellular colonies;
(11) Identify colonies with affinity for the antigen;
(12) Grow cells from identified colonies in a liquid culture medium and isolate supernatant containing full, non-tethered antibody or antigen-binding fragment thereof comprising the immunoglobulin light and heavy chains; wherein, expression of the bait is optionally inhibited;
(13) Determine affinity of non-tethered antibodies or antigen-binding fragments thereof, from the supernatant, for the antigen and identify clones with acceptable affinity (e.g., by Biacore analysis);
(14) Determine the nucleotide sequence of polynucleotides in the identified clones encoding the heavy and light chain immunoglobulins.

The scope of the present invention also includes a method for identifying polynucleotides encoding a heavy chain and light chain immunoglobulin of an antibody or for identifying an antibody which exhibits high stability. Such a method comprises the following steps:

(a) co-expressing the bait and the polynucleotides encoding the heavy and light chains in a eukaryotic host cell (e.g., *Pichia pastoris*) while subjecting antibodies comprising said chains to a denaturant;

In an embodiment of the invention, a denaturant is present in a concentration or amount or magnitude (e.g., at a sufficiently high temperature) that a practitioner of ordinary skill in the art would expect to, at least partially, denature an antibody and, thus, inhibit its ability to bind to an antigen. For example, possible denaturants include urea (e.g., 2, 3, 4, 5 or 6 M or more), detergent such as triton X-100 (e.g., 1% or more), dithiothreitol (DTT) (e.g., 250 mM or 500 mM or more), guanidine hydrochloride, light (e.g., ultraviolet or visible), extreme pH (e.g., 1, 2, 3, 14, 13 or 12) or a temperature above about 4° C., such as 37° C. (e.g., 42° C., 48° C. or 50° C.) or any combination thereof (e.g., 500 mM DTT/6 M urea).

(b) identifying a eukaryotic host cell expressing the bait, dimerized with the Fc/antigen-binding fragment (e.g., a monovalent antibody fragment), which fragment has detectable affinity (e.g., acceptable affinity) for the antigen;

In an embodiment of the invention, full antibodies comprising light and heavy chain variable regions identical to those complexed with the bait are also analyzed to determine if they possess detectable affinity.

In an embodiment of the invention, the full antibodies are secreted from the host cell. In an embodiment of the invention, the full antibodies are isolated from the host cell.

In an embodiment of the invention, expression of the bait in the host cell is inhibited, but expression of the full antibodies is not inhibited. In this embodiment of the invention, the host cell expresses only the full antibody but does not express the bait at any significant quantity. Once expression of the bait is inhibited, in an embodiment of the invention, the full antibody produced from the host cell is analyzed to determine if it possesses detectable affinity (e.g., acceptable affinity).

and, (c) identifying said antibodies or polynucleotides encoding the heavy and light chains from the cell wherein one or more of the polynucleotides are optionally isolated from the host cell; wherein antibodies exhibiting affinity for the antigen in the presence of denaturant are determined to exhibit high stability. In an embodiment of the invention, the nucleotide sequence of the polynucleotide is determined.

In an embodiment of the invention, a human Fc immunoglobulin domain for use in a bait comprises the following amino acid sequence:

(SEQ ID NO: 1)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSR

WQQGNVFSCSVMHEALHNHYTQKSLSLSPG

In an embodiment of the invention, SED1 comprises the following amino acid sequence:

(SEQ ID NO: 2)
VDQFSNSTSASSTDVTSSSSISTSSGSVTITSSEAPESDNGTSTAAPTE
TSTEAPTTAIPTNGTSTEAPTTAIPTNGTSTEAPTDTTTEAPTTALPTN
GTSTEAPTDTTTEAPTTGLPTNGTTSAFPPTTSLPPSNTTTTPPYNPST
DYTTDYTVVTEYTTYCPEPTTFTTNGKTYTVTEPTTLTITDCPCTIEKP
TTTSTTEYTVVTEYTTYCPEPTTFTTNGKTYTVTEPTTLTITDCPCTIE
KSEAPESSVPVTESKGTTTKETGVTTKQTTANPSLTVSTVVPVSSSASS
HSVVINSNGANVVVPGALGLAGVAMLFL

In an embodiment of the invention, the human Fc immunoglobulin fused to the SED1 polypeptide is linked to a signal sequence such as an alpha mating factor signal sequence (e.g., MRFPSIFTAVLFAASSALA (SEQ ID NO: 3))

In an embodiment of the invention, the bait comprising the human Fc immunoglobulin domain fused to a SED1 polypeptide comprise the amino acid sequence:

(SEQ ID NO: 4)
MRFPSIFTAVLFAASSALA<u>DKTHTCPPCPAPELLGGPSVFLFPPKPKDT
LMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPG</u>
GGGVDQFSNSTSASSTDVTSSSSISTSSGSVTITSSEAPESDNGTSTAA
PTETSTEAPTTAIPTNGTSTEAPTTAIPTNGTSTEAPTDTTTEAPTTAL
PTNGTSTEAPTDTTTEAPTTGLPTNGTTSAFPPTTSLPPSNTTTTPPYN
PSTDYTTDYTVVTEYTTYCPEPTTFTTNGKTYTVTEPTTLTITDCPCTI
EKPTTTSTTEYTVVTEYTTYCPEPTTFTTNGKTYTVTEPTTLTITDCPC
TIEKSEAPESSVPVTESKGTTTKETGVTTKQTTANPSLTVSTVVPVSSS
ASSHSVVINSNGANVVVPGALGLAGVAMLFL.

The Fc immunoglobulin domain is underscored and the linked is in bold face font. The SED1 polypeptide follows the linker and an alpha mating factor signal peptide is before the Fc.

EXAMPLES

The present invention is intended to exemplify the present invention and not to be a limitation thereof. The methods and compositions (e.g., polypeptides, polynucleotides, plasmids, yeast cells) disclosed below fall within the scope of the present invention.

Example 1

Construction and Use of Antibody Display System

Construction of Antibody Display Bait

Expression cassettes were constructed as follows. A polynucleotide encoding the N-terminus of a cell surface anchoring protein that inherently contains an attached glycophosphotidylinositol (GPI) post-translational modification that anchors the protein on the yeast cell wall was linked to a nucleic acid sequence that encodes the human IgG1 Fc region. The specific cell surface anchoring protein we used was *S. cerevisiae* Sed1 protein, which had been identified by screening a panel of cell wall of plasma membrane proteins that had been identified using GPI protein prediction software (described in international publication no. WO09/111,183).

Figure 2:
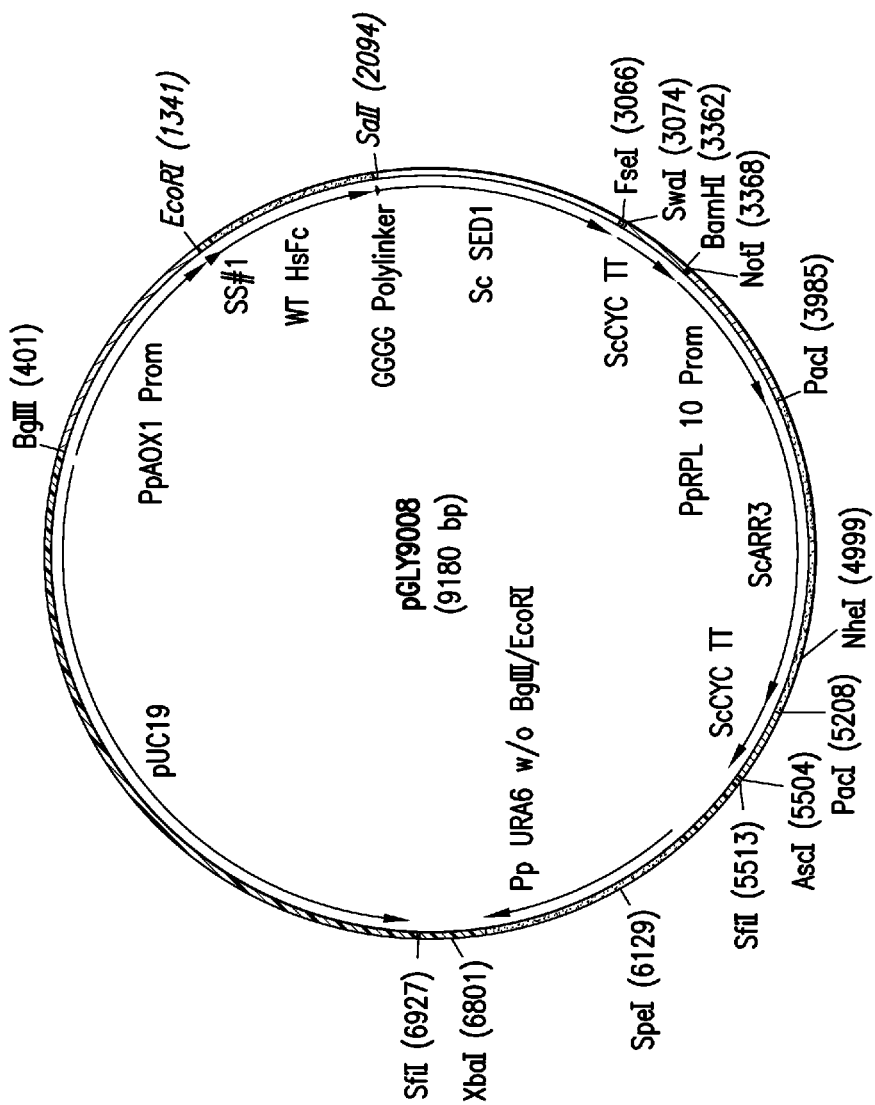
FIG. 2. Map of plasmid pGLY9008. The *Homo sapiens* Fc fused to *Saccharomyces cerevisiae* SED1 is driven by a *Pichia pastoris* AOX1 promoter.

To create the plasmid containing bait cassette, a codon optimized sequence of human IgG1 Fc fragment was synthesized using an EcoRI forward PCR primer containing the nucleic acid sequence of *S. cerevisiae* α-mating factor signal sequence fused upstream of the sequence encoding the IgG1 Fc N-terminus, and a SalI reverse primer encoding the C-terminus of IgG1 Fc that terminates in a sequence encoding a GGGG linker. A plasmid containing the anti-Her2 gene sequence was used as a PCR template for amplification of an EcoRI-α-mating factor signal sequence-Fc-GGGG-SalI fragment. Both PCR product and pGLY3033 (described in international publication no. WO09/111,183) were digested using EcoRI and SalI endonucleases. The EcoRI-SalI fragment encoding the Fc was ligated in frame to EcoRI-SalI pGLY3033 backbone to generate plasmid pGLY9008 (FIG. 2). This plasmid enables delivery of the Fc-SED1 cassette under the control of the *Pichia pastoris* AOX1 promoter sequence. Like the parent plasmid it contains, the *Pichia pastoris* URA6 gene sequence, which serves as an integration locus in the genome, and the arsenite resistance gene, to allow selection on media containing sodium aresnite.

The pGLY3033 plasmid sequence comprises the nucleotide sequence:

(SEQ ID NO: 5)
TCGCGCGTTTCGGTGATGACGGTGAAAACCTCTGACACATGCAGCTCCC
GGAGACGGTCACAGCTTGTCTGTAAGCGGATGCCGGGAGCAGACAAGCC
CGTCAGGGCGCGTCAGCGGGTGTTGGCGGGTGTCGGGGCTGGCTTAACT
ATGCGGCATCAGAGCAGATTGTACTGAGAGTGCACCATATGCGGTGTGA
AATACCGCACAGATGCGTAAGGAGAAAATACCGCATCAGGCGCCATTCG
CCATTCAGGCTGCGCAACTGTTGGGAAGGGCGATCGGTGCGGGCCTCTT
CGCTATTACGCCAGCTGGCGAAAGGGGGATGTGCTGCAAGGCGATTAAG
TTGGGTAACGCCAGGGTTTTCCCAGTCACGACGTTGTAAAACGACGGCC
AGTGAATTGAGATCTAACATCCAAAGACGAAAGGTTGAATGAAACCTTT
TTGCCATCCGACATCCACAGGTCCATTCTCACACATAAGTGCCAAACGC
AACAGGAGGGGATACACTAGCAGCAGACCGTTGCAAACGCAGGACCTCC
ACTCCTCTTCTCCTCAACACCCACTTTTGCCATCGAAAAACCAGCCCAG
TTATTGGGCTTGATTGGAGCTCGCTCATTCCAATTCCTTCTATTAGGCT
ACTAACACCATGACTTTATTAGCCTGTCTATCCTGGCCCCCCTGGCGAG
GTTCATGTTTGTTTATTTCCGAATGCAACAAGCTCCGCATTACACCCGA
ACATCACTCCAGATGAGGGCTTTCTGAGTGTGGGGTCAAATAGTTTCAT
GTTCCCCAAATGGCCCAAAACTGACAGTTTAAACGCTGTCTTGGAACCT
AATATGACAAAAGCGTGATCTCATCCAAGATGAACTAAGTTTGGTTCGT
TGAAATGCTAACGGCCAGTTGGTCAAAAAGAAACTTCCAAAAGTCGGCA
TACCGTTTGTCTTGTTTGGTATTGATTGACGAATGCTCAAAAATAATCT
CATTAATGCTTAGCGCAGTCTCTCTATCGCTTCTGAACCCCGGTGCACC
TGTGCCGAAACGCAAATGGGGAAACACCCGCTTTTTGGATGATTATGCA
TTGTCTCCACATTGTATGCTTCCAAGATTCTGGTGGGAATACTGCTGAT

-continued

```
AGCCTAACGTTCATGATCAAAATTTAACTGTTCTAACCCCTACTTGACA
GCAATATATAAACAGAAGGAAGCTGCCCTGTCTTAAACCTTTTTTTTA
TCATCATTATTAGCTTACTTTCATAATTGCGACTGGTTCCAATTGACAA
GCTTTTGATTTTAACGACTTTTAACGACAACTTGAGAAGATCAAAAAAC
AACTAATTATTCGAAACGGAATTCacgatggtcgcttggtggtctttgt
ttctgtacggtcttcaggtcgctgcacctgctttggctACTTCCAGATT
GGAGGGATTGCAATCCGAAAACCACAGATTGAGAATGAAGATCACTGAG
TTGGACAAGGACTTGGAGGAAGTTACTATGCAGTTGCAGGATGTTGGTG
GTTGTGAGCAGAAGTTGATCTCCGAAGAGGATTTGGTCGACCAATTCTC
TAACTCTACTTCCGCTTCCTCTACTGACGTTACTTCCTCCTCCTCTATT
TCTACTTCCTCCGGTTCCGTTACTATTACTTCCTCTGAGGCTCCAGAAT
CTGACAACGGTACTTCTACTGCTGCTCCAACTGAAACTTCTACTGAGGC
TCCTACTACTGCTATTCCAACTAACGGAACTTCCACAGAGGCTCCAACA
ACAGCTATCCCTACAAACGGTACATCCACTGAAGCTCCTACTGACACTA
CTACAGAAGCTCCAACTACTGCTTTGCCTACTAATGGTACATCAACAGA
GGCTCCTACAGATACAACAACTGAAGCTCCAACAACTGGATTGCCAACA
AACGGTACTACTTCTGCTTTCCCACCAACTACTTCCTTGCCACCATCCA
ACACTACTACTACTCCACCATACAACCCATCCACTGACTACACTACTGA
CTACACAGTTGTTACTGAGTACACTACTTACTGTCCAGAGCCAACTACT
TTCACAACAAACGGAAAGACTTACACTGTTACTGAGCCTACTACTTTGA
CTATCACTGACTGTCCATGTACTATCGAGAAGCCAACTACTACTTCCAC
TACAGAGTATACTGTTGTTACAGAATACACAACATATTGTCCTGAGCCA
ACAACATTCACTACTAATGGAAAAACATACACAGTTACAGAACCAACTA
CATTGACAATTACAGATTGTCCTTGTACAATTGAGAAGTCCGAGGCTCC
TGAATCTTCTGTTCCAGTTACTGAATCCAAGGGTACTACTACTAAAGAA
ACTGGTGTTACTACTAAGCAGACTACTGCTAACCCATCGTTGACTGTTT
CCACTGTTGTTCCAGTTTCTTCCTCTGCTTCTTCCCACTCCGTTGTTAT
CAACTCCAACGGTGCTAACGTTGTTGTTCCTGGTGCTTTGGGATTGGCT
GGTGTTGCTATGTTGTTCTTGTAATAGGGCCGGCCATTTAAATACAGGC
CCCTTTTCCTTTGTCGATATCATGTAATTAGTTATGTCACGCTTACATT
CACGCCCTCCTCCCACATCCGCTCTAACCGAAAAGGAAGGAGTTAGACA
ACCTGAAGTCTAGGTCCCTATTTATTTTTTTAATAGTTATGTTAGTAT
TAAGAACGTTATTTATATTTCAAATTTTTCTTTTTTCTGTACAAACG
CGTGTACGCATGTAACATTATACTGAAAACCTTGCTTGAGAAGGTTTTG
GGACGCTCGAAGGCTTTAATTTGCAAGCTGGATCCGCGGCCGCTTACGC
GCCGTTCTTCGCTTGGTCTTGTATCTCCTTACACTGTATCTTCCCATTT
GCGTTTAGGTGGTTATCAAAAACTAAAAGGAAAAATTTCAGATGTTTAT
CTCTAAGGTTTTTTCTTTTTACAGTATAACACGTGATGCGTCACGTGGT
ACTAGATTACGTAAGTTATTTTGGTCCGGTGGGTAAGTGGGTAAGAATA
GAAAGCATGAAGGTTTACAAAAACGCAGTCACGAATTATTGCTACTTCG
AGCTTGGAACCACCCCAAAGATTATATTGTACTGATGCACTACCTTCTC
GATTTTGCTCCTCCAAGAACCTACGAAAAACATTTCTTGAGCCTTTTCA
ACCTAGACTACACATCAAGTTATTTAAGGTATGTTCCGTTAACATGTAA
GAAAAGGAGAGGATAGATCGTTTATGGGGTACGTCGCCTGATTCAAGCG
TGACCATTCGAAGAATAGGCCTTCGAAAGCTGAATAAAGCAAATGTCAG
TTGCGATTGGTATGCTGACAAATTAGCATAAAAAGCAATAGACTTTCTA
ACCACCTGTTTTTTTCCTTTTACTTTATTTATATTTTGCCACCGTACTA
ACAAGTTCAGACAAATTAATTAACACCATGTCAGAAGATCAAAAAAGTG
AAAATTCCGTACCTTCTAAGGTTAATATGGTGAATCGCACCGATATACT
GACTACGATCAAGTCATTGTCATGGCTTGACTTGATGTTGCCATTTACT
ATAATTCTCTCCATAATCATTGCAGTAATAATTTCTGTCTATGTGCCTT
CTTCCCGTCACACTTTTGACGCTGAAGGTCATCCCAATCTAATGGGAGT
GTCCATTCCTTTGACTGTTGGTATGATTGTAATGATGATTCCCCCGATC
TGCAAAGTTTCCTGGGAGTCTATTCACAAGTACTTCTACAGGAGCTATA
TAAGGAAGCAACTAGCCCTCTCGTTATTTTTGAATTGGGTCATCGGTCC
TTTGTTGATGACAGCATTGGCGTGGATGGCGCTATTCGATTATAAGGAA
TACCGTCAAGGCATTATTATGATCGGAGTAGCTAGATGCATTGCCATGG
TGCTAATTTGGAATCAGATTGCTGGAGGAGACAATGATCTCTGCGTCGT
GCTTGTTATTACAAACTCGCTTTTACAGATGGTATTATATGCACCATTG
CAGATATTTTACTGTTATGTTATTTCTCATGACCACCTGAATACTTCAA
ATAGGGTATTATTCGAAGAGGTTGCAAAGTCTGTCGGAGTTTTTCTCGG
CATACCACTGGGAATTGGCATTATCATACGTTTGGGAAGTCTTACCATA
GCTGGTAAAAGTAATTATGAAAAATACATTTTGAGATTTATTTCTCCAT
GGGCAATGATCGGATTTCATTACACTTTATTTGTTATTTTTATTAGTAG
AGGTTATCAATTTATCCACGAAATTGGTTCTGCAATATTGTGCTTTGTC
CCATTGGTGCTTTACTTCTTTATTGCATGGTTTTTGACCTTCGCATTAA
TGAGGTACTTATCAATATCTAGGAGTGATACACAAAGAGAATGTAGCTG
TGACCAAGAACTACTTTTAAAGAGGGTCTGGGGAAGAAAGTCTTGTGAA
GCTAGCTTTTCTATTACGATGACGCAATGTTTCACTATGGCTTCAAATA
ATTTTGAACTATCCCTGGCAATTGCTATTTCCTTATATGGTAACAATAG
CAAGCAAGCAATAGCTGCAACATTTGGGCCGTTGCTAGAAGTTCCAATT
TTATTGATTTTGGCAATAGTCGCGAGAATCCTTAAACCATATTATATAT
GGAACAATAGAAATTAATTAACAGGCCCCTTTTCCTTTGTCGATATCAT
GTAATTAGTTATGTCACGCTTACATTCACGCCCTCCTCCCACATCCGCT
CTAACCGAAAAGGAAGGAGTTAGACAACCTGAAGTCTAGGTCCCTATTT
ATTTTTTTAATAGTTATGTTAGTATTAAGAACGTTATTTATATTTCAA
ATTTTTCTTTTTTCTGTACAAACGCGTGTACGCATGTAACATTATAC
TGAAAACCTTGCTTGAGAAGGTTTTGGGACGCTCGAAGGCTTTAATTTG
CAAGCTGCGGCCTAAGGCGCGCCAGGCCATAATGGCCCAAATGCAAGAG
GACATTAGAAATGTGTTTGGTAAGAACATGAAGCCGGAGGCATACAAAC
GATTCACAGATTTGAAGGAGGAAAACAAACTGCATCCACCGGAAGTGCC
```

```
AGCAGCCGTGTATGCCAACCTTGCTCTCAAAGGCATTCCTACGGATCTG
AGTGGGAAATATCTGAGATTCACAGACCCACTATTGGAACAGTACCAAA
CCTAGTTTGGCCGATCCATGATTATGTAATGCATATAGTTTTTGTCGAT
GCTCACCCGTTTCGAGTCTGTCTCGTATCGTCTTACGTATAAGTTCAAG
CATGTTTACCAGGTCTGTTAGAAACTCCTTTGTGAGGGCAGGACCTATT
CGTCTCGGTCCCGTTGTTTCTAAGAGACTGTACAGCCAAGCGCAGAATG
GTGGCATTAACCATAAGAGGATTCTGATCGGACTTGGTCTATTGGCTAT
TGGAACCACCCTTTACGGGACAACCAACCCTACCAAGACTCCTATTGCA
TTTGTGGAACCAGCCACGGAAAGAGCGTTTAAGGACGGAGACGTCTCTG
TGATTTTGTTCTCGGAGGTCCAGGAGCTGGAAAAGGTACCCAATGTGC
CAAACTAGTGAGTAATTACGGATTTGTTCACCTGTCAGCTGGAGACTTG
TTACGTGCAGAACAGAAGAGGGAGGGGTCTAAGTATGGAGAGATGATTT
CCCAGTATATCAGAGATGGACTGATAGTACCTCAAGAGGTCACCATTGC
GCTCTTGGAGCAGGCCATGAAGGAAAACTTCGAGAAAGGGAAGACACGG
TTCTTGATTGATGGATTCCCTCGTAAGATGGACCAGGCCAAAACTTTTG
AGGAAAAAGTCGCAAAGTCCAAGGTGACACTTTTCTTTGATTGTCCCGA
ATCAGTGCTCCTTGAGAGATTACTTAAAAGAGGACAGACAAGCGGAAGA
GAGGATGATAATGCGGAGAGTATCAAAAAAAGATTCAAAACATTCGTGG
AAACTTCGATGCCTGTGGTGGACTATTTCGGGAAGCAAGGACGCGTTTT
GAAGGTATCTTGTGACCACCCTGTGGATCAAGTGTATTCACAGGTTGTG
TCGGTGCTAAAAGAGAAGGGGATCTTTGCCGATAACGAGACGGAGAATA
AATAAACATTGTAATAAGATTTAGACTGTGAATGTTCTATGTAATATTT
TTCGAGATACTGTATCTATCTGGTGTACCGTATCACTCTGGACTTGCAA
ACTCATTGATTACTTGTGCAATGGGCAAGAAGGATAGCTCTAGAAAGAA
GAAGAAAAAGGAGCCGCCTGAAGAGCTGGATCTTTCCGAGGTTGTTCCA
ACTTTTGGTTATGAGGAATTTCATGTTGAGCAAGAGGAGAATCCGGTCG
ATCAAGACGAACTTGACGGCCATAATGGCCTAGCTTGGCGTAATCATGG
TCATAGCTGTTTCCTGTGTGAAATTGTTATCCGCTCACAATTCCACACA
ACATACGAGCCGGAAGCATAAAGTGTAAAGCCTGGGGTGCCTAATGAGT
GAGCTAACTCACATTAATTGCGTTGCGCTCACTGCCCGCTTTCCAGTCG
GGAAACCTGTCGTGCCAGCTGCATTAATGAATCGGCCAACGCGCGGGA
GAGGCGGTTTGCGTATTGGGCGCTCTTCCGCTTCCTCGCTCACTGACTC
GCTGCGCTCGGTCGTTCGGCTGCGGCGAGCGGTATCAGCTCACTCAAAG
GCGGTAATACGGTTATCCACAGAATCAGGGGATAACGCAGGAAAGAACA
TGTGAGCAAAAGGCCAGCAAAAGGCCAGGAACCGTAAAAAGGCCGCGTT
GCTGGCGTTTTTCCATAGGCTCCGCCCCCTGACGAGCATCACAAAAAT
CGACGCTCAAGTCAGAGGTGGCGAAACCCGACAGGACTATAAAGATACC
AGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTC
```
```
GCTCCAAGCTGGGCTGTGTGCACGAACCCCCCGTTCAGCCCGACCGCTG
CGCCTTATCCGGTAACTATCGTCTTGAGTCCAACCCGGTAAGACACGAC
TTATCGCCACTGGCAGCAGCCACTGGTAACAGGATTAGCAGAGCGAGGT
ATGTAGGCGGTGCTACAGAGTTCTTGAAGTGGTGGCCTAACTACGGCTA
CACTAGAAGGACAGTATTTGGTATCTGCGCTCTGCTGAAGCCAGTTACC
TTCGGAAAAGAGTTGGTAGCTCTTGATCCGGCAAACAAACCACCGCTG
GTAGCGGTGGTTTTTTTGTTTGCAAGCAGCAGATTACGCGCAGAAAAAA
AGGATCTCAAGAAGATCCTTTGATCTTTTCTACGGGGTCTGACGCTCAG
TGGAACGAAAACTCACGTTAAGGGATTTTGGTCATGAGATTATCAAAAA
GGATCTTCACCTAGATCCTTTTAAATTAAAAATGAAGTTTTAAATCAAT
CTAAAGTATATATGAGTAAACTTGGTCTGACAGTTACCAATGCTTAATC
AGTGAGGCACCTATCTCAGCGATCTGTCTATTTCGTTCATCCATAGTTG
CCTGACTCCCCGTCGTGTAGATAACTACGATACGGGAGGGCTTACCATC
TGGCCCCAGTGCTGCAATGATACCGCGAGACCCACGCTCACCGGCTCCA
GATTTATCAGCAATAAACCAGCCAGCCGGAAGGGCCGAGCGCAGAAGTG
GTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCC
ATTGCTACAGGCATCGTGGTGTCACGCTCGTCGTTTGGTATGGCTTCAT
TCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGT
AAGTTGGCCGCAGTGTTATCACTCATGGTTATGGCAGCACTGCATAATT
CTCTTACTGTCATGCCATCCGTAAGATGCTTTTCTGTGACTGGTGAGTA
CTCAACCAAGTCATTCTGAGAATAGTGTATGCGGCGACCGAGTTGCTCT
TGCCCGGCGTCAATACGGGATAATACCGCGCCACATAGCAGAACTTTAA
AAGTGCTCATCATTGGAAAACGTTCTTCGGGGCGAAAACTCTCAAGGAT
CTTACCGCTGTTGAGATCCAGTTCGATGTAACCCACTCGTGCACCCAAC
TGATCTTCAGCATCTTTTACTTTCACCAGCGTTTCTGGGTGAGCAAAA
CAGGAAGGCAAAATGCCGCAAAAAAGGGAATAAGGGCGACACGGAAATG
TTGAATACTCATACTCTTCCTTTTTCAATATTATTGAAGCATTTATCAG
GGTTATTGTCTCATGAGCGGATACATATTTGAATGTATTTAGAAAAATA
AACAAATAGGGGTTCCGCGCACATTTCCCCGAAAAGTGCCACCTGACGT
CTAAGAAACCATTATTATCATGACATTAACCTATAAAAATAGGCGTATC
ACGAGGCCCTTTCGTC
```

The pGLY9008 plasmid sequence comprises the nucleotide sequence:

(SEQ ID NO: 6)
```
TCGCGCGTTTCGGTGATGACGGTGAAAACCTCTGACACATGCAGCTCCC
GGAGACGGTCACAGCTTGTCTGTAAGCGGATGCCGGGAGCAGACAAGCC
CGTCAGGGCGCGTCAGCGGGTGTTGGCGGGTGTCGGGGCTGGCTTAACT
ATGCGGCATCAGAGCAGATTGTACTGAGAGTGCACCATATGCGGTGTGA
AATACCGCACAGATGCGTAAGGAGAAAATACCGCATCAGGCGCCATTCG
```

```
CCATTCAGGCTGCGCAACTGTTGGGAAGGGCGATCGGTGCGGGCCTCTT
CGCTATTACGCCAGCTGGCGAAAGGGGATGTGCTGCAAGGCGATTAAG
TTGGGTAACGCCAGGGTTTTCCCAGTCACGACGTTGTAAAACGACGGCC
AGTGAATTGAGATCTAACATCCAAAGACGAAAGGTTGAATGAAACCTTT
TTGCCATCCGACATCCACAGGTCCATTCTCACACATAAGTGCCAAACGC
AACAGGAGGGGATACACTAGCAGCAGACCGTTGCAAACGCAGGACCTCC
ACTCCTCTTCTCCTCAACACCCACTTTTGCCATCGAAAAACCAGCCCAG
TTATTGGGCTTGATTGGAGCTCGCTCATTCCAATTCCTTCTATTAGGCT
ACTAACACCATGACTTTATTAGCCTGTCTATCCTGGCCCCCCTGGCGAG
GTTCATGTTTGTTTATTTCCGAATGCAACAAGCTCCGCATTACACCCGA
ACATCACTCCAGATGAGGGCTTTCTGAGTGTGGGGTCAAATAGTTTCAT
GTTCCCCAAATGGCCCAAAACTGACAGTTTAAACGCTGTCTTGGAACCT
AATATGACAAAAGCGTGATCTCATCCAAGATGAACTAAGTTTGGTTCGT
TGAAATGCTAACGGCCAGTTGGTCAAAAGAAACTTCCAAAAGTCGGCA
TACCGTTTGTCTTGTTTGGTATTGATTGACGAATGCTCAAAAATAATCT
CATTAATGCTTAGCGCAGTCTCTCTATCGCTTCTGAACCCCGGTGCACC
TGTGCCGAAACGCAAATGGGGAAACACCCGCTTTTTGGATGATTATGCA
TTGTCTCCACATTGTATGCTTCCAAGATTCTGGTGGGAATACTGCTGAT
AGCCTAACGTTCATGATCAAAATTTAACTGTTCTAACCCCTACTTGACA
GCAATATATAAACAGAAGGAAGCTGCCCTGTCTTAAACCTTTTTTTTTA
TGATCATTATTAGCTTACTTTCATAATTGCGACTGGTTCCAATTGACAA
GCTTTTGATTTTAACGACTTTTAACGACAACTTGAGAAGATCAAAAAAC
AACTAATTATTCGAAACGGAATTCACGATGAGATTTCCTTCAATTTTTA
CTGCTGTTTTATTCGCAGCATCCTCCGCATTAGCTGACAAGACACATAC
TTGTCCACCATGTCCAGCTCCAGAATTGTTGGGTGGTCCATCCGTTTTC
TTGTTCCCACCAAAGCCAAAGGACACTTTGATGATCTCGAGAACTCCAG
AGGTTACATGTGTTGTTGTTGACGTTTCTCACGAGGACCCAGAGGTTAA
GTTCAACTGGTACGTTGACGGTGTTGAAGTTCACAACGCTAAGACTAAG
CCAAGAGAAGAGCAGTACAACTCCACTTACAGAGTTGTTTCCGTTTTGA
CTGTTTTGCACCAGGACTGGTTGAACGGTAAAGAATACAAGTGTAAGGT
TTCCAACAAGGCTTTGCCAGCTCCAATCGAAAAGACTATCTCCAAGGCT
AAGGGTCAACCAAGAGAGCCACAGGTTTACACTTTGCCACCATCCAGAG
AAGAGATGACTAAGAACCAGGTTTCCTTGACTTGTTTGGTTAAAGGATT
CTACCCATCCGACATTGCTGTTGAGTGGGAATCTAACGGTCAACCAGAG
AACAACTACAAGACTACTCCACCAGTTTTGGATTCTGATGGTTCCTTCT
TCTTGTACTCCAAGTTGACTGTTGACAAGTCCAGATGGCAACAGGGTAA
CGTTTTCTCCTGTTCCGTTATGCATGAGGCTTTGCACAACCACTACACT
CAAAAGTCCTTGTCTTTGTCCCCTGGTGGTGGTGTCGACCAATTCT
CTAACTCTACTTCCGCTTCCTCTACTGACGTTACTTCCTCCTCCTCTAT
TTCTACTTCCTCCGGTTCCGTTACTATTACTTCCTCTGAGGCTCCAGAA
```

```
TCTGACAACGGTACTTCTACTGCTGCTCCAACTGAAACTTCTACTGAGG
CTCCTACTACTGCTATTCCAACTAACGGAACTTCCACAGAGGCTCCAAC
AACAGCTATCCCTACAAACGGTACATCCACTGAAGCTCCTACTGACACT
ACTACAGAAGCTCCAACTACTGCTTTGCCTACTAATGGTACATCAACAG
AGGCTCCTACAGATACAACAACTGAAGCTCCAACAACTGGATTGCCAAC
AAACGGTACTACTTCTGCTTTCCCACCAACTACTTCCTTGCCACCATCC
AACACTACTACTACTCCACCATACAACCCATCCACTGACTACACTACTG
ACTACACAGTTGTTACTGAGTACACTACTTACTGTCCAGAGCCAACTAC
TTTCACAACAAACGGAAAGACTTACACTGTTACTGAGCCTACTACTTTG
ACTATCACTGACTGTCCATGTACTATCGAGAAGCCAACTACTACTTCCA
CTACAGAGTATACTGTTGTTACAGAATACACAACATATTGTCCTGAGCC
AACAACATTCACTACTAATGGAAAAACATACACAGTTACAGAACCAACT
ACATTGACAATTACAGATTGTCCTTGTACAATTGAGAAGTCCGAGGCTC
CTGAATCTTCTGTTCCAGTTACTGAATCCAAGGGTACTACTACTAAAGA
AACTGGTGTTACTACTAAGCAGACTACTGCTAACCCATCCTTGACTGTT
TCCACTGTTGTTCCAGTTTCTTCCTCTGCTTCTTCCCACTCCGTTGTTA
TCAACTCCAACGGTGCTAACGTTGTTGTTCCTGGTGCTTTGGGATTGGC
TGGTGTTGCTATGTTGTTCTTGTAATAGGGCCGGCCATTTAAATACAGG
CCCCTTTTCCTTTGTCGATATCATGTAATTAGTTATGTCACGCTTACAT
TCACGCCCTCCTCCCACATCCGCTCTAACCGAAAAGGAAGGAGTTAGAC
AACCTGAAGTCTAGGTCCCTATTTATTTTTTTTAATAGTTATGTTAGTA
TTAAGAACGTTATTTATATTTCAAATTTTTCTTTTTTTTCTGTACAAAC
GCGTGTACGCATGTAACATTATACTGAAAACCTTGCTTGAGAAGGTTTT
GGGACGCTCGAAGGCTTTAATTTGCAAGCTGGATCCGCGGCCGCTTACG
CGCCGTTCTTCGCTTGGTCTTGTATCTCCTTACACTGTATCTTCCCATT
TGCGTTTAGGTGGTTATCAAAAACTAAAAGGAAAAATTTCAGATGTTTA
TCTCTAAGGTTTTTTCTTTTTACAGTATAACACGTGATGCGTCACGTGG
TACTAGATTACGTAAGTTATTTTGGTCCGGTGGGTAAGTGGGTAAGAAT
AGAAAGCATGAAGGTTTACAAAAACGCAGTCACGAATTATTGCTACTTC
GAGCTTGGAACCACCCCAAAGATTATATTGTACTGATGCACTACCTTCT
CGATTTTGCTCCTCCAAGAACCTACGAAAAACATTTCTTGAGCCTTTTC
AACCTAGACTACACATCAAGTTATTTAAGGTATGTTCCGTTAACATGTA
AGAAAAGGAGAGGATAGATCGTTTATGGGGTACGTCGCCTGATTCAAGC
GTGACCATTCGAAGAATAGGCCTTCGAAAGCTGAATAAAGCAAATGTCA
GTTGCGATTGGTATGCTGACAAATTAGCATAAAAAGCAATAGACTTTCT
AACCACCTGTTTTTTCCTTTTACTTTATTTATATTTTGCCACCGTACT
AACAAGTTCAGACAAATTAATTAACACCATGTCAGAAGATCAAAAAGT
GAAAATTCCGTACCTTCTAAGGTTAATATGGTGAATCGCACCGATATAC
TGACTACGATCAAGTCATTGTCATGGCTTGACTTGATGTTGCCATTTAC
TATAATTCTCTCCATAATCATTGCAGTAATAATTTCTGTCTATGTGCCT
TCTTCCCGTCACACTTTTGACGCTGAAGGTCATCCCAATCTAATGGGAG
```

```
TGTCCATTCCTTTGACTGTTGGTATGATTGTAATGATGATTCCCCCGAT
CTGCAAAGTTTCCTGGGAGTCTATTCACAAGTACTTCTACAGGAGCTAT
ATAAGGAAGCAACTAGCCCTCTCGTTATTTTTGAATTGGGTCATCGGTC
CTTTGTTGATGACAGCATTGGCGTGGATGGCGCTATTCGATTATAAGGA
ATACCGTCAAGGCATTATTATGATCGGAGTAGCTAGATGCATTGCCATG
GTGCTAATTTGGAATCAGATTGCTGGAGGAGACAATGATCTCTGCGTCG
TGCTTGTTATTACAAACTCGCTTTTACAGATGGTATTATATGCACCATT
GCAGATATTTTACTGTTATGTTATTTCTCATGACCACCTGAATACTTCA
AATAGGGTATTATTCGAAGAGGTTGCAAAGTCTGTCGGAGTTTTTCTCG
GCATACCACTGGGAATTGGCATTATCATACGTTTGGGAAGTCTTACCAT
AGCTGGTAAAAGTAATTATGAAAAATACATTTTGAGATTTATTTCTCCA
TGGGCAATGATCGGATTTCATTACACTTTATTTGTTATTTTTATTAGTA
GAGGTTATCAATTTATCCACGAAATTGGTTCTGCAATATTGTGCTTTGT
CCCATTGGTGCTTTACTTCTTTATTGCATGGTTTTTGACCTTCGCATTA
ATGAGGTACTTATCAATATCTAGGAGTGATACACAAAGAGAATGTAGCT
GTGACCAAGAACTACTTTTAAAGAGGGTCTGGGGAAGAAAGTCTTGTGA
AGCTAGCTTTTCTATTACGATGACGCAATGTTTCACTATGGCTTCAAAT
AATTTTGAACTATCCCTGGCAATTGCTATTTCCTTATATGGTAACAATA
GCAAGCAAGCAATAGCTGCAACATTTGGGCCGTTGCTAGAAGTTCCAAT
TTTATTGATTTTGGCAATAGTCGCGAGAATCCTTAAACCATATTATATA
TGGAACAATAGAAATTAATTAACAGGGCCCTTTTCCTTTGTCGATATCA
TGTAATTAGTTATGTCACGCTTACATTCACGCCCTCCTCCCACATCCGC
TCTAACCGAAAAGGAAGGAGTTAGACAACCTGAAGTCTAGGTCCCTATT
TATTTTTTTAATAGTTATGTTAGTATTAAGAACGTTATTTATATTTCA
AATTTTTGTTTTTTTCTGTACAAACGCGTGTACGCATGTAACATTATA
CTGAAAACCTTGCTTGAGAAGGTTTTGGGACGCTCGAAGGCTTTAATTT
GCAAGCTGCGGCCTAAGGCGCGCCAGGCCATAATGGCCCAAATGGAAGA
GGACATTAGAAATGTGTTTGGTAAGAACATGAAGCCGGAGGCATACAAA
CGATTCACAGATTTGAAGGAGGAAAACAAACTGCATCCACCGGAAGTGC
CAGCAGCCGTGTATGCCAACCTTGCTCTCAAAGGCATTCCTAGGGATCT
GAGTGGGAAATATCTGAGATTCACAGACCCACTATTGGAACAGTACCAA
ACCTAGTTTGGCCGATCCATGATTATGTAATGCATATAGTTTTTGTCGA
TGCTCACCCGTTTCGAGTCTGTCTCGTATCGTCTTACGTATAAGTTCAA
GCATGTTTACCAGGTGTGTTAGAAACTCCTTTGTGAGGGCAGGACCTAT
TCGTCTCGGTCCCGTTGTTTCTAAGAGACTGTACAGCCAAGCGCAGAAT
GGTGGCATTAACCATAAGAGGATTCTGATCGGACTTGGTCTATTGGCTA
TTGGAACCACCCTTTACGGACAACCAACCGTACCAAGACTCCTATTGC
ATTTGTGGAACCAGCCACGGAAAGAGCGTTTAAGGACGGAGACGTCTCT
GTGATTTTTGTTCTCGGAGGTCCAGGAGCTGGAAAAGGTACCCAATGTG
CCAAACTAGTGAGTAATTACGGATTTGTTCACCTGTCAGCTGGAGACTT
GTTACGTGCAGAACAGAAGAGGGAGGGGTCTAAGTATGGAGAGATGATT
TCCCAGTATATCAGAGATGGACTGATAGTACCTCAAGAGGTGACCATTG
CGCTCTTGGAGCAGGCCATGAAGGAAAACTTCGAGAAAGGGAAGACACG
GTTCTTGATTGAIGGATTCCCTCGTAAGATGGACCAGGCCAAAACTTTT
GAGGAAAAAGTCGCAAAGTCCAAGGTGACACTTTTCTTTGATTGTCCCG
AATCAGTGCTCCTTGAGAGATTACTTAAAAGAGGACAGACAAGCGGAAG
AGAGGATGATAATGCGGAGAGTATCAAAAAAAGATTCAAAACATTCGTG
GAAACTTCGATGCCTGTGGTGGACTATTTCGGGAAGCAAGGACGCGTTT
TGAAGGTATCTTGTGACCACCCTGTGGATCAAGTGTATTCACAGGTTGT
GTCGGTGCTAAAAGAGAAGGGGATCTTTGCCGATAACGAGACGGAGAAT
AAATAAACATTGTAATAAGATTTAGACTGTGAATGTTCTATGTAATATT
TTTCGAGATACTGTATCTATCTGGTGTACCGTATCACTCTGGACTTGCA
AACTCATTGATTACTTGTGCAATGGGCAAGAAGGATAGCTCTAGAAAGA
AGAAGAAAAGGAGCCGCCTGAAGAGCTGGATCTTTCCGAGGTTGTTCC
AACTTTTGGTTATGAGGAATTTCATGTTGAGCAAGAGGAGAATCCGGTC
GATCAAGACGAACTTGACGGCCATAATGGCCTAGCTTGGCGTAATCATG
GTCATAGCTGTTTCCTGTGTGAAATTGTTATCCGCTCACAATTCCACAC
AACATACGAGCCGGAAGCATAAAGTGTAAAGCCTGGGGTGCCTAATGAG
TGAGCTAACTCACATTAATTGCGTTGCGCTCACTGCCCGCTTTCCAGTC
GGGAAACCTGTCGTGCCAGCTGCATTAATGAATCGGCCAACGCGCGGGG
AGAGGCGCTTTGCGTATTGGGCGCTCTTCCGCTTCCTCGCTCACTGACT
CGCTGCGCTCGGTCGTTCGGCTGCGGCGAGCGGTATCAGCTCACTCAAA
GGCGGTAATACGGTTATCCACAGAATCAGGGGATAACGCAGGAAAGAAC
ATGTGAGCAAAAGGCCAGCAAAAGGCCAGGAACCGTAAAAAGGCCGCGT
TGCTGGCGTTTTTCCATAGGCTCCGCCCCCCTGACGAGCATCACAAAAA
TCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCT
GCGCCTTATCCGGTAACTATCGTCTTGAGTCCAACCCCGGTAAGACACG
ACTTATCGCCACTGGCAGCAGCCACTGGTAACAGGATTAGCAGAGCGAG
GTATGTAGGCGGTGCTACAGAGTTCTTGAAGTGGTGGCCTAACTACGGC
TACACTAGAAGGACAGTATTTGGTATCTGCGCTCTGCTGAAGCCAGTTA
CCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTC
AGTGGAACGAAAACTCACGTTAAGGGATTTTGGTCATGAGATTATCAAA
AAGGATCTTCACCTAGATCCTTTTAAATTAAAAATGAAGTTTTAAATCA
ATCTAAAGTATATATGAGTAAACTTGGTCTGACAGTTACCAATGCTTAA
TCAGTGAGGCACCTATCTCAGCGATCTGTCTATTTCGTTCATCCATAGT
```

-continued

```
TGCCTGACTCCCCGTCGTGTAGATAACTACGATACGGGAGGGCTTACCA

TCTGGCCCCAGTGCTGCAATGATACCGCGAGACCCACGCTCACCGGCTC

CAGATTTATCAGCAATAAACCAGCCAGCCGGAAGGGCCGAGCGCAGAAG

TGGTCCTGCAACTTTATCCGCCTCCATCCAGTCTATTAATTGTTGCCGG

GAAGCTAGAGTAAGTAGTTCGCCAGTTAATAGTTTGCGCAACGTTGTTG

CCATTGCTACAGGCATCGTGGTGTCACGCTCGTCGTTTGGTATGGCTTC

ATTCAGCTCCGGTTCCCAACGATCAAGGCGAGTTACATGATCCCCCATG

TTGTGCAAAAAAGCGGTTAGCTCCTTCGGTCCTCCGATCGTTGTCAGAA

GTAAGTTGGCCGCAGTGTTATCACTCATGGTTATGGCAGCACTGCATAA

TTCTCTTACTGTCATGCCATCCGTAAGATGCTTTTCTGTGACTGGTGAG

TACTCAACCAAGTCATTCTGAGAATAGTGTATGCGGCGACCGAGTTGCT

CTTGCCCGGCGTCAATACGGGATAATACCGCGCCACATAGCAGAACTTT

AAAAGTGCTCATCATTGGAAAACGTTCTTCGGGGCGAAAACTCTCAAGG

ATCTTACCGCTGTTGAGATCCAGTTCGATGTAACCCACTCGTGCACCCA

ACTGATCTTCAGCATCTTTTACTTTCACCAGCGTTTCTGGGTGAGCAAA

AACAGGAAGGCAAAATGCCGCAAAAAAGGGAATAAGGGCGACACGGAAA

TGTTGAATACTCATACTCTTCCTTTTTCAATATTATTGAAGCATTTATC

AGGGTTATTGTCTCATGAGCGGATACATATTTGAATGTATTTAGAAAAA

TAAACAAATAGGGGTTCCGCGCACATTTCCCCGAAAAGTGCCACCTGAC

GTCTAAGAAACCATTATTATCATGACATTAACCTATAAAAATAGGCGTA

TCACGAGGCCCTTTCGTC
```

To test the capacity of this configuration for displaying monovalent antibody fragments (comprising human IgGs) (1 heavy chain immunoglobulin and 1 light chain immunoglobulin (H+L)) on the yeast cell wall, pGLY9008 was introduced into GFI 5.0 strains that have been selected previously as expression hosts of human anti-Her2 or anti-PCSK9 IgGs. An empty strain was included as a control (Table 1).

TABLE 1

Yeast Strains

| Strain | mAb |
| --- | --- |
| YGLY8316 | Empty |
| YGLY18483 | Anti-PCSK9 (AX189) |
| YGLY18281 | Anti-PCSK9 (AX132) |
| YGLY14755 | Anti-PCSK9 (1DG) |
| YGLY13979 | Anti-Her2 |
| YGLY14836 | Anti-Her2 |

*These *Pichia pastoris* strains form part of the present invention

The glycoengineered *Pichia pastoris* monoclonal antibody production strains in Table 1 were grown in 50 mL BMGY media until the culture optical density, at 600 nm, was 2. The cells were washed three times with 1 M sorbitol and resuspended in 1 mL 1 M sorbitol. About 1-2 micrograms of SpeI linearized pGLY9008 was mixed with these competent cells. Transformation was performed with a BioRad electroporation apparatus using the manufacturer's program specific for electroporation of nucleic acids into *Pichia pastoris*. One mL recovery media was added to the cells, which were then plated out on yeast-soytone-dextrose (YSD) media with 50 μg/mL arsenite.

Growth and Induction of Fc-Monovalent Antibody Fragment (H+L) Displaying Yeast.

Figure 3A:
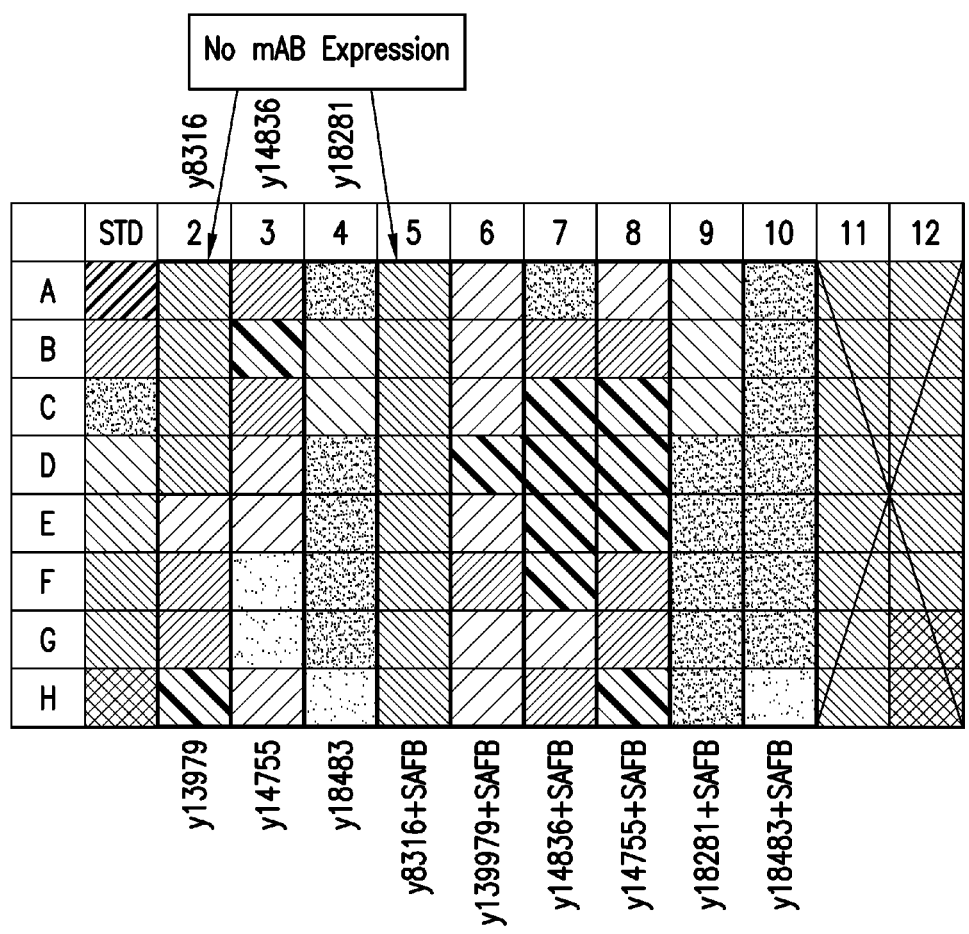
FIG. 3 (*a-c*). (a) ELISA measuring the concentration of Kappa light chain was used to determine the concentration of secreted antibodies from the strains explained in Table 1. Lane 1 was serially diluted ELISA standard; Lanes 2-3 contained material generated by strains in Table 1 without the surface anchored Fc bait (SAFE); Lanes 5-10 contained the same strains plus SAFE. Y8316 did not express antibodies and was used as a negative control. (b) Supernatants generated by the strains in 3*a* were run on Protein A columns to capture secreted antibodies. Eluted IgGs were run on (c) non-reducing SDS-PAGE.
Figure 3B:
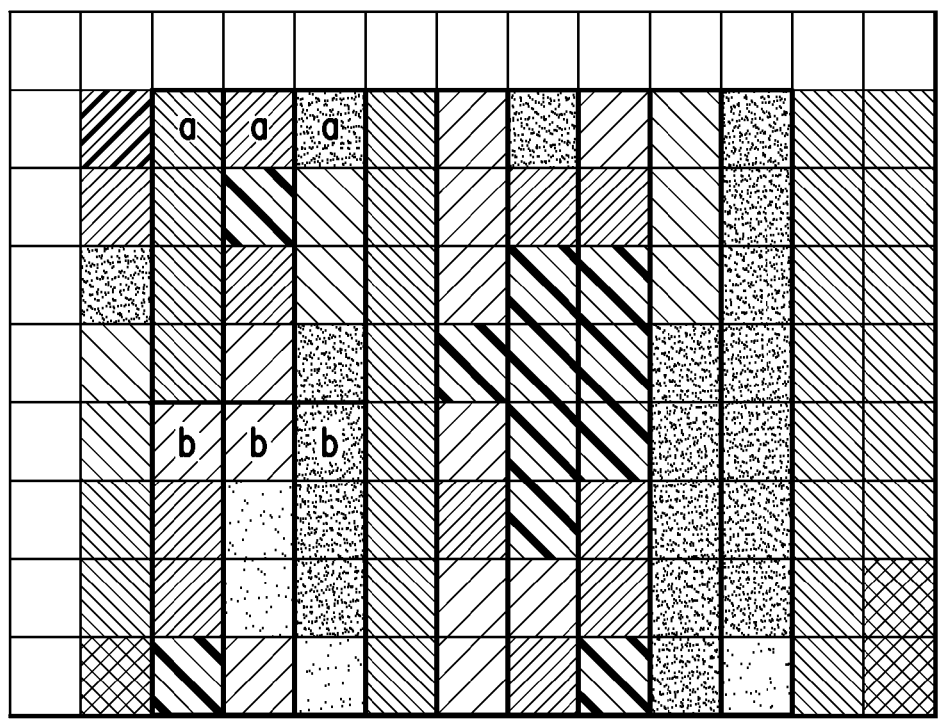
Figure 3C:
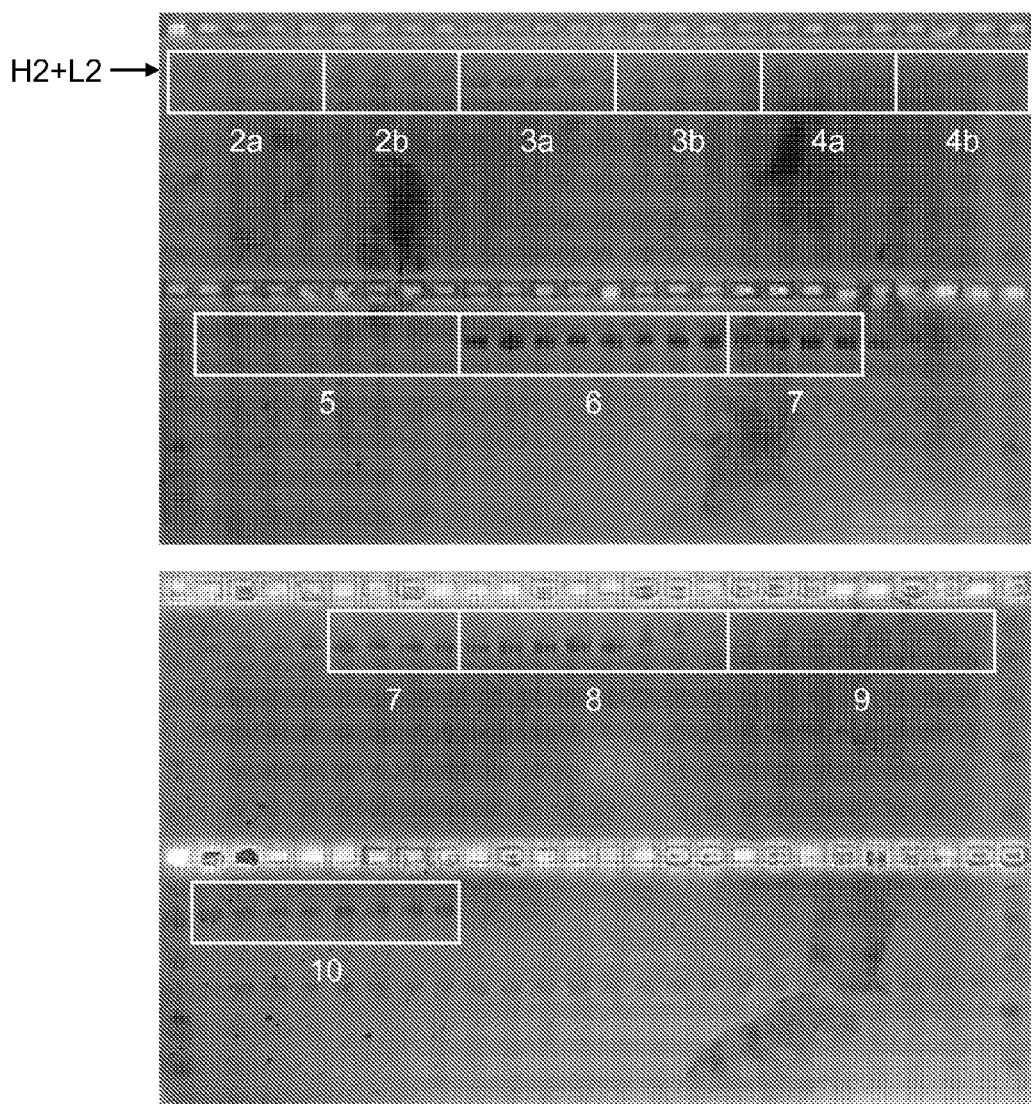

Glycoengineered yeast expressing human IgGs and the Fc-SED1 bait expression cassette were inoculated using 600 μL BMGY in a 96 deep well plate or 50 mL BMGY in a 250 mL shake flasks for two days. The cells were collected by centrifugation and the supernatant was discarded. The cells were induced by incubation in 300 μL or 25 mL BMMY with PMTi inhibitor overnight following the methods described in international application publication no. WO2007/061631. Following induction, culture supernatants were assayed for antibody expression using Kappa ELISA, according to the manufacturer's protocol, and Protein A capture SDS-PAGE analysis. The data in FIGS. 3a and b, respectively, describe the results of both of these assays. As outlined in FIG. 3, supernatants of cultures containing the Fc-Sed1 protein bait were found to contain similar levels of secreted full antibody molecules (2 heavy chain immunoglobulins and 2 light chain immunoglobulins ((H2+L2)) compared to their parent strains (containing no Fc-Sed1p). This indicated that the presence of the Fc-Sed1p bait did not interfere with the yeast ability to secret full IgG antibodies (H2+L2).

To determine the efficiency of surface displaying antibodies using this method, cells were labeled with APC 635 labeled mouse anti-Human Kappa, which detects the light chain of human antibody molecules, and were processed by flow cytometry. Briefly, each culture, after growth to an optical density, at 600 nm, of 2, was pelleted by centrifugation and washed in 100 μL PBS. Cells were incubated for 30 minutes at room temperature (RT) in 100 μL phosphate buffer saline (PBS) containing fluorescently labeled (APC635) mouse anti-human Kappa light chain and washed in 100 μl PBS. One hundred microliters of PBS was used to resuspend pellets before analyzing in a flow cytometer.

Figure 4A:
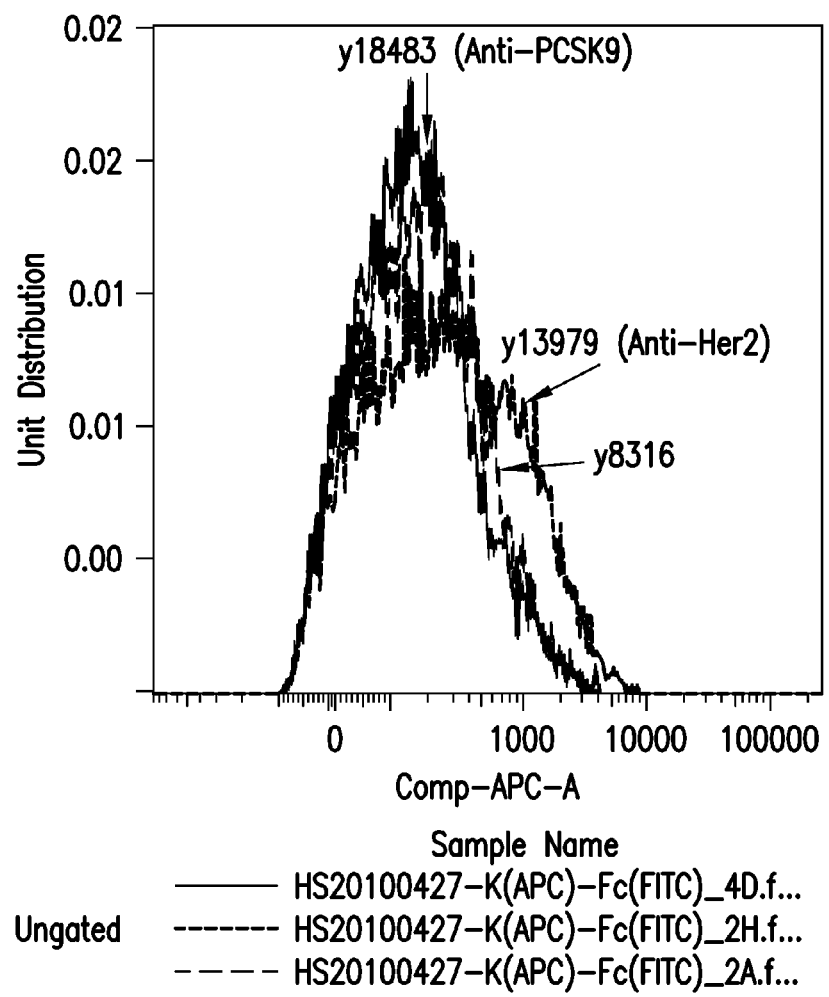
FIG. 4 (*a-c*). Figure shows FACS data demonstrating the different fluorescence intensities observed between various *Pichia pastoris* strains. (a) parental strains expressing anti-HER2 and anti-PCSK9 with no Fc-SED1 bait; (b) anti-Her2 displaying cells with and without the bait; (c) anti-PCSK9 displaying cells with and without bait.
Figure 4B:
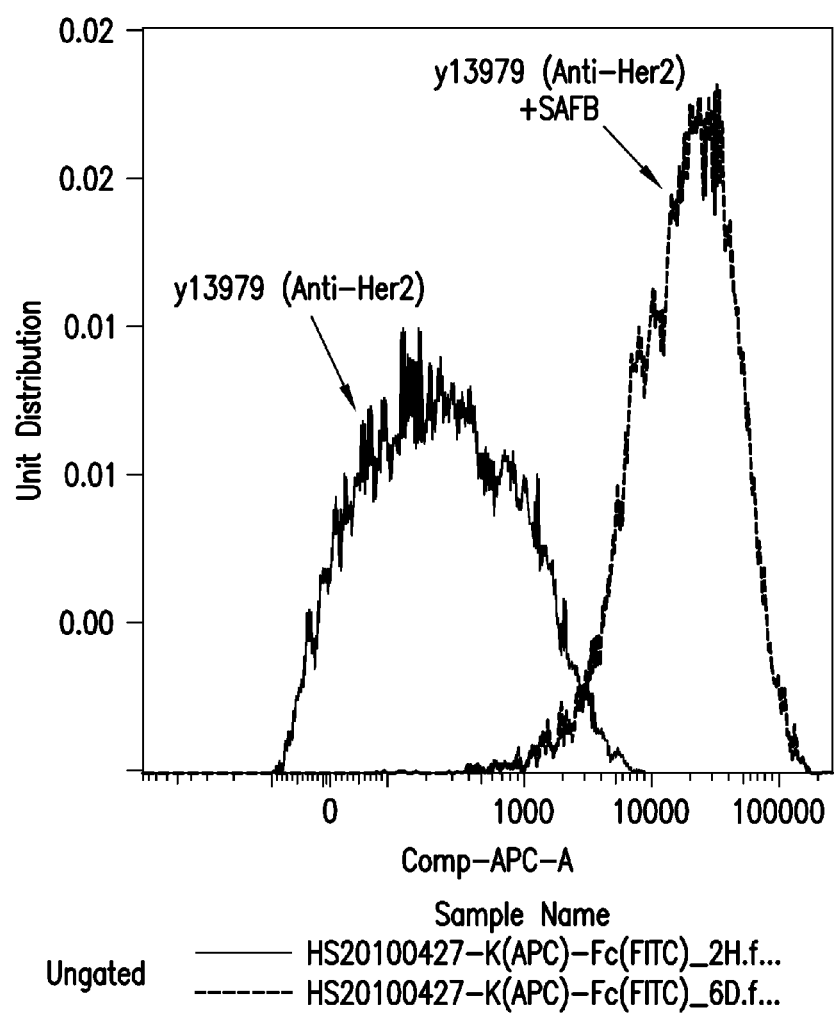
Figure 4C:
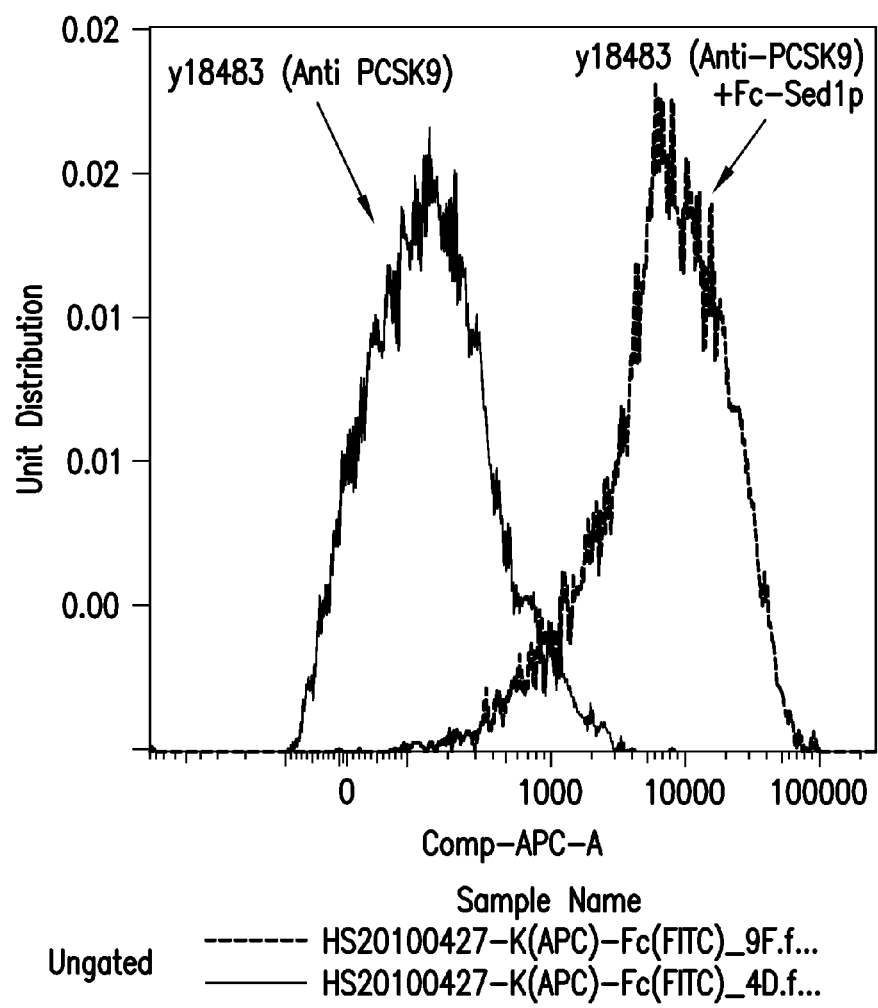

Flow cytometry analysis was conducted using the cells co-expressing Fc-Sed1p bait and anti-Her2, or Fc-Sed1p bait and anti-PCSK9. Controls were prepared in which an empty strain expressing Fc-Sed1p bait only or a strain that expressed full length antibody (H2+L2) without the Fc-Sed1p. Strains co-expressing anti-Her2 or anti-PCSK9 with the Fc-Sed1p bait were found to display significant levels of anti-Kappa binding while strains lacking the Fc-Sed1p bait showed background signal levels. In FIG. 4a-c, the fluorescent intensities from these experiments were compared. The Figure shows these different fluorescence intensities between the anti-Her2 displaying cells and the anti-PCSK9 displaying cells, and the parent strains that did not contain the Fc-Sed1p bait. It is noteworthy to mention that anti-Her2 displaying cells showed higher fluorescence intensity than the anti-PCSK9 displaying cells. These results were in congruence with what was known regarding expression levels of these two antibodies.

Figure 5:
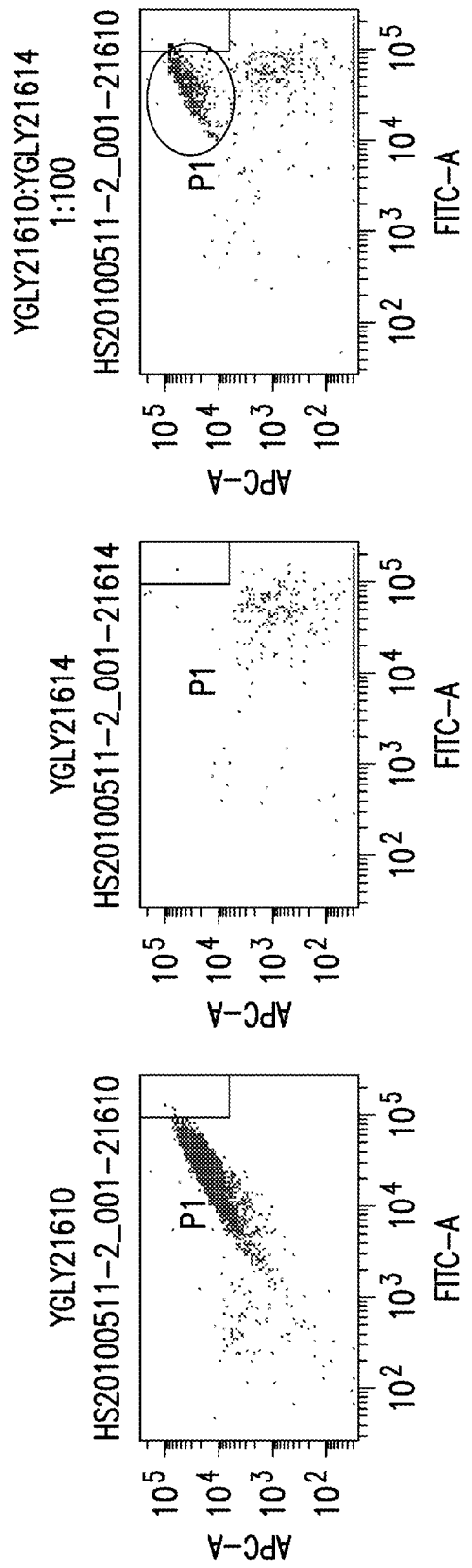
FIG. 5. FACS analysis of labeled *Pichia pastoris* yeast strains YGLY21610 and YGLY21614 displaying an Fc-Sed1p complexed with an anti-PCSK9 monovalent antibody fragment (H+L) or an anti-Her2 (H+L) monovalent antibody fragment. The cells were dually labeled with goat anti-human Fc Alexa 488, biotinylated PCSK9, and APC 635 labeled Streptavidin. The cells were analyzed separately (left and middle panels, respectively) and mixed together in a 1:00 ratio (right panel). The points representing the YGLY21610 cells in the right panel are circled.

To establish the utility of this method for separating antibody mixtures, fluorescence-activated cell sorting (FACS) of a mixture of cells displaying Fc-Sed1p anti-PCSK9 monovalent antibody fragment (H+L) (strain YGLY21610) and Fc-Sed1p anti-Her2 (H+L) (strain YGLY21614) was performed as follows. The cells displaying anti-PCSK9 (H+L) and cells displaying anti-Her2 (H+L) were mixed together in the following ratio 1:0; 0:1; and 1:100. Cells were dually labeled with goat anti-human Fc Alexa 488 and 100 nM biotinylated PCSK9 and APC 635 labeled Streptavidin. FIG. 5 shows that Fc-Sed1p/anti-PCSK9 (H+L) was able to bind biotinylated PCSK9 while Fc-Sed1p/anti-Her2 (H+L) was not. Both strains reacted with anti-human Fc Alexa 488 antibody. Two separate populations of cells were visible when cells from both cultures were mixed at a 1:100 ratio of Fc-Sed1p anti-PCSK9 displaying cells (circled) to Fc-Sed1p anti-Her2 displaying cells. The number of PCSK9 binders in this mixture was in agreement with the 1:100 ratio, thus lending further support for the robustness of this method in screening antibodies with desired antigen-binding.

The above experiments demonstrated that the Fc-Sed1p antibody display system can be used to display IgG monovalent antibody fragments (H+L) that retain specific antigen binding of their corresponding full antibody molecules (H2+L2) dimers. The next goal was to use this method to isolate and enrich for novel antibody molecules that can bind to any antigen of interest. To this end we took advantage of two recently constructed libraries. Library one was constructed by changing the sequence of the heavy chain of anti-PCSK9 antibody AX189 while marinating the original light chain sequence. This library had a diversity of about 2500 unique sequences and will be referred to as "BP550". The second library was generated by maintaining the original AX189 heavy chain sequence and changing the light chain sequence. This library contained about 4000 unique sequences and will be referred to as "BP551".

BP550 and BP551 were transformed as described previously into strain YGLY21605 (empty 5.0 strain carrying pGLY9008-expressing Fc-Sed1p) and plated out on YSD containing 300 micrograms per milliliter zeocin. Approximately, 50,000 colonies were obtained for each transformation, thus providing ample statistical coverage of all possible sequences in the libraries. The colonies resulting from transforming the two libraries were scraped off the solid media and inoculated separately in 250 mL shake flasks containing 50 mL of YSG liquid medium with 300 μ/mL zeocin. The cultures were passaged 3 times by re-inoculating 1 mL of each culture into the fresh selective liquid media (YSG+zeocin). The third passages were allowed to grow to saturation in YSG media and induced in 25 mL BMMY with PMTi inhibitor (PMTi4: L000001772; at a concentration of 1 micrograms/ml) overnight following the methods described in international patent publication no. WO2007/061631. Strains YGLY21610 (Fc-Sed1p anti-PCSK9 (AX189)) and YGLY21614 (Fc-Sed1p anti-Her2) were included as positive and negative controls, respectively.

After 24 hours of induction, each of the four cultures were grown to an optical density, at 600 nm, of 2. Pellets were collected by centrifugation and washed with 100 μL 1×PBS then labeled in 100 μL PBS containing anti-Kappa Alexa 488 and 100 nM of biotin-PCSK9. Mixtures were incubated at room temperature for 30 minutes then washed with 100 μL PBS solution. Cells were incubated at room temperature with APC 635 labeled Streptavidin in 100 μL PBS for 10 minutes and washed 2× in PBS and submitted for FACS.

Using the flow cytometer dot plots generated with YGLY21610 and YGLY21614 as boundaries to gate potential binders, clones from 100,000 cells of populations of both libraries, BP550 and BP551, were sorted in a FACS sorter and collected in 5 mL YSG media. Cultures were allowed to recover by shaking at room temperature for 5 days. Sorting round 1 pools were re-inoculated in 50 mL YSG liquid media and the same process was repeated to induce and label the cultures. Another round of sorting (round 2) was conducted on the round 1 pool and cells were collected as above and induced. To obtain single colonies, 1000 cells of both two-round sorted populations (BP550 and BP551) were plated out of solid media and were analyzed by Kappa ELISA and PCSK9 affinity ELISA to determine protein titer and binding affinities for PCSK9, respectively. Additionally, a yeast colony PCR amplification reaction was performed to amplify heavy chain and light chain genes of the round 2 clones which were submitted for DNA sequence analysis.

Figure 6:
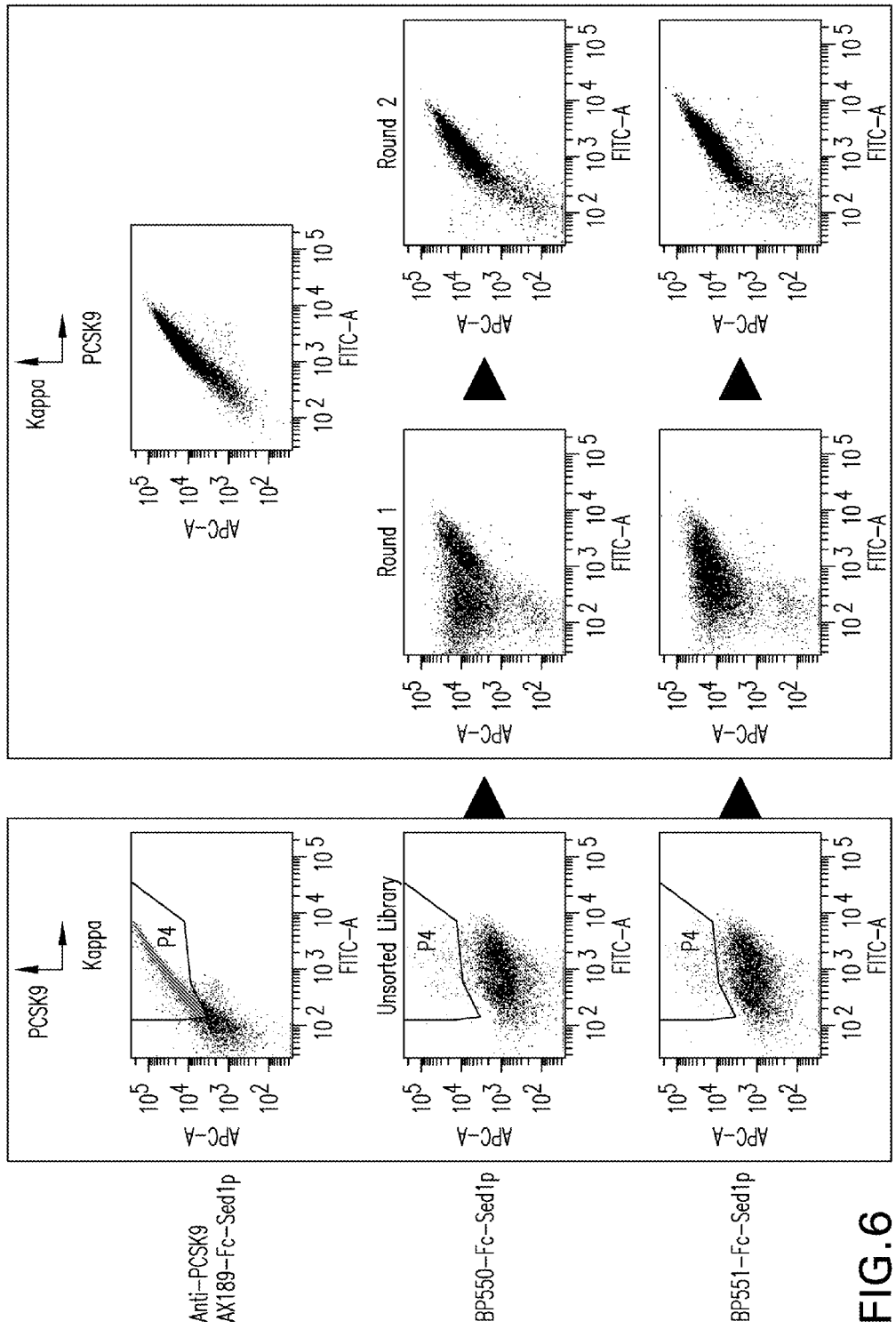
FIG. 6. FACS analysis of *Pichia pastoris* cells expressing the Fc-SED1 bait and; (1) anti-PCSK9 antibody AX189 heavy and light chains (Anti-PCSK9; AX189-Fc-Sed1p); or (2) AX189 light chain and heavy chain from the BP550 library (BP550-Fc-Sed1p); or (3) AX189 heavy chain and light chain from the BP551 library (BP551-Fc-Sed1p). The left panel shows data relating to unsorted strains containing the library, and the right panel shows data relating to cells containing the library that were sorted once or twice. FACS data relating to the control AX189 expressing cells are also shown.
Figure 8:
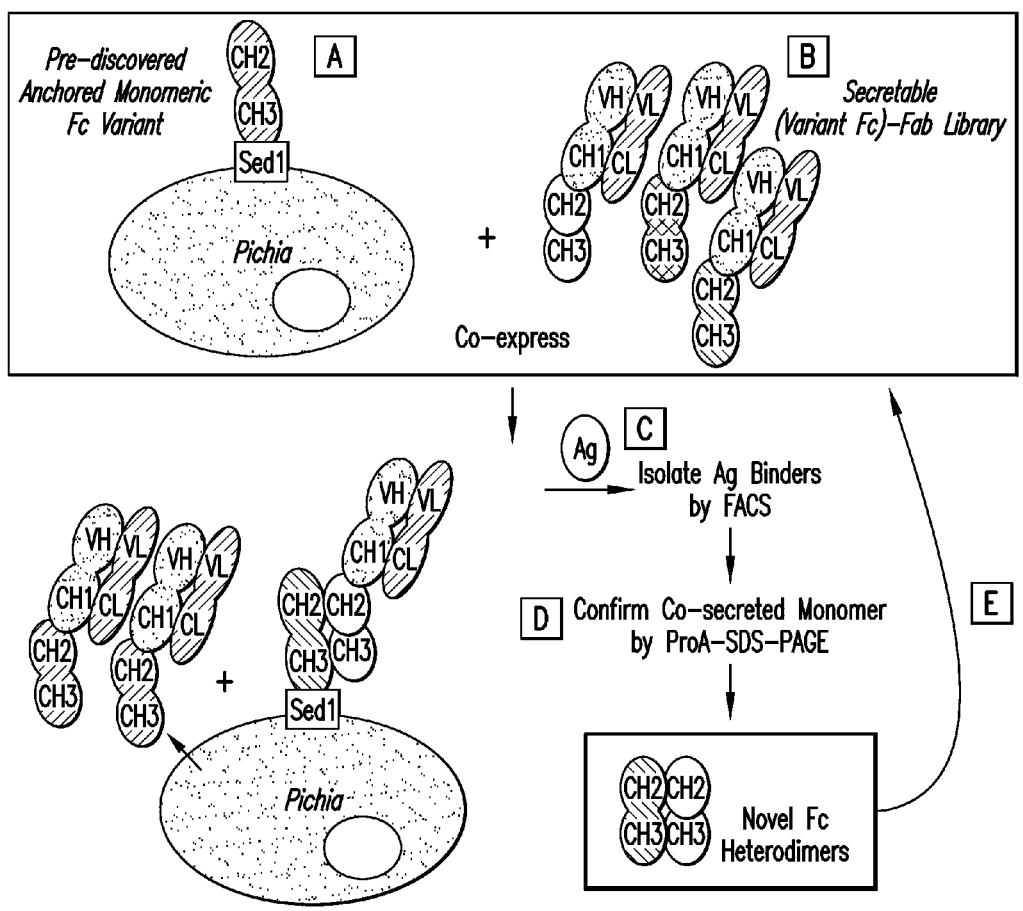
FIG. 8. The use of Fc-Sed1p display to discover novel heterodimeric Fc fragments for use in bispecifics and other applications. In this approach, an Fc mutant that lost its ability to homodimerize with self or heterodimerize with wild-type. Fc can be displayed on a cell surface (A) and co-expressed with a library of H+L mutations where Fab region remains constant but CH2 and/or CH3 domains are mutated (B). Using surface display binding to Fab, cells that are positive for antigen binding can be isolated using FACS (C). Those cells will contain novel Fc variants that restore dimerization to the displayed bait-Fc. The culture supernatants can be assayed by SDS-PAGE to ensure monomeric secretion H+L, containing the novel Fc (D). This exercise will result in identification of novel heterodimeric Fc pairs or partners that can be subject to subsequent engineering using the same assay (E).

As shown in FIG. 6, two rounds of sorting using biotinylated PCSK9 antigen resulted in significant enrichment of specific PCSK9 binders. The PCSK9 ELISA compared presorted library to round 2 sorted pools for both BP550 and BP551 (FIG. 7). Round 2 sorted pools from both libraries contained a high percentage of binders over the presorted populations. DNA sequencing confirmed the enrichment for new anti-PCSK9 binding sequences.

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:
1. An antibody display system comprising an isolated host cell wherein the host cell is selected from the group consisting of a *Pichia* cell, a Chinese hamster ovary (CHO) cell and a *Saccharomyces cerevisiae* cell; wherein said isolated host cell comprises
- (a) a polynucleotide encoding a bait comprising a heavy Fc immunoglobulin domain fused to a surface anchor polypeptide operably associated with a regulatable promotor;
- (b) one or more polynucleotides encoding an immunoglobulin light chain variable region; and
- (c) one or more polynucleotides encoding an immunoglobulin heavy chain variable region wherein the heavy chain is VH—CH1-CH2-CH3.

2. The antibody display system of claim 1 further comprising
- (i) a non-tethered full antibody comprising said immunoglobulin light and heavy chains; and/or
- (ii) a monovalent antibody fragment which is complexed with the Fc moiety of the bait.

3. The antibody display system of claim 1 wherein said one or more polynucleotides encoding an immunoglobulin light chain variable region is from a genetically diverse population of immunoglobulin light chain variable regions; and/or, wherein said one or more polynucleotides encoding the immunoglobulin heavy chain variable region is from a genetically diverse population of immunoglobulin heavy chain variable regions.

4. A method for determining if an antibody specifically binds to an antigen comprising contacting the antibody display system of claim 1 with said antigen; wherein the antibody display system comprises an isolated host cell wherein the host cell is selected from the group consisting of a *Pichia* cell, a Chinese hamster ovary (CHO) cell and a *Saccharomyces cerevisiae* cell; wherein said isolated host cell comprises
- (a) a polynucleotide encoding a bait comprising a heavy Fc immunoglobulin domain fused to a surface anchor polypeptide operably associated with a regulatable promotor;
- (b) one or more polynucleotides encoding an immunoglobulin light chain variable region; and
- (c) one or more polynucleotides encoding an immunoglobulin heavy chain variable region wherein the heavy chain is VH—CH1-CH2-CH3;
- comprising including expression from the regulatable promoter in said host cell; wherein in said isolated host cell the Fc of said bait complexes with an Fc/antigen-binding fragment comprising said immunoglobulin heavy and immunoglobulin light chains on the surface of the host cell; and
- determining if said Fc/antigen-binding fragment specifically binds to said antigen; wherein the antibody is determined to specifically bind said antigen if the monovalent antibody fragment specifically binds to said antigen and inhibiting expression of the bait from the regulatable promotor.

5. A method for identifying:
- (i) an antibody that binds specifically to an antigen; or
- (ii) a polynucleotide encoding an immunoglobulin heavy chain of said antibody and/or a polynucleotide encoding an immunoglobulin light chain of said antibody; comprising contacting the antibody display system of claim 1 with said antigen wherein the antibody display system comprises an isolated host cell wherein the host cell is selected from the group consisting of a *Pichia* cell, a Chinese hamster ovary (CHO) cell and a *Saccharomyces cerevisiae* cell; wherein said isolated host cell comprises
- (a) a polynucleotide encoding a bait comprising a heavy Fc immunoglobulin domain fused to a surface anchor polypeptide operably associated with a regulatable promotor;
- (b) one or more polynucleotides encoding an immunoglobulin light chain variable region; and
- (c) one or more polynucleotides encoding an immunoglobulin heavy chain variable region wherein the heavy chain is VH—CH1-CH2-CH3;
- comprising including expression from the regulatable promoter in said host cell; wherein in said isolated host cell the Fc of said bait complexes with an Fc/antigen-binding fragment comprising said immunoglobulin heavy and immunoglobulin light chains on the surface of the host cell; and determining if said Fc/antigen-binding fragment specifically binds to said antigen; wherein the antibody or polynucleotide is identified if said specific binding to said antigen is observed and inhibiting expression of the bait from the regulatable promotor.

6. The method of claim 4 further comprising isolating the identified polynucleotides.

7. The method of claim 4 further comprising determining the affinity of said identified antibody for said antigen.

8. The method of claim 4 further comprising recombinantly expressing the immunoglobulin chains encoded by the polynucleotides and, optionally, isolating an antibody or antigen-binding fragment thereof comprising said immunoglobulins and, optionally, producing a pharmaceutical formulation comprising combining said antibody or antigen-binding fragment thereof and a pharmaceutically acceptable carrier.

9. A method for making an antibody display system comprising an isolated host cell wherein the host cell is selected from the group consisting of a *Pichia* cell, a Chinese hamster ovary (CHO) cell and a *Saccharomyces cerevisiae* cell; wherein said isolated host cell comprises
- (a) a polynucleotide encoding a bait comprising a heavy Fc immunoglobulin domain fused to a surface anchor polypeptide operably associated with a regulatable promotor;
- (b) one or more polynucleotides encoding an immunoglobulin light chain variable region; and
- (c) one or more polynucleotides encoding an immunoglobulin heavy chain variable region wherein the heavy chain is VH—CH1-CH2-CH3;
- comprising introducing, into said isolated host cell, a polynucleotide encoding said bait, said one or more polynucleotides encoding an immunoglobulin light chain variable region; and said one or more polynucleotides encoding an immunoglobulin heavy chain variable region.

10. A method for making an antibody comprising introducing, into an isolated host cell wherein the host cell is selected from the group consisting of a *Pichia* cell, a Chinese hamster ovary (CHO) cell and a *Saccharomyces cerevisiae* cell
- (a) a polynucleotide encoding a bait comprising a heavy Fc immunoglobulin domain fused to a surface anchor polypeptide operably associated with a regulatable promotor;
- (b) one or more polynucleotides encoding an immunoglobulin light chain variable region; and
- (c) one or more polynucleotides encoding an immunoglobulin heavy chain variable region wherein the heavy chain is VH—CH1-CH2-CH3;
- and culturing the host cell under condition whereby the polynucleotides encoding the immunoglobulin chains and bait are expressed and an antibody is formed from said immunoglobulin chains; wherein said bait is operably associated with a regulatable promoter and inhibiting expression of the bait when said immunoglobulin chains are expressed.

11. A method for making an antibody comprising culturing an isolated host cell in a growth medium under conditions allowing expression of a bait, an immunoglobulin light chain and an immunoglobulin heavy chain of said antibody; wherein the host cell is selected from the group consisting of a *Pichia* cell, a Chinese hamster ovary (CHO) cell and a *Saccharomyces cerevisiae* cell; wherein said isolated host cell comprises
  (a) a polynucleotide encoding a bait comprising a heavy Fc immunoglobulin domain fused to a surface anchor polypeptide operably associated with a regulatable promotor;
  (b) one or more polynucleotides encoding an immunoglobulin light chain variable region; and
  (c) one or more polynucleotides encoding an immunoglobulin heavy chain variable region wherein the heavy chain is VH—CH1-CH2-CH3;
  wherein the Fc of said bait complexes with an Fc/antigen-binding fragment comprising said immunoglobulin heavy and immunoglobulin light chains on the surface of the host cell; and then inhibiting expression of the bait; wherein said antibody is secreted from said isolated host cell when bait expression is inhibited; optionally comprising isolating said antibody from said eukaryotic host cell and medium.

12. A method for determining the effect of a sugar on an antibody which specifically binds to an antigen comprising contacting the antibody display system of claim 1 with said antigen; wherein the antibody display system comprises an isolated host cell wherein the host cell is selected from the group consisting of a *Pichia* cell, a Chinese hamster ovary (CHO) cell and a *Saccharomyces cerevisiae* cell; wherein said isolated host cell comprises
  (a) a polynucleotide encoding a bait comprising a heavy Fc immunoglobulin domain fused to a surface anchor polypeptide operably associated with a regulatable promotor;
  (b) one or more polynucleotides encoding an immunoglobulin light chain variable region; and
  (c) one or more polynucleotides encoding an immunoglobulin heavy chain variable region wherein the heavy chain is VH—CH1-CH2-CH3;
  comprising including expression of said regulatable promoter;
  wherein the Fc of said bait complexes with an Fc/antigen-binding fragment comprising said immunoglobulin heavy and immunoglobulin light chains on the surface of the host cell; wherein said heavy or light chain comprises said sugar; determining if said Fc/antigen-binding fragment specifically binds to said antigen; determining the binding affinity of the antibody comprising said sugar for the antigen; and comparing the affinity of the antibody with affinity of an otherwise identical antibody which lacks said sugar; wherein the sugar is determined to increase affinity for the antigen if the affinity of the antibody comprising said sugar is higher than the affinity of the antibody which lacks the sugar, and/or wherein the sugar is determined to decrease affinity for the antigen if the affinity of antibody comprising said sugar is lower than the affinity of the antibody which lacks the sugar; and inhibiting expression of the bait from the regulatable promotor.

13. The antibody display system of claim 1 wherein the host cell is *Pichia*.

14. The antibody display system of claim 13 wherein the host cell is *Pichia pastoris*.

15. The antibody display system of claim 1 wherein the host cell is *S. cerevisiae*.

16. The antibody display system of claim 1 wherein the host cell is Chinese hamster ovary.

17. The method of claim 14 wherein the host cell is *Pichia*.

18. The method of claim 17 wherein the host cell is *Pichia pastoris*.

19. The method of claim 14 wherein the host cell is *S. cerevisiae*.

20. The method of claim 14 wherein the host cell is Chinese hamster ovary.

21. The method of claim 5 wherein the host cell is *Pichia*.

22. The method of claim 21 wherein the host cell is *Pichia pastoris*.

23. The method of claim 5 wherein the host cell is *S. cerevisiae*.

24. The method of claim 5 wherein the host cell is Chinese hamster ovary.

25. The method of claim 9 wherein the host cell is *Pichia*.

26. The method of claim 25 wherein the host cell is *Pichia pastoris*.

27. The method of claim 9 wherein the host cell is *S. cerevisiae*.

28. The method of claim 9 wherein the host cell is Chinese hamster ovary.

29. The method of claim 10 wherein the host cell is *Pichia*.

30. The method of claim 29 wherein the host cell is *Pichia pastoris*.

31. The method of claim 10 wherein the host cell is *S. cerevisiae*.

32. The method of claim 10 wherein the host cell is Chinese hamster ovary.

33. The method of claim 11 wherein the host cell is *Pichia*.

34. The method of claim 33 wherein the host cell is *Pichia pastoris*.

35. The method of claim 11 wherein the host cell is *S. cerevisiae*.

36. The method of claim 11 wherein the host cell is Chinese hamster ovary.

37. The method of claim 12 wherein the host cell is *Pichia*.

38. The method of claim 37 wherein the host cell is *Pichia pastoris*.

39. The method of claim 12 wherein the host cell is *S. cerevisiae*.

40. The method of claim 12 wherein the host cell is Chinese hamster ovary.

* * * * *

SEQUENCE LISTING

```
<160> NUMBER OF SEQ ID NOS: 6

<210> SEQ ID NO 1
<211> LENGTH: 226
<212> TYPE: PRT
<213> ORGANISM: Homo sapiens

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

```
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 2
<211> LENGTH: 322
<212> TYPE: PRT
<213> ORGANISM: Saccharomyces cerevisiae

<400> SEQUENCE: 2

Val Asp Gln Phe Ser Asn Ser Thr Ser Ala Ser Ser Thr Asp Val Thr
  1               5                  10                  15

Ser Ser Ser Ser Ile Ser Thr Ser Ser Gly Ser Val Thr Ile Thr Ser
             20                  25                  30

Ser Glu Ala Pro Glu Ser Asp Asn Gly Thr Ser Thr Ala Ala Pro Thr
         35                  40                  45

Glu Thr Ser Thr Glu Ala Pro Thr Thr Ala Ile Pro Thr Asn Gly Thr
 50                  55                  60

Ser Thr Glu Ala Pro Thr Thr Ala Ile Pro Thr Asn Gly Thr Ser Thr
 65                  70                  75                  80

Glu Ala Pro Thr Asp Thr Thr Glu Ala Pro Thr Thr Ala Leu Pro Thr
                 85                  90                  95

Asn Gly Thr Ser Thr Glu Ala Pro Thr Asp Thr Thr Glu Ala Pro Thr
            100                 105                 110

Pro Thr Gly Leu Pro Thr Asn Gly Thr Thr Ser Ala Phe Pro Pro Thr
        115                 120                 125

Thr Thr Ser Leu Pro Pro Ser Asn Thr Thr Thr Pro Pro Tyr Asn Pro
    130                 135                 140

Ser Thr Asp Tyr Thr Thr Asp Tyr Thr Val Val Thr Glu Tyr Thr Thr
145                 150                 155                 160

Tyr Cys Pro Glu Pro Thr Thr Phe Thr Thr Asn Gly Lys Thr Tyr Thr
                165                 170                 175

Val Thr Glu Pro Thr Thr Leu Thr Ile Thr Asp Cys Pro Cys Thr Ile
            180                 185                 190

Glu Lys Pro Thr Thr Thr Ser Thr Thr Glu Tyr Thr Val Val Thr Glu
        195                 200                 205
```

```
Glu Tyr Thr Thr Tyr Cys Pro Glu Pro Thr Thr Phe Thr Thr Asn Gly
            210                 215                 220

Lys Thr Tyr Thr Val Thr Glu Pro Thr Thr Leu Thr Ile Thr Asp Cys
225                 230                 235                 240

Pro Cys Thr Ile Glu Lys Ser Glu Ala Pro Glu Ser Ser Val Pro Val
                245                 250                 255

Thr Glu Ser Lys Gly Thr Thr Lys Glu Thr Gly Val Thr Thr Lys
            260                 265                 270

Gln Thr Thr Ala Asn Pro Ser Leu Thr Val Ser Thr Val Pro Val
        275                 280                 285

Ser Ser Ser Ala Ser Ser His Ser Val Val Ile Asn Ser Asn Gly Ala
        290                 295                 300

Asn Val Val Pro Gly Ala Leu Gly Leu Ala Gly Val Ala Met Leu
305                 310                 315                 320

Phe Leu

<210> SEQ ID NO 3
<211> LENGTH: 19
<212> TYPE: PRT
<213> ORGANISM: Homo sapiens

<400> SEQUENCE: 3

Met Arg Phe Pro Ser Ile Phe Thr Ala Val Leu Phe Ala Ala Ser Ser
1               5                   10                  15

Ala Leu Ala

<210> SEQ ID NO 4
<211> LENGTH: 570
<212> TYPE: PRT
<213> ORGANISM: Artificial Sequence
<220> FEATURE:
<223> OTHER INFORMATION: Homo sapiens and Saccharmomyces cerevisiae

<400> SEQUENCE: 4

Met Arg Phe Pro Ser Ile Phe Thr Ala Val Leu Phe Ala Ala Ser Ser
1               5                   10                  15

Ala Leu Ala Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Glu Glu Met Thr Lys Asn
145                 150                 155                 160

Gln Val Ser Leu Thr Cys Leu Val Lys Gly Phe Tyr Pro Ser Asp Ile
                165                 170                 175
```

```
Ala Val Glu Trp Glu Ser Asn Gly Gln Pro Glu Asn Tyr Lys Thr
                180                 185                 190

Thr Pro Pro Val Leu Asp Ser Asp Gly Ser Phe Phe Leu Tyr Ser Lys
            195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Gly Gly Val Asp Gln Phe Ser Asn Ser Thr
            245                 250                 255

Ser Ala Ser Ser Thr Asp Val Thr Ser Ser Ser Ile Ser Thr Ser
            260                 265                 270

Ser Gly Ser Val Thr Ile Thr Ser Ser Glu Ala Pro Glu Ser Asp Asn
            275                 280                 285

Gly Thr Ser Thr Ala Ala Pro Thr Glu Thr Ser Thr Glu Ala Pro Thr
    290                 295                 300

Thr Ala Ile Pro Thr Asn Gly Thr Ser Thr Glu Ala Pro Thr Thr Ala
305                 310                 315                 320

Ile Pro Thr Asn Gly Thr Ser Thr Glu Ala Pro Thr Asp Thr Thr Thr
            325                 330                 335

Glu Ala Pro Thr Thr Ala Leu Pro Thr Asn Gly Thr Ser Thr Glu Ala
                340                 345                 350

Pro Thr Asp Thr Thr Thr Glu Ala Pro Thr Thr Gly Leu Pro Thr Asn
    355                 360                 365

Gly Thr Thr Ser Ala Phe Pro Pro Thr Thr Ser Leu Pro Pro Ser Asn
    370                 375                 380

Thr Thr Thr Thr Pro Pro Tyr Asn Pro Ser Thr Asp Tyr Thr Thr Asp
385                 390                 395                 400

Tyr Thr Val Val Thr Glu Tyr Thr Thr Tyr Cys Pro Glu Pro Thr Thr
                405                 410                 415

Phe Thr Thr Asn Gly Lys Thr Tyr Thr Val Thr Glu Pro Thr Thr Leu
            420                 425                 430

Thr Ile Thr Asp Cys Pro Cys Thr Ile Glu Lys Pro Thr Thr Thr Ser
            435                 440                 445

Thr Thr Glu Tyr Thr Val Val Thr Glu Tyr Thr Thr Tyr Cys Pro Glu
    450                 455                 460

Pro Thr Thr Phe Thr Thr Asn Gly Lys Thr Tyr Thr Val Thr Glu Pro
465                 470                 475                 480

Thr Thr Leu Thr Ile Thr Asp Cys Pro Cys Thr Ile Glu Lys Ser Glu
            485                 490                 495

Ala Pro Glu Ser Ser Val Pro Val Thr Glu Ser Lys Gly Thr Thr Thr
            500                 505                 510

Lys Glu Thr Gly Val Thr Thr Lys Gln Thr Thr Ala Asn Pro Ser Leu
            515                 520                 525

Thr Val Ser Thr Val Val Pro Val Ser Ser Ala Ser Ser His Ser
            530                 535                 540

Val Val Ile Asn Ser Asn Gly Ala Asn Val Val Pro Gly Ala Leu
545                 550                 555                 560

Gly Leu Ala Gly Val Ala Met Leu Phe Leu
                565                 570

<210> SEQ ID NO 5
<211> LENGTH: 8640
```

<212> TYPE: DNA
<213> ORGANISM: Artificial Sequence
<220> FEATURE:
<223> OTHER INFORMATION: Plasmid pGLY3033

<400> SEQUENCE: 5

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg  cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt gagatctaac atccaaagac     420
gaaaggttga atgaaacctt tttgccatcc gacatccaca ggtccattct cacacataag     480
tgccaaacgc aacaggaggg gatacactag cagcagaccg ttgcaaacgc aggacctcca     540
ctcctcttct cctcaacacc cacttttgcc atcgaaaaac cagcccagtt attgggcttg     600
attggagctc gctcattcca attccttcta ttaggctact aacaccatga ctttattagc     660
ctgtctatcc tggcccccct ggcgaggttc atgtttgttt atttccgaat gcaacaagct     720
ccgcattaca cccgaacatc actccagatg agggctttct gagtgtgggg tcaaatagtt     780
tcatgttccc caaatggccc aaaactgaca gtttaaacgc tgtcttggaa cctaatatga     840
caaaagcgtg atctcatcca agatgaacta agtttggttc gttgaaatgc taacggccag     900
ttggtcaaaa agaaacttcc aaaagtcggc ataccgtttg tcttgtttgg tattgattga     960
cgaatgctca aaaataatct cattaatgct tagcgcagtc tctctatcgc ttctgaaccc    1020
cggtgcacct gtgccgaaac gcaaatgggg aaacaccgc  ttttttggatg attatgcatt    1080
gtctccacat tgtatgcttc caagattctg gtgggaatac tgctgatagc ctaacgttca    1140
tgatcaaaat ttaactgttc taaccccctac ttgacagcaa tatataaaca gaaggaagct    1200
gccctgtctt aaacctttt  ttttatcatc attattagct tactttcata attgcgactg    1260
gttccaattg acaagctttt gattttaacg acttttaacg acaacttgag aagatcaaaa    1320
acaactaat  tattcgaaac ggaattcacg atggtcgctt ggtggtcttt gtttctgtac    1380
ggtcttcagg tcgctgcacc tgcttttggct acttccagat tggagggatt gcaatccgaa    1440
aaccacagat tgagaatgaa gatcactgag ttggacaagg acttggagga agttactatg    1500
cagttgcagg atgttggtgg ttgtgagcag aagttgatct ccgaagagga tttggtcgac    1560
caattctcta actctacttc cgcttcctct actgacgtta cttcctcctc ctctatttct    1620
acttcctccg gttccgttac tattacttcc tctgaggctc cagaatctga caacggtact    1680
tctactgctg ctccaactga aacttctact gaggctccta ctactgctat tccaactaac    1740
ggaacttcca cagaggctcc aacaacagct atccctacaa acgtacatc  cactgaagct    1800
cctactgaca ctactacaga agctccaact actgctttgc ctactaatgg tacatcaaca    1860
gaggctccta cagatacaac aactgaagct ccaacaactg gattgccaac aaacggtact    1920
acttctgctt tcccaccaac tacttccttg ccaccatcca acactactac tactccacca    1980
tacaacccat ccactgacta cactactgac tacacagttg ttactgagta cactacttac    2040
tgtccagagc caactacttt cacaacaaac ggaaagactt acactgttac tgagcctact    2100
actttgacta tcactgactg tccatgtact atcgagaagc caactactac ttccactaca    2160
```

```
gagtatactg ttgttacaga atacacaaca tattgtcctg agccaacaac attcactact    2220
aatggaaaaa catacacagt tacagaacca actacattga caattacaga ttgtccttgt    2280
acaattgaga agtccgaggc tcctgaatct tctgttccag ttactgaatc caagggtact    2340
actactaaag aaactggtgt tactactaag cagactactg ctaacccatc cttgactgtt    2400
tccactgttg ttccagtttc ttcctctgct tcttcccact ccgttgttat caactccaac    2460
ggtgctaacg ttgttgttcc tggtgctttg ggattggctg gtgttgctat gttgttcttg    2520
taatagggcc ggccatttaa atacaggccc cttttccttt gtcgatatca tgtaattagt    2580
tatgtcacgc ttacattcac gccctcctcc cacatccgct ctaaccgaaa aggaaggagt    2640
tagacaacct gaagtctagg tccctattta ttttttttaa tagttatgtt agtattaaga    2700
acgttattta tatttcaaat ttttcttttt tttctgtaca aacgcgtgta cgcatgtaac    2760
attatactga aaaccttgct tgagaaggtt ttgggacgct cgaaggcttt aatttgcaag    2820
ctggatccgc ggccgcttac gcgccgttct tcgcttggtc ttgtatctcc ttacactgta    2880
tcttcccatt tgcgtttagg tggttatcaa aaactaaaag gaaaaatttc agatgtttat    2940
ctctaaggtt ttttcttttt acagtataac acgtgatgcg tcacgtggta ctagattacg    3000
taagttattt tggtccggtg ggtaagtggg taagaataga aagcatgaag gtttacaaaa    3060
acgcagtcac gaattattgc tacttcgagc ttggaaccac cccaaagatt atattgtact    3120
gatgcactac cttctcgatt tgctcctcc aagaacctac gaaaaacatt tcttgagcct    3180
tttcaaccta gactacacat caagttattt aaggtatgtt ccgttaacat gtaagaaaag    3240
gagaggatag atcgtttatg gggtacgtcg cctgattcaa gcgtgaccat tcgaagaata    3300
ggccttcgaa agctgaataa agcaaatgtc agttgcgatt ggtatgctga caaattagca    3360
taaaaagcaa tagactttct aaccaccgtt ttttttcctt ttactttatt tatattttgc    3420
caccgtacta acaagttcag acaaattaat taacaccatg tcagaagatc aaaaaagtga    3480
aaattccgta ccttctaagg ttaatatggt gaatcgcacc gatatactga ctacgatcaa    3540
gtcattgtca tggcttgact tgatgttgcc atttactata attctctcca taatcattgc    3600
agtaataatt tctgtctatg tgccttcttc ccgtcacact tttgacgctg aaggtcatcc    3660
caatctaatg ggagtgtcca ttccttttgac tgttggtatg attgtaatga tgattccccc    3720
gatctgcaaa gttcctggg agtctattca caagtacttc tacaggagct atataaggaa    3780
gcaactagcc ctctcgttat ttttgaattg ggtcatcggt cctttgttga tgacagcatt    3840
ggcgtggatg cgctattcg attataagga ataccgtcaa ggcattatta tgatcggagt    3900
agctagatgc attgccatgg tgctaatttg gaatcagatt gctggaggag acaatgatct    3960
ctgcgtcgtg cttgttatta caaactcgct tttacagatg gtattatatg caccattgca    4020
gatattttac tgttatgtta tttctcatga ccacctgaat acttcaaata gggtattatt    4080
cgaagaggtt gcaaagtctg tcggagtttt tctcggcata ccactgggaa ttggcattat    4140
catacgtttg ggaagtctta ccatagctgg taaaagtaat tatgaaaaat acattttgag    4200
atttatttct ccatgggcaa tgatcggatt tcattacact ttatttgtta ttttattag    4260
tagaggttat caatttatcc acgaaattgg ttctgcaata ttgtgctttg tcccattggt    4320
gctttacttc tttattgcat ggttttgac cttcgcatta atgaggtact tatcaatatc    4380
taggagtgat acacaaagag aatgtagctg tgaccaagaa ctactttaa agagggtctg    4440
gggaagaaag tcttgtgaag ctagcttttc tattacgatg acgcaatgtt tcactatggc    4500
ttcaaataat tttgaactat ccctggcaat tgctatttcc ttatatggta acaatagcaa    4560
```

```
gcaagcaata gctgcaacat ttgggccgtt gctagaagtt ccaatttat tgattttggc      4620 aatagtcgcg agaatcctta aaccatatta tatatggaac aatagaaatt aattaacagg      4680 cccctttcc tttgtcgata tcatgtaatt agttatgtca cgcttacatt cacgccctcc      4740
tcccacatcc gctctaaccg aaaaggaagg agttagacaa cctgaagtct aggtccctat      4800 ttatttttt taatagttat gttagtatta agaacgttat ttatatttca aattttctt       4860 tttttctgt acaaacgcgt gtacgcatgt aacattatac tgaaaaccttt gcttgagaag      4920 gttttgggac gctcgaaggc tttaatttgc aagctgcggc ctaaggcgcg ccaggccata      4980
atggcccaaa tgcaagagga cattagaaat gtgtttggta agaacatgaa gccggaggca      5040
tacaaacgat tcacagattt gaaggaggaa acaaactgc atccaccgga agtgccagca      5100
gccgtgtatg ccaaccttgc tctcaaaggc attcctacgg atctgagtgg gaaatatctg      5160
agattcacag cccactatt ggaacagtac caaacctagt ttggccgatc catgattatg       5220
taatgcatat agttttgtc gatgctcacc cgtttcgagt ctgtctcgta tcgtcttacg       5280
tataagttca agcatgttta ccaggtctgt tagaaactcc tttgtgaggg caggacctat      5340
tcgtctcggt cccgttgttt ctaagagact gtacagccaa gcgcagaatg gtggcattaa      5400
ccataagagg attctgatcg gacttggtct attggctatt ggaaccaccc tttacgggac      5460
aaccaaccct accaagactc ctattgcatt tgtggaacca gccacggaaa gagcgtttaa      5520
ggacggagac gtctctgtga ttttgttct cggaggtcca ggagctggaa aaggtaccca       5580
atgtgccaaa ctagtgagta attacggatt tgttcacctg tcagctggag acttgttacg      5640
tgcagaacag aagagggagg ggtctaagta tggagagatg atttcccagt atatcagaga      5700
tggactgata gtacctcaag aggtcaccat tgcgctcttg gagcaggcca tgaaggaaaa      5760
cttcgagaaa gggaagacac ggttcttgat tgatggattc cctcgtaaga tggaccaggc      5820
caaaactttt gaggaaaaag tcgcaaagtc caaggtgaca cttttcttg attgtcccga       5880 atcagtgctc cttgagagat tacttaaaag aggacagaca agcggaagag aggatgataa      5940
tgcggagagt atcaaaaaaa gattcaaaac attcgtggaa acttcgatgc ctgtggtgga      6000
ctatttcggg aagcaaggac gcgttttgaa ggtatcttgt gaccaccctg tggatcaagt      6060
gtattcacag gttgtgtcgg tgctaaaaga gaagggatc tttgccgata acgacgga        6120 gaataaataa acattgtaat aagatttaga ctgtgaatgt tctatgtaat attttctcgag     6180 atactgtatc tatctggtgt accgtatcac tctggacttg caaactcatt gattacttgt      6240
gcaatgggca agaaggatag ctctagaaag aagaagaaaa aggagccgcc tgaagagctg      6300
gatctttccg aggttgttcc aacttttggt tatgaggaat tcatgttga gcaagaggag       6360 aatccggtcg atcaagacga acttgacggc cataatggcc tagcttggcg taatcatggt      6420
catagctgtt tcctgtgtga aattgttatc cgctcacaat tccacacaac atacgagccg      6480
gaagcataaa gtgtaaagcc tggggtgcct aatgagtgag ctaactcaca ttaattgcgt      6540
tgcgctcact gcccgctttc cagtcgggaa acctgtcgtg ccagctgcat taatgaatcg      6600
gccaacgcgc ggggagaggc ggtttgcgta ttgggcgctc ttccgcttcc tcgctcactg      6660
actcgctgcg ctcggtcgtt cggctgcggc gagcggtatc agctcactca aaggcggtaa      6720
tacggttatc cacagaatca ggggataacg caggaaagaa catgtgagca aaaggccagc      6780
aaaaggccag gaaccgtaaa aaggccgcgt tgctggcgtt ttccatagg ctccgccccc       6840 ctgacgagca tcacaaaaat cgacgctcaa gtcagaggtg cgaaacccg acaggactat       6900
```

| | | | |
|---|---|---|---|
| aaagatacca | ggcgtttccc | cctggaagct | ccctcgtgcg | ctctcctgtt | ccgaccctgc | 6960 |
| cgcttaccgg | atacctgtcc | gcctttctcc | cttcgggaag | cgtggcgctt | tctcatagct | 7020 |
| cacgctgtag | gtatctcagt | tcggtgtagg | tcgttcgctc | caagctgggc | tgtgtgcacg | 7080 |
| aaccccccgt | tcagcccgac | cgctgcgcct | tatccggtaa | ctatcgtctt | gagtccaacc | 7140 |
| cggtaagaca | cgacttatcg | ccactggcag | cagccactgg | taacaggatt | agcagagcga | 7200 |
| ggtatgtagg | cggtgctaca | gagttcttga | agtggtggcc | taactacggc | tacactagaa | 7260 |
| ggacagtatt | tggtatctgc | gctctgctga | agccagttac | cttcggaaaa | agagttggta | 7320 |
| gctcttgatc | cggcaaacaa | accaccgctg | gtagcggtgg | tttttttgtt | tgcaagcagc | 7380 |
| agattacgcg | cagaaaaaaa | ggatctcaag | aagatccttt | gatcttttct | acggggtctg | 7440 |
| acgctcagtg | gaacgaaaac | tcacgttaag | ggattttggt | catgagatta | tcaaaaagga | 7500 |
| tcttcaccta | gatcctttta | aattaaaaat | gaagttttaa | atcaatctaa | agtatatatg | 7560 |
| agtaaacttg | gtctgacagt | taccaatgct | taatcagtga | ggcacctatc | tcagcgatct | 7620 |
| gtctatttcg | ttcatccata | gttgcctgac | tccccgtcgt | gtagataact | acgatacggg | 7680 |
| agggcttacc | atctggcccc | agtgctgcaa | tgataccgcg | agacccacgc | tcaccggctc | 7740 |
| cagatttatc | agcaataaac | cagccagccg | gaagggccga | gcgcagaagt | ggtcctgcaa | 7800 |
| ctttatccgc | ctccatccag | tctattaatt | gttgccggga | agctagagta | agtagttcgc | 7860 |
| cagttaatag | tttgcgcaac | gttgttgcca | ttgctacagg | catcgtggtg | tcacgctcgt | 7920 |
| cgtttggtat | ggcttcattc | agctccggtt | cccaacgatc | aaggcgagtt | acatgatccc | 7980 |
| ccatgttgtg | caaaaaagcg | gttagctcct | tcggtcctcc | gatcgttgtc | agaagtaagt | 8040 |
| tggccgcagt | gttatcactc | atggttatgg | cagcactgca | taattctctt | actgtcatgc | 8100 |
| catccgtaag | atgcttttct | gtgactggtg | agtactcaac | caagtcattc | tgagaatagt | 8160 |
| gtatgcggcg | accgagttgc | tcttgcccgg | cgtcaatacg | ggataatacc | gcgccacata | 8220 |
| gcagaacttt | aaaagtgctc | atcattggaa | aacgttcttc | ggggcgaaaa | ctctcaagga | 8280 |
| tcttaccgct | gttgagatcc | agttcgatgt | aacccactcg | tgcacccaac | tgatcttcag | 8340 |
| catcttttac | tttcaccagc | gtttctgggt | gagcaaaaac | aggaaggcaa | aatgccgcaa | 8400 |
| aaaagggaat | aagggcgaca | cggaaatgtt | gaatactcat | actcttcctt | tttcaatatt | 8460 |
| attgaagcat | ttatcagggt | tattgtctca | tgagcggata | catatttgaa | tgtatttaga | 8520 |
| aaaataaaca | aataggggtt | ccgcgcacat | ttccccgaaa | agtgccacct | gacgtctaag | 8580 |
| aaaccattat | tatcatgaca | ttaacctata | aaaataggcg | tatcacgagg | cccttcgtc | 8640 |

<210> SEQ ID NO 6
<211> LENGTH: 9180
<212> TYPE: PRT
<213> ORGANISM: Artificial Sequence
<220> FEATURE:
<223> OTHER INFORMATION: Plasmid pGLY9008

<400> SEQUENCE: 6

Thr Cys Gly Cys Gly Cys Gly Thr Thr Thr Cys Gly Gly Thr Gly Ala
1               5                   10                  15

Thr Gly Ala Cys Gly Gly Thr Gly Ala Ala Ala Ala Cys Cys Thr Cys
            20                  25                  30

Thr Gly Ala Cys Ala Cys Ala Thr Gly Cys Ala Gly Cys Thr Cys Cys
        35                  40                  45

Cys Gly Gly Ala Gly Ala Cys Gly Gly Thr Cys Ala Cys Ala Gly Cys
    50                  55                  60

-continued

Thr Thr Gly Thr Cys Thr Gly Thr Ala Ala Gly Cys Gly Gly Ala Thr
65 70 75 80

Gly Cys Cys Gly Gly Gly Ala Gly Cys Ala Gly Ala Cys Ala Ala Gly
85 90 95

Cys Cys Cys Gly Thr Cys Ala Gly Gly Gly Cys Gly Cys Gly Thr Cys
100 105 110

Ala Gly Cys Gly Gly Gly Thr Gly Thr Thr Gly Gly Cys Gly Gly Gly
115 120 125

Thr Gly Thr Cys Gly Gly Gly Gly Cys Thr Gly Gly Cys Thr Thr Ala
130 135 140

Ala Cys Thr Ala Thr Gly Cys Gly Gly Cys Ala Thr Cys Ala Gly Ala
145 150 155 160

Gly Cys Ala Gly Ala Thr Thr Gly Thr Ala Cys Thr Gly Ala Gly Ala
165 170 175

Gly Thr Gly Cys Ala Cys Cys Ala Thr Ala Thr Gly Cys Gly Gly Thr
180 185 190

Gly Thr Gly Ala Ala Ala Thr Ala Cys Cys Gly Cys Ala Cys Ala Gly
195 200 205

Ala Thr Gly Cys Gly Thr Ala Ala Gly Gly Ala Gly Ala Ala Ala Ala
210 215 220

Thr Ala Cys Cys Gly Cys Ala Thr Cys Ala Gly Gly Cys Gly Cys Cys
225 230 235 240

Ala Thr Thr Cys Gly Cys Cys Ala Thr Thr Cys Ala Gly Gly Cys Thr
245 250 255

Gly Cys Gly Cys Ala Ala Cys Thr Gly Thr Thr Gly Gly Gly Ala Ala
260 265 270

Gly Gly Gly Cys Gly Ala Thr Cys Gly Gly Thr Gly Cys Gly Gly Gly
275 280 285

Cys Cys Thr Cys Thr Thr Cys Gly Cys Thr Ala Thr Thr Ala Cys Gly
290 295 300

Cys Cys Ala Gly Cys Thr Gly Gly Cys Gly Ala Ala Ala Gly Gly Gly
305 310 315 320

Gly Gly Ala Thr Gly Thr Gly Cys Thr Gly Cys Ala Ala Gly Gly Cys
325 330 335

Gly Ala Thr Thr Ala Ala Gly Thr Thr Gly Gly Gly Thr Ala Ala Cys
340 345 350

Gly Cys Cys Ala Gly Gly Gly Thr Thr Thr Thr Cys Cys Cys Ala Gly
355 360 365

Thr Cys Ala Cys Gly Ala Cys Gly Thr Thr Gly Thr Ala Ala Ala Ala
370 375 380

Cys Gly Ala Cys Gly Gly Cys Cys Ala Gly Thr Gly Ala Ala Thr Thr
385 390 395 400

Gly Ala Gly Ala Thr Cys Thr Ala Ala Cys Ala Thr Cys Cys Ala Ala
405 410 415

Ala Gly Ala Cys Gly Ala Ala Ala Gly Gly Thr Thr Gly Ala Ala Thr
420 425 430

Gly Ala Ala Ala Cys Cys Thr Thr Thr Thr Thr Gly Cys Cys Ala Thr
435 440 445

Cys Cys Gly Ala Cys Ala Thr Cys Cys Ala Cys Ala Gly Gly Thr Cys
450 455 460

Cys Ala Thr Thr Cys Thr Cys Ala Cys Ala Cys Ala Thr Ala Ala Gly
465 470 475 480

-continued

```
Thr Gly Cys Cys Ala Ala Ala Cys Gly Cys Ala Ala Cys Ala Gly Gly
                485                 490                 495

Ala Gly Gly Gly Gly Ala Thr Ala Cys Ala Cys Thr Ala Gly Cys Ala
            500                 505                 510

Gly Cys Ala Gly Ala Cys Cys Gly Thr Thr Gly Cys Ala Ala Ala Cys
        515                 520                 525

Gly Cys Ala Gly Gly Ala Cys Cys Thr Cys Cys Ala Cys Thr Cys Cys
    530                 535                 540

Thr Cys Thr Thr Cys Thr Cys Cys Thr Cys Ala Ala Cys Ala Cys Cys
545                 550                 555                 560

Cys Ala Cys Thr Thr Thr Thr Gly Cys Cys Ala Thr Cys Gly Ala Ala
                565                 570                 575

Ala Ala Ala Cys Cys Ala Gly Cys Cys Cys Ala Gly Thr Thr Ala Thr
            580                 585                 590

Thr Gly Gly Gly Cys Thr Thr Gly Ala Thr Thr Gly Gly Ala Gly Cys
        595                 600                 605

Thr Cys Gly Cys Thr Cys Ala Thr Thr Cys Cys Ala Ala Thr Thr Cys
    610                 615                 620

Cys Thr Thr Cys Thr Ala Thr Thr Ala Gly Gly Cys Thr Ala Cys Thr
625                 630                 635                 640

Ala Ala Cys Ala Cys Cys Ala Thr Gly Ala Cys Thr Thr Thr Ala Thr
                645                 650                 655

Thr Ala Gly Cys Cys Thr Gly Thr Cys Thr Ala Thr Cys Cys Thr Gly
            660                 665                 670

Gly Cys Cys Cys Cys Cys Cys Thr Gly Gly Cys Gly Ala Gly Gly Thr
        675                 680                 685

Thr Cys Ala Thr Gly Thr Thr Thr Gly Thr Thr Thr Ala Thr Thr Thr
    690                 695                 700

Cys Cys Gly Ala Ala Thr Gly Cys Ala Ala Cys Ala Ala Gly Cys Thr
705                 710                 715                 720

Cys Cys Gly Cys Ala Thr Thr Ala Cys Ala Cys Cys Cys Gly Ala Ala
                725                 730                 735

Cys Ala Thr Cys Ala Cys Thr Cys Cys Ala Gly Ala Thr Gly Ala Gly
            740                 745                 750

Gly Gly Cys Thr Thr Thr Cys Thr Gly Ala Gly Thr Gly Thr Gly Gly
        755                 760                 765

Gly Gly Thr Cys Ala Ala Ala Thr Ala Gly Thr Thr Thr Cys Ala Thr
    770                 775                 780

Gly Thr Thr Cys Cys Cys Cys Ala Ala Ala Thr Gly Gly Cys Cys Cys
785                 790                 795                 800

Ala Ala Ala Ala Cys Thr Gly Ala Cys Ala Gly Thr Thr Thr Ala Ala
                805                 810                 815

Ala Cys Gly Cys Thr Gly Thr Cys Thr Thr Gly Gly Ala Ala Cys Cys
            820                 825                 830

Thr Ala Ala Thr Ala Thr Gly Ala Cys Ala Ala Ala Ala Gly Cys Gly
        835                 840                 845

Thr Gly Ala Thr Cys Thr Cys Ala Thr Cys Cys Ala Ala Gly Ala Thr
    850                 855                 860

Gly Ala Ala Cys Thr Ala Ala Gly Thr Thr Thr Gly Gly Thr Thr Cys
865                 870                 875                 880

Gly Thr Thr Gly Ala Ala Ala Thr Gly Cys Thr Ala Ala Cys Gly Gly
                885                 890                 895

Cys Cys Ala Gly Thr Thr Gly Gly Thr Cys Ala Ala Ala Ala Ala Gly
```

-continued

```
            900                 905                 910

Ala Ala Ala Cys Thr Thr Cys Cys Ala Ala Ala Ala Gly Thr Cys Gly
        915                 920                 925

Gly Cys Ala Thr Ala Cys Cys Gly Thr Thr Thr Gly Thr Cys Thr Thr
    930                 935                 940

Gly Thr Thr Thr Gly Gly Thr Ala Thr Thr Gly Ala Thr Thr Gly Ala
945                 950                 955                 960

Cys Gly Ala Ala Thr Gly Cys Thr Cys Ala Ala Ala Ala Ala Thr Ala
                965                 970                 975

Ala Thr Cys Thr Cys Ala Thr Thr Ala Ala Thr Gly Cys Thr Thr Ala
            980                 985                 990

Gly Cys Gly Cys Ala Gly Thr Cys  Thr Cys Thr Cys Thr  Ala Thr Cys
        995                 1000                1005

Gly Cys  Thr Thr Cys Thr Gly  Ala Ala Cys Cys Cys  Cys Gly Gly
    1010                1015                1020

Thr Gly  Cys Ala Cys Cys Thr  Gly Thr Gly Cys Cys  Gly Ala Ala
    1025                1030                1035

Ala Cys  Gly Cys Ala Ala Ala  Thr Gly Gly Gly Gly  Ala Ala Ala
    1040                1045                1050

Cys Ala  Cys Cys Cys Gly Cys  Thr Thr Thr Thr Thr  Gly Gly Ala
    1055                1060                1065

Thr Gly  Ala Thr Thr Ala Thr  Gly Cys Ala Thr Thr  Gly Thr Cys
    1070                1075                1080

Thr Cys  Cys Ala Cys Ala Thr  Thr Gly Thr Ala Thr  Gly Cys Thr
    1085                1090                1095

Thr Cys  Cys Ala Ala Gly Ala  Thr Thr Cys Thr Gly  Gly Thr Gly
    1100                1105                1110

Gly Gly  Ala Ala Thr Ala Cys  Thr Gly Cys Thr Gly  Ala Thr Ala
    1115                1120                1125

Gly Cys  Cys Thr Ala Ala Cys  Gly Thr Thr Cys Ala  Thr Gly Ala
    1130                1135                1140

Thr Cys  Ala Ala Ala Ala Thr  Thr Thr Ala Ala Cys  Thr Gly Thr
    1145                1150                1155

Thr Cys  Thr Ala Ala Cys Cys  Cys Cys Thr Ala Cys  Thr Thr Gly
    1160                1165                1170

Ala Cys  Ala Gly Cys Ala Ala  Thr Ala Thr Ala Thr  Ala Ala Ala
    1175                1180                1185

Cys Ala  Gly Ala Ala Gly Gly  Ala Ala Gly Cys Thr  Gly Cys Cys
    1190                1195                1200

Cys Thr  Gly Thr Cys Thr Thr  Ala Ala Ala Cys Cys  Thr Thr Thr
    1205                1210                1215

Thr Thr  Thr Thr Thr Thr Ala  Thr Cys Ala Thr Cys  Ala Thr Thr
    1220                1225                1230

Ala Thr  Thr Ala Gly Cys Thr  Thr Ala Cys Thr Thr  Thr Cys Ala
    1235                1240                1245

Thr Ala  Ala Thr Thr Gly Cys  Gly Ala Cys Thr Gly  Gly Thr Thr
    1250                1255                1260

Cys Cys  Ala Ala Thr Thr Gly  Ala Cys Ala Ala Gly  Cys Thr Thr
    1265                1270                1275

Thr Thr  Gly Ala Thr Thr Thr  Thr Ala Ala Cys Gly  Ala Cys Thr
    1280                1285                1290

Thr Thr  Thr Ala Ala Cys Gly  Ala Cys Ala Ala Cys  Thr Thr Gly
    1295                1300                1305
```

-continued

```
Ala Gly Ala Ala Gly Ala Thr Cys Ala Ala Ala Ala Ala Ala Cys
    1310                1315                1320

Ala Ala Cys Thr Ala Ala Thr Thr Ala Thr Thr Cys Gly Ala Ala
    1325                1330                1335

Ala Cys Gly Gly Ala Ala Thr Thr Cys Ala Cys Gly Ala Thr Gly
    1340                1345                1350

Ala Gly Ala Thr Thr Thr Cys Cys Thr Thr Cys Ala Ala Thr Thr
    1355                1360                1365

Thr Thr Thr Ala Cys Thr Gly Cys Thr Gly Thr Thr Thr Thr Ala
    1370                1375                1380

Thr Thr Cys Gly Cys Ala Gly Cys Ala Thr Cys Cys Thr Cys Cys
    1385                1390                1395

Gly Cys Ala Thr Thr Ala Gly Cys Thr Gly Ala Cys Ala Ala Gly
    1400                1405                1410

Ala Cys Ala Cys Ala Thr Ala Cys Thr Thr Gly Thr Cys Cys Ala
    1415                1420                1425

Cys Cys Ala Thr Gly Thr Cys Cys Ala Gly Cys Thr Cys Cys Ala
    1430                1435                1440

Gly Ala Ala Thr Thr Gly Thr Thr Gly Gly Gly Thr Gly Gly Thr
    1445                1450                1455

Cys Cys Ala Thr Cys Cys Gly Thr Thr Thr Thr Cys Thr Thr Gly
    1460                1465                1470

Thr Thr Cys Cys Cys Ala Cys Cys Ala Ala Ala Gly Cys Cys Ala
    1475                1480                1485

Ala Ala Gly Gly Ala Cys Ala Cys Thr Thr Thr Gly Ala Thr Gly
    1490                1495                1500

Ala Thr Cys Thr Cys Cys Ala Gly Ala Ala Cys Thr Cys Cys Ala
    1505                1510                1515

Gly Ala Gly Gly Thr Thr Ala Cys Ala Thr Gly Thr Gly Thr Thr
    1520                1525                1530

Gly Thr Thr Gly Thr Thr Gly Ala Cys Gly Thr Thr Thr Cys Thr
    1535                1540                1545

Cys Ala Cys Gly Ala Gly Gly Ala Cys Cys Cys Ala Gly Ala Gly
    1550                1555                1560

Gly Thr Thr Ala Ala Gly Thr Thr Cys Ala Ala Cys Thr Gly Gly
    1565                1570                1575

Thr Ala Cys Gly Thr Thr Gly Ala Cys Gly Gly Thr Gly Thr Thr
    1580                1585                1590

Gly Ala Ala Gly Thr Thr Cys Ala Cys Ala Ala Cys Gly Cys Thr
    1595                1600                1605

Ala Ala Gly Ala Cys Thr Ala Ala Gly Cys Cys Ala Ala Gly Ala
    1610                1615                1620

Gly Ala Ala Gly Ala Gly Cys Ala Gly Thr Ala Cys Ala Ala Cys
    1625                1630                1635

Thr Cys Cys Ala Cys Thr Thr Ala Cys Ala Gly Ala Gly Thr Thr
    1640                1645                1650

Gly Thr Thr Thr Cys Cys Gly Thr Thr Thr Thr Gly Ala Cys Thr
    1655                1660                1665

Gly Thr Thr Thr Thr Gly Cys Ala Cys Cys Ala Gly Gly Ala Cys
    1670                1675                1680

Thr Gly Gly Thr Thr Gly Ala Ala Cys Gly Gly Thr Ala Ala Ala
    1685                1690                1695
```

-continued

Gly Ala Ala Thr Ala Cys Ala Ala Gly Thr Gly Thr Ala Ala Gly
    1700                1705                1710

Gly Thr Thr Thr Cys Cys Ala Ala Cys Ala Ala Gly Gly Cys Thr
    1715                1720                1725

Thr Thr Gly Cys Cys Ala Gly Cys Thr Cys Cys Ala Ala Thr Cys
    1730                1735                1740

Gly Ala Ala Ala Ala Gly Ala Cys Thr Ala Thr Cys Thr Cys Cys
    1745                1750                1755

Ala Ala Gly Gly Cys Thr Ala Ala Gly Gly Thr Cys Ala Ala
    1760                1765                1770

Cys Cys Ala Ala Gly Ala Gly Ala Gly Cys Cys Ala Cys Ala Gly
    1775                1780                1785

Gly Thr Thr Thr Ala Cys Ala Cys Thr Thr Gly Cys Cys Ala
    1790                1795                1800

Cys Cys Ala Thr Cys Ala Gly Ala Gly Ala Ala Gly Ala Gly
    1805                1810                1815

Ala Thr Gly Ala Cys Thr Ala Ala Gly Ala Ala Cys Cys Ala Gly
    1820                1825                1830

Gly Thr Thr Thr Cys Cys Thr Thr Gly Ala Cys Thr Thr Gly Thr
    1835                1840                1845

Thr Thr Gly Gly Thr Thr Ala Ala Ala Gly Gly Ala Thr Thr Cys
    1850                1855                1860

Thr Ala Cys Cys Cys Ala Thr Cys Cys Gly Ala Cys Ala Thr Thr
    1865                1870                1875

Gly Cys Thr Gly Thr Thr Gly Ala Gly Thr Gly Gly Gly Ala Ala
    1880                1885                1890

Thr Cys Thr Ala Ala Cys Gly Gly Thr Cys Ala Ala Cys Cys Ala
    1895                1900                1905

Gly Ala Gly Ala Ala Cys Ala Cys Thr Ala Cys Ala Ala Gly
    1910                1915                1920

Ala Cys Thr Ala Cys Thr Cys Cys Ala Cys Cys Ala Gly Thr Thr
    1925                1930                1935

Thr Thr Gly Gly Ala Thr Thr Cys Thr Gly Ala Thr Gly Gly Thr
    1940                1945                1950

Thr Cys Cys Thr Thr Cys Thr Thr Cys Thr Thr Gly Thr Ala Cys
    1955                1960                1965

Thr Cys Cys Ala Ala Gly Thr Thr Gly Ala Cys Thr Gly Thr Thr
    1970                1975                1980

Gly Ala Cys Ala Ala Gly Thr Cys Cys Ala Gly Ala Thr Gly Gly
    1985                1990                1995

Cys Ala Ala Cys Ala Gly Gly Gly Thr Ala Ala Cys Gly Thr Thr
    2000                2005                2010

Thr Thr Cys Thr Cys Cys Thr Gly Thr Thr Cys Cys Gly Thr Thr
    2015                2020                2025

Ala Thr Gly Cys Ala Thr Gly Ala Gly Gly Cys Thr Thr Thr Gly
    2030                2035                2040

Cys Ala Cys Ala Ala Cys Cys Ala Cys Thr Ala Cys Ala Cys Thr
    2045                2050                2055

Cys Ala Ala Ala Ala Gly Thr Cys Cys Thr Thr Gly Thr Cys Thr
    2060                2065                2070

Thr Thr Gly Thr Cys Cys Cys Thr Gly Gly Thr Gly Gly Thr
    2075                2080                2085

Gly Gly Thr Gly Gly Thr Gly Thr Cys Gly Ala Cys Cys Ala Ala

-continued 2090 2095 2100

Thr Thr Cys Thr Cys Thr Ala Ala Cys Thr Cys Thr Ala Cys Thr
2105 2110 2115

Thr Cys Cys Gly Cys Thr Thr Cys Cys Thr Cys Thr Ala Cys Thr
2120 2125 2130

Gly Ala Cys Gly Thr Thr Ala Cys Thr Thr Cys Cys Thr Cys Cys
2135 2140 2145

Thr Cys Cys Thr Cys Thr Ala Thr Thr Thr Cys Thr Ala Cys Thr
2150 2155 2160

Thr Cys Cys Thr Cys Cys Gly Gly Thr Thr Cys Cys Gly Thr Thr
2165 2170 2175

Ala Cys Thr Ala Thr Thr Ala Cys Thr Thr Cys Cys Thr Cys Thr
2180 2185 2190

Gly Ala Gly Gly Cys Thr Cys Cys Ala Gly Ala Ala Thr Cys Thr
2195 2200 2205

Gly Ala Cys Ala Ala Cys Gly Gly Thr Ala Cys Thr Thr Cys Thr
2210 2215 2220

Ala Cys Thr Gly Cys Thr Gly Cys Thr Cys Cys Ala Ala Cys Thr
2225 2230 2235

Gly Ala Ala Ala Cys Thr Thr Cys Thr Ala Cys Thr Gly Ala Gly
2240 2245 2250

Gly Cys Thr Cys Cys Thr Ala Cys Thr Ala Cys Thr Gly Cys Thr
2255 2260 2265

Ala Thr Thr Cys Cys Ala Ala Cys Thr Ala Ala Cys Gly Gly Ala
2270 2275 2280

Ala Cys Thr Thr Cys Cys Ala Cys Ala Gly Ala Gly Gly Cys Thr
2285 2290 2295

Cys Cys Ala Ala Cys Ala Ala Cys Ala Gly Cys Thr Ala Thr Cys
2300 2305 2310

Cys Cys Thr Ala Cys Ala Ala Ala Cys Gly Gly Thr Ala Cys Ala
2315 2320 2325

Thr Cys Cys Ala Cys Thr Gly Ala Ala Gly Cys Thr Cys Cys Thr
2330 2335 2340

Ala Cys Thr Gly Ala Cys Ala Cys Thr Ala Cys Thr Ala Cys Ala
2345 2350 2355

Gly Ala Ala Gly Cys Thr Cys Cys Ala Ala Cys Thr Ala Cys Thr
2360 2365 2370

Gly Cys Thr Thr Thr Gly Cys Cys Thr Ala Cys Thr Ala Ala Thr
2375 2380 2385

Gly Gly Thr Ala Cys Ala Thr Cys Ala Ala Cys Ala Gly Ala Gly
2390 2395 2400

Gly Cys Thr Cys Cys Thr Ala Cys Ala Gly Ala Thr Ala Cys Ala
2405 2410 2415

Ala Cys Ala Ala Cys Thr Gly Ala Ala Gly Cys Thr Cys Cys Ala
2420 2425 2430

Ala Cys Ala Ala Cys Thr Gly Gly Ala Thr Thr Gly Cys Cys Ala
2435 2440 2445

Ala Cys Ala Ala Ala Cys Gly Gly Thr Ala Cys Thr Ala Cys Thr
2450 2455 2460

Thr Cys Thr Gly Cys Thr Thr Thr Cys Cys Cys Ala Cys Cys Ala
2465 2470 2475

Ala Cys Thr Ala Cys Thr Thr Cys Cys Thr Thr Gly Cys Cys Ala
2480 2485 2490

```
Cys Cys Ala Thr Cys Cys Ala Ala Cys Ala Cys Thr Ala Cys Thr
    2495                2500                2505

Ala Cys Thr Ala Cys Thr Cys Cys Ala Cys Cys Ala Thr Ala Cys
    2510                2515                2520

Ala Ala Cys Cys Cys Ala Thr Cys Cys Ala Cys Thr Gly Ala Cys
    2525                2530                2535

Thr Ala Cys Ala Cys Thr Ala Cys Thr Gly Ala Cys Thr Ala Cys
    2540                2545                2550

Ala Cys Ala Gly Thr Thr Gly Thr Thr Ala Cys Thr Gly Ala Gly
    2555                2560                2565

Thr Ala Cys Ala Cys Thr Ala Cys Thr Thr Ala Cys Thr Gly Thr
    2570                2575                2580

Cys Cys Ala Gly Ala Gly Cys Cys Ala Ala Cys Thr Ala Cys Thr
    2585                2590                2595

Thr Thr Cys Ala Cys Ala Ala Cys Ala Ala Ala Cys Gly Gly Ala
    2600                2605                2610

Ala Ala Gly Ala Cys Thr Thr Ala Cys Ala Cys Thr Gly Thr Thr
    2615                2620                2625

Ala Cys Thr Gly Ala Gly Cys Cys Thr Ala Cys Thr Ala Cys Thr
    2630                2635                2640

Thr Thr Gly Ala Cys Thr Ala Thr Cys Ala Cys Thr Gly Ala Cys
    2645                2650                2655

Thr Gly Thr Cys Cys Ala Thr Gly Thr Ala Cys Thr Ala Thr Cys
    2660                2665                2670

Gly Ala Gly Ala Ala Gly Cys Cys Ala Ala Cys Thr Ala Cys Thr
    2675                2680                2685

Ala Cys Thr Thr Cys Cys Ala Cys Thr Ala Cys Ala Gly Ala Gly
    2690                2695                2700

Thr Ala Thr Ala Cys Thr Gly Thr Thr Gly Thr Thr Ala Cys Ala
    2705                2710                2715

Gly Ala Ala Thr Ala Cys Ala Cys Ala Ala Cys Ala Thr Ala Thr
    2720                2725                2730

Thr Gly Thr Cys Cys Thr Gly Ala Gly Cys Cys Ala Ala Cys Ala
    2735                2740                2745

Ala Cys Ala Thr Thr Cys Ala Cys Thr Ala Cys Thr Ala Ala Thr
    2750                2755                2760

Gly Gly Ala Ala Ala Ala Ala Cys Ala Thr Ala Cys Ala Cys Ala
    2765                2770                2775

Gly Thr Thr Ala Cys Ala Gly Ala Ala Cys Cys Ala Ala Cys Thr
    2780                2785                2790

Ala Cys Ala Thr Thr Gly Ala Cys Ala Ala Thr Thr Ala Cys Ala
    2795                2800                2805

Gly Ala Thr Thr Gly Thr Cys Cys Thr Thr Gly Thr Ala Cys Ala
    2810                2815                2820

Ala Thr Thr Gly Ala Gly Ala Ala Gly Thr Cys Cys Gly Ala Gly
    2825                2830                2835

Gly Cys Thr Cys Cys Thr Gly Ala Ala Thr Cys Thr Thr Cys Thr
    2840                2845                2850

Gly Thr Thr Cys Cys Ala Gly Thr Thr Ala Cys Thr Gly Ala Ala
    2855                2860                2865

Thr Cys Cys Ala Ala Gly Gly Gly Thr Ala Cys Thr Ala Cys Thr
    2870                2875                2880
```

-continued

| | | | | | | | | | |
|---|---|---|---|---|---|---|---|---|---|
| Ala | Cys<br>2885 | Thr | Ala | Ala<br>2890 | Gly | Ala | Ala<br>2895 | Cys Thr | Gly Gly |
| Gly | Thr<br>2900 | Thr | Ala | Cys<br>2905 | Thr | Ala | Cys<br>2910 | Thr Ala | Ala Gly | Cys Ala | Gly |

```
Ala Cys  Thr  Ala  Ala  Gly  Ala  Ala  Cys  Thr  Gly  Gly  Thr
    2885           2890           2895

Gly Thr  Thr  Ala  Cys  Thr  Ala  Cys  Thr  Ala  Ala  Gly  Cys  Ala  Gly
    2900           2905           2910

Ala Cys  Thr  Ala  Cys  Thr  Gly  Cys  Thr  Ala  Ala  Cys  Cys  Cys  Ala
    2915           2920           2925

Thr Cys  Cys  Thr  Thr  Gly  Ala  Cys  Thr  Gly  Thr  Thr  Cys  Cys
    2930           2935           2940

Ala Cys  Thr  Gly  Thr  Thr  Gly  Thr  Thr  Cys  Cys  Ala  Gly  Thr  Thr
    2945           2950           2955

Thr Cys  Thr  Thr  Cys  Cys  Thr  Cys  Thr  Gly  Cys  Thr  Thr  Cys  Thr
    2960           2965           2970

Thr Cys  Cys  Cys  Ala  Cys  Thr  Cys  Cys  Gly  Thr  Thr  Gly  Thr  Thr
    2975           2980           2985

Ala Thr  Cys  Ala  Ala  Cys  Thr  Cys  Cys  Ala  Ala  Cys  Gly  Gly  Thr
    2990           2995           3000

Gly Cys  Thr  Ala  Ala  Cys  Gly  Thr  Thr  Gly  Thr  Thr  Gly  Thr  Thr
    3005           3010           3015

Cys Cys  Thr  Gly  Gly  Thr  Gly  Cys  Thr  Thr  Thr  Gly  Gly  Gly  Ala
    3020           3025           3030

Thr Thr  Gly  Gly  Cys  Thr  Gly  Gly  Thr  Gly  Thr  Thr  Gly  Cys  Thr
    3035           3040           3045

Ala Thr  Gly  Thr  Thr  Gly  Thr  Thr  Cys  Thr  Thr  Gly  Thr  Ala  Ala
    3050           3055           3060

Thr Ala  Gly  Gly  Gly  Cys  Cys  Gly  Gly  Cys  Cys  Ala  Thr  Thr  Thr
    3065           3070           3075

Ala Ala  Ala  Thr  Ala  Cys  Ala  Gly  Gly  Cys  Cys  Cys  Cys  Thr  Thr
    3080           3085           3090

Thr Thr  Cys  Cys  Thr  Thr  Thr  Gly  Thr  Cys  Gly  Ala  Thr  Ala  Thr
    3095           3100           3105

Cys Ala  Thr  Gly  Thr  Ala  Ala  Thr  Thr  Ala  Gly  Thr  Thr  Ala  Thr
    3110           3115           3120

Gly Thr  Cys  Ala  Cys  Gly  Cys  Thr  Thr  Ala  Cys  Ala  Thr  Thr  Cys
    3125           3130           3135

Ala Cys  Gly  Cys  Cys  Cys  Thr  Cys  Cys  Thr  Cys  Cys  Cys  Ala  Cys
    3140           3145           3150

Ala Thr  Cys  Cys  Gly  Cys  Thr  Cys  Thr  Ala  Ala  Cys  Cys  Gly  Ala
    3155           3160           3165

Ala Ala  Ala  Gly  Gly  Ala  Ala  Gly  Gly  Ala  Gly  Thr  Thr  Ala  Gly
    3170           3175           3180

Ala Cys  Ala  Ala  Cys  Cys  Thr  Gly  Ala  Ala  Gly  Thr  Cys  Thr  Ala
    3185           3190           3195

Gly Gly  Thr  Cys  Cys  Cys  Thr  Ala  Thr  Thr  Thr  Ala  Thr  Thr  Thr
    3200           3205           3210

Thr Thr  Thr  Thr  Thr  Ala  Ala  Thr  Ala  Gly  Thr  Thr  Ala  Thr  Gly
    3215           3220           3225

Thr Thr  Ala  Gly  Thr  Ala  Thr  Thr  Ala  Ala  Gly  Ala  Ala  Cys  Gly
    3230           3235           3240

Thr Thr  Ala  Thr  Thr  Thr  Ala  Thr  Ala  Thr  Thr  Thr  Cys  Ala  Ala
    3245           3250           3255

Ala Thr  Thr  Thr  Thr  Thr  Cys  Thr  Thr  Thr  Thr  Thr  Thr  Thr  Thr
    3260           3265           3270

Cys Thr  Gly  Thr  Ala  Cys  Ala  Ala  Ala  Cys  Gly  Cys  Gly  Thr  Gly
```

```
              3275                3280                3285

Thr Ala Cys Gly Cys Ala Thr Gly Thr Ala Ala Cys Ala Thr Thr
        3290                3295                3300

Ala Thr Ala Cys Thr Gly Ala Ala Ala Cys Cys Thr Thr Gly
        3305                3310                3315

Cys Thr Thr Gly Ala Gly Ala Ala Gly Thr Thr Thr Thr Gly
        3320                3325                3330

Gly Gly Ala Cys Gly Cys Thr Cys Gly Ala Ala Gly Gly Cys Thr
        3335                3340                3345

Thr Thr Ala Ala Thr Thr Thr Gly Cys Ala Ala Gly Cys Thr Gly
        3350                3355                3360

Gly Ala Thr Cys Cys Gly Cys Gly Gly Cys Cys Gly Cys Thr Thr
        3365                3370                3375

Ala Cys Gly Cys Gly Cys Cys Gly Thr Thr Cys Thr Thr Cys Gly
        3380                3385                3390

Cys Thr Thr Gly Gly Thr Cys Thr Thr Gly Thr Ala Thr Cys Thr
        3395                3400                3405

Cys Cys Thr Thr Ala Cys Ala Cys Thr Gly Thr Ala Thr Cys Thr
        3410                3415                3420

Thr Cys Cys Cys Ala Thr Thr Thr Gly Cys Gly Thr Thr Thr Ala
        3425                3430                3435

Gly Gly Thr Gly Gly Thr Thr Ala Thr Cys Ala Ala Ala Ala Ala
        3440                3445                3450

Cys Thr Ala Ala Ala Ala Gly Gly Ala Ala Ala Ala Thr Thr
        3455                3460                3465

Thr Cys Ala Gly Ala Thr Gly Thr Thr Thr Ala Thr Cys Thr Cys
        3470                3475                3480

Thr Ala Ala Gly Gly Thr Thr Thr Thr Thr Thr Cys Thr Thr Thr
        3485                3490                3495

Thr Thr Ala Cys Ala Gly Thr Ala Thr Ala Ala Cys Ala Cys Gly
        3500                3505                3510

Thr Gly Ala Thr Gly Cys Gly Thr Cys Ala Cys Gly Thr Gly Gly
        3515                3520                3525

Thr Ala Cys Thr Ala Gly Ala Thr Thr Ala Cys Gly Thr Ala Ala
        3530                3535                3540

Gly Thr Thr Ala Thr Thr Thr Thr Gly Gly Thr Cys Cys Gly Gly
        3545                3550                3555

Thr Gly Gly Gly Thr Ala Ala Gly Thr Gly Gly Gly Thr Ala Ala
        3560                3565                3570

Gly Ala Ala Thr Ala Gly Ala Ala Ala Gly Cys Ala Thr Gly Ala
        3575                3580                3585

Ala Gly Gly Thr Thr Thr Ala Cys Ala Ala Ala Ala Cys Gly
        3590                3595                3600

Cys Ala Gly Thr Cys Ala Cys Gly Ala Ala Thr Thr Ala Thr Thr
        3605                3610                3615

Gly Cys Thr Ala Cys Thr Thr Cys Gly Ala Gly Cys Thr Thr Gly
        3620                3625                3630

Gly Ala Ala Cys Cys Ala Cys Cys Cys Ala Ala Ala Gly Ala
        3635                3640                3645

Thr Thr Ala Thr Ala Thr Thr Gly Thr Ala Cys Thr Gly Ala Thr
        3650                3655                3660

Gly Cys Ala Cys Thr Ala Cys Cys Thr Thr Cys Thr Cys Gly Ala
        3665                3670                3675
```

```
Thr Thr Thr Thr Gly Cys Thr Cys Cys Thr Cys Cys Ala Ala Gly
3680            3685            3690

Ala Ala Cys Cys Thr Ala Cys Gly Ala Ala Ala Ala Cys Ala
3695            3700            3705

Thr Thr Thr Cys Thr Thr Gly Ala Gly Cys Cys Thr Thr Thr
3710            3715            3720

Cys Ala Ala Cys Cys Thr Ala Gly Ala Cys Thr Ala Cys Ala Cys
3725            3730            3735

Ala Thr Cys Ala Ala Gly Thr Thr Ala Thr Thr Ala Ala Gly
3740            3745            3750

Gly Thr Ala Thr Gly Thr Thr Cys Cys Gly Thr Thr Ala Ala Cys
3755            3760            3765

Ala Thr Gly Thr Ala Ala Gly Ala Ala Ala Gly Gly Ala Gly
3770            3775            3780

Ala Gly Gly Ala Thr Ala Gly Ala Thr Cys Gly Thr Thr Ala
3785            3790            3795

Thr Gly Gly Gly Gly Thr Ala Cys Gly Thr Cys Gly Cys Cys Thr
3800            3805            3810

Gly Ala Thr Thr Cys Ala Ala Gly Cys Gly Thr Gly Ala Cys Cys
3815            3820            3825

Ala Thr Thr Cys Gly Ala Ala Gly Ala Ala Thr Ala Gly Gly Cys
3830            3835            3840

Cys Thr Thr Cys Gly Ala Ala Ala Gly Cys Thr Gly Ala Ala Thr
3845            3850            3855

Ala Ala Ala Gly Cys Ala Ala Ala Thr Gly Thr Cys Ala Gly Thr
3860            3865            3870

Thr Gly Cys Gly Ala Thr Thr Gly Gly Thr Ala Thr Gly Cys Thr
3875            3880            3885

Gly Ala Cys Ala Ala Ala Thr Ala Gly Cys Ala Thr Ala Ala
3890            3895            3900

Ala Ala Ala Gly Cys Ala Ala Thr Ala Gly Ala Cys Thr Thr Thr
3905            3910            3915

Cys Thr Ala Ala Cys Cys Ala Cys Cys Thr Gly Thr Thr Thr Thr
3920            3925            3930

Thr Thr Thr Cys Cys Thr Thr Thr Thr Ala Cys Thr Thr Thr Ala
3935            3940            3945

Thr Thr Thr Ala Thr Ala Thr Thr Thr Thr Gly Cys Cys Ala Cys
3950            3955            3960

Cys Gly Thr Ala Cys Thr Ala Ala Cys Ala Ala Gly Thr Thr Cys
3965            3970            3975

Ala Gly Ala Cys Ala Ala Ala Thr Thr Ala Ala Thr Thr Ala Ala
3980            3985            3990

Cys Ala Cys Cys Ala Thr Gly Thr Cys Ala Gly Ala Ala Gly Ala
3995            4000            4005

Thr Cys Ala Ala Ala Ala Ala Ala Gly Thr Gly Ala Ala Ala Ala
4010            4015            4020

Thr Thr Cys Cys Gly Thr Ala Cys Cys Thr Thr Cys Thr Ala Ala
4025            4030            4035

Gly Gly Thr Thr Ala Ala Thr Ala Thr Gly Gly Thr Gly Ala Ala
4040            4045            4050

Thr Cys Gly Cys Ala Cys Cys Gly Ala Thr Ala Thr Ala Cys Thr
4055            4060            4065
```

-continued

```
Gly Ala  Cys Thr Ala Cys Gly  Ala Thr Cys Ala Ala  Gly Thr Cys
    4070                 4075                 4080

Ala Thr  Thr Gly Thr Cys Ala  Thr Gly Gly Cys Thr  Thr Gly Ala
    4085                 4090                 4095

Cys Thr  Thr Gly Ala Thr Gly  Thr Thr Gly Cys Cys  Ala Thr Thr
    4100                 4105                 4110

Thr Ala  Cys Thr Ala Thr Ala  Ala Thr Thr Cys Thr  Cys Thr Cys
    4115                 4120                 4125

Cys Ala  Thr Ala Ala Thr Cys  Ala Thr Thr Gly Cys  Ala Gly Thr
    4130                 4135                 4140

Ala Ala  Thr Ala Ala Thr Thr  Thr Cys Thr Gly Thr  Cys Thr Ala
    4145                 4150                 4155

Thr Gly  Thr Gly Cys Cys Thr  Thr Cys Thr Thr Cys  Cys Cys Gly
    4160                 4165                 4170

Thr Cys  Ala Cys Ala Cys Thr  Thr Thr Thr Gly Ala  Cys Gly Cys
    4175                 4180                 4185

Thr Gly  Ala Ala Gly Gly Thr  Cys Ala Thr Cys Cys  Cys Ala Ala
    4190                 4195                 4200

Thr Cys  Thr Ala Ala Thr Gly  Gly Gly Ala Gly Thr  Gly Thr Cys
    4205                 4210                 4215

Cys Ala  Thr Thr Cys Cys Thr  Thr Thr Gly Ala Cys  Thr Gly Thr
    4220                 4225                 4230

Thr Gly  Gly Thr Ala Thr Gly  Ala Thr Thr Gly Thr  Ala Ala Thr
    4235                 4240                 4245

Gly Ala  Thr Gly Ala Thr Thr  Cys Cys Cys Cys Cys  Gly Ala Thr
    4250                 4255                 4260

Cys Thr  Gly Cys Ala Ala Ala  Gly Thr Thr Thr Cys  Cys Thr Gly
    4265                 4270                 4275

Gly Gly  Ala Gly Thr Cys Thr  Ala Thr Thr Cys Ala  Cys Ala Ala
    4280                 4285                 4290

Gly Thr  Ala Cys Thr Thr Cys  Thr Ala Cys Ala Gly  Gly Ala Gly
    4295                 4300                 4305

Cys Thr  Ala Thr Ala Thr Ala  Ala Gly Gly Ala Ala  Gly Cys Ala
    4310                 4315                 4320

Ala Cys  Thr Ala Gly Cys Cys  Cys Thr Cys Thr Cys  Gly Thr Thr
    4325                 4330                 4335

Ala Thr  Thr Thr Thr Thr Gly  Ala Ala Thr Thr Gly  Gly Gly Thr
    4340                 4345                 4350

Cys Ala  Thr Cys Gly Gly Thr  Cys Cys Thr Thr Thr  Gly Thr Thr
    4355                 4360                 4365

Gly Ala  Thr Gly Ala Cys Ala  Gly Cys Ala Thr Thr  Gly Gly Cys
    4370                 4375                 4380

Gly Thr  Gly Gly Ala Thr Gly  Gly Cys Gly Cys Thr  Ala Thr Thr
    4385                 4390                 4395

Cys Gly  Ala Thr Thr Ala Thr  Ala Ala Gly Gly Ala  Ala Thr Ala
    4400                 4405                 4410

Cys Cys  Gly Thr Cys Ala Ala  Gly Gly Cys Ala Thr  Thr Ala Thr
    4415                 4420                 4425

Thr Ala  Thr Gly Ala Thr Cys  Gly Gly Ala Gly Thr  Ala Gly Cys
    4430                 4435                 4440

Thr Ala  Gly Ala Thr Gly Cys  Ala Thr Thr Gly Cys  Cys Ala Thr
    4445                 4450                 4455

Gly Gly  Thr Gly Cys Thr Ala  Ala Thr Thr Thr Gly  Gly Ala Ala
```

-continued

```
    4460                4465                4470

Thr Cys  Ala Gly Ala Thr Thr  Gly Cys Thr Gly Gly  Ala Gly Gly
    4475                4480                4485

Ala Gly  Ala Cys Ala Ala Thr  Gly Ala Thr Cys Thr  Cys Thr Gly
    4490                4495                4500

Cys Gly  Thr Cys Gly Thr Gly  Cys Thr Thr Gly Thr  Thr Ala Thr
    4505                4510                4515

Thr Ala  Cys Ala Ala Ala Cys  Thr Cys Gly Cys Thr  Thr Thr Thr
    4520                4525                4530

Ala Cys  Ala Gly Ala Thr Gly  Gly Thr Ala Thr Thr  Ala Thr Ala
    4535                4540                4545

Thr Gly  Cys Ala Cys Cys Ala  Thr Thr Gly Cys Ala  Gly Ala Thr
    4550                4555                4560

Ala Thr  Thr Thr Thr Ala Cys  Thr Gly Thr Thr Ala  Thr Gly Thr
    4565                4570                4575

Thr Ala  Thr Thr Thr Cys Thr  Cys Ala Thr Gly Ala  Cys Cys Ala
    4580                4585                4590

Cys Cys  Thr Gly Ala Ala Thr  Ala Cys Thr Thr Cys  Ala Ala Ala
    4595                4600                4605

Thr Ala  Gly Gly Gly Thr Ala  Thr Thr Ala Thr Thr  Cys Gly Ala
    4610                4615                4620

Ala Gly  Ala Gly Gly Thr Thr  Gly Cys Ala Ala Ala  Gly Thr Cys
    4625                4630                4635

Thr Gly  Thr Cys Gly Gly Ala  Gly Thr Thr Thr Thr  Thr Cys Thr
    4640                4645                4650

Cys Gly  Gly Cys Ala Thr Ala  Cys Cys Ala Cys Thr  Gly Gly Gly
    4655                4660                4665

Ala Ala  Thr Thr Gly Gly Cys  Ala Thr Thr Ala Thr  Cys Ala Thr
    4670                4675                4680

Ala Cys  Gly Thr Thr Thr Gly  Gly Gly Ala Ala Gly  Thr Cys Thr
    4685                4690                4695

Thr Ala  Cys Cys Ala Thr Ala  Gly Cys Thr Gly Gly  Thr Ala Ala
    4700                4705                4710

Ala Ala  Gly Thr Ala Ala Thr  Thr Ala Thr Gly Ala  Ala Ala Ala
    4715                4720                4725

Ala Thr  Ala Cys Ala Thr Thr  Thr Thr Gly Ala Gly  Ala Thr Thr
    4730                4735                4740

Thr Ala  Thr Thr Thr Cys Thr  Cys Cys Ala Thr Gly  Gly Gly Cys
    4745                4750                4755

Ala Ala  Thr Gly Ala Thr Cys  Gly Gly Ala Thr Thr  Thr Cys Ala
    4760                4765                4770

Thr Thr  Ala Cys Ala Cys Thr  Thr Thr Ala Thr Thr  Thr Gly Thr
    4775                4780                4785

Thr Ala  Thr Thr Thr Thr Thr  Ala Thr Thr Ala Gly  Thr Ala Gly
    4790                4795                4800

Ala Gly  Gly Thr Thr Ala Thr  Cys Ala Ala Thr Thr  Thr Ala Thr
    4805                4810                4815

Cys Cys  Ala Cys Gly Ala Ala  Ala Thr Thr Gly Gly  Thr Thr Cys
    4820                4825                4830

Thr Gly  Cys Ala Ala Thr Ala  Thr Thr Gly Thr Gly  Cys Thr Thr
    4835                4840                4845

Thr Gly  Thr Cys Cys Cys Ala  Thr Thr Gly Gly Thr  Gly Cys Thr
    4850                4855                4860
```

```
Thr Thr Ala Cys Thr Thr Cys Thr Thr Thr Ala Thr  Thr Gly Cys
    4865                4870                4875

Ala Thr Gly Gly Thr Thr Thr Thr Thr Gly Ala Cys  Cys Thr Thr
    4880                4885                4890

Cys Gly Cys Ala Thr Thr Ala Ala Thr Gly Ala Gly  Gly Thr Ala
    4895                4900                4905

Cys Thr Thr Ala Thr Cys Ala Ala Thr Ala Thr Cys  Thr Ala Gly
    4910                4915                4920

Gly Ala Gly Thr Gly Ala Thr Ala Cys Ala Cys Ala  Ala Ala Gly
    4925                4930                4935

Ala Gly Ala Ala Thr Gly Thr Ala Gly Cys Thr Gly  Thr Gly Ala
    4940                4945                4950

Cys Cys Ala Ala Gly Ala Ala Cys Thr Ala Cys Thr  Thr Thr Thr
    4955                4960                4965

Ala Ala Ala Gly Ala Gly Gly Gly Thr Cys Thr Gly  Gly Gly Gly
    4970                4975                4980

Ala Ala Gly Ala Ala Ala Gly Thr Cys Thr Thr Gly  Thr Gly Ala
    4985                4990                4995

Ala Gly Cys Thr Ala Gly Cys Thr Thr Thr Thr Cys  Thr Ala Thr
    5000                5005                5010

Thr Ala Cys Gly Ala Thr Gly Ala Cys Gly Cys Ala  Ala Thr Gly
    5015                5020                5025

Thr Thr Thr Cys Ala Cys Thr Ala Thr Gly Gly Cys  Thr Thr Cys
    5030                5035                5040

Ala Ala Ala Thr Ala Ala Thr Thr Thr Gly Ala Ala  Ala Cys Thr
    5045                5050                5055

Ala Thr Cys Cys Cys Thr Gly Gly Cys Ala Ala Thr  Thr Gly Cys
    5060                5065                5070

Thr Ala Thr Thr Thr Cys Cys Thr Thr Ala Thr Ala  Thr Gly Gly
    5075                5080                5085

Thr Ala Ala Cys Ala Ala Thr Ala Gly Cys Ala Ala  Gly Cys Ala
    5090                5095                5100

Ala Gly Cys Ala Ala Thr Ala Gly Cys Thr Gly Cys  Ala Ala Cys
    5105                5110                5115

Ala Thr Thr Thr Gly Gly Gly Cys Cys Gly Thr Thr  Gly Cys Thr
    5120                5125                5130

Ala Gly Ala Ala Gly Thr Thr Cys Cys Ala Ala Thr  Thr Thr Thr
    5135                5140                5145

Ala Thr Thr Gly Ala Thr Thr Thr Thr Gly Gly Cys  Ala Ala Thr
    5150                5155                5160

Ala Gly Thr Cys Gly Cys Gly Ala Gly Ala Ala Thr  Cys Cys Thr
    5165                5170                5175

Thr Ala Ala Ala Cys Cys Ala Thr Ala Thr Ala Thr  Ala Thr
    5180                5185                5190

Ala Thr Gly Gly Ala Ala Cys Ala Ala Thr Ala Gly  Ala Ala Ala
    5195                5200                5205

Thr Thr Ala Ala Thr Thr Ala Ala Cys Ala Gly Gly  Cys Cys Cys
    5210                5215                5220

Cys Thr Thr Thr Cys Cys Thr Thr Gly Thr Cys Gly  Ala
    5225                5230                5235

Thr Ala Thr Cys Ala Thr Gly Thr Ala Ala Thr Thr  Ala Gly Thr
    5240                5245                5250
```

```
Thr Ala Thr Gly Thr Cys Ala Cys Gly Cys Thr Thr Ala Cys Ala
    5255                5260                5265

Thr Thr Cys Ala Cys Gly Cys Cys Cys Thr Cys Cys Thr Cys Cys
    5270                5275                5280

Cys Ala Cys Ala Thr Cys Cys Gly Cys Thr Cys Thr Ala Ala Cys
    5285                5290                5295

Cys Gly Ala Ala Ala Ala Gly Gly Ala Ala Gly Gly Ala Gly Thr
    5300                5305                5310

Thr Ala Gly Ala Cys Ala Ala Cys Cys Thr Gly Ala Ala Gly Thr
    5315                5320                5325

Cys Thr Ala Gly Gly Thr Cys Cys Cys Thr Ala Thr Thr Thr Ala
    5330                5335                5340

Thr Thr Thr Thr Thr Thr Thr Thr Ala Ala Thr Ala Gly Thr Thr
    5345                5350                5355

Ala Thr Gly Thr Thr Ala Gly Thr Ala Thr Thr Ala Ala Gly Ala
    5360                5365                5370

Ala Cys Gly Thr Thr Ala Thr Thr Thr Ala Thr Ala Thr Thr Thr
    5375                5380                5385

Cys Ala Ala Ala Thr Thr Thr Thr Cys Thr Thr Thr Thr Thr Thr
    5390                5395                5400

Thr Thr Thr Cys Thr Gly Thr Ala Cys Ala Ala Ala Cys Gly Cys
    5405                5410                5415

Gly Thr Gly Thr Ala Cys Gly Cys Ala Thr Gly Thr Ala Ala Cys
    5420                5425                5430

Ala Thr Thr Ala Thr Ala Cys Thr Gly Ala Ala Ala Ala Cys Cys
    5435                5440                5445

Thr Thr Gly Cys Thr Thr Gly Ala Gly Ala Ala Gly Gly Thr Thr
    5450                5455                5460

Thr Thr Gly Gly Gly Ala Cys Gly Cys Thr Cys Gly Ala Ala Gly
    5465                5470                5475

Gly Cys Thr Thr Thr Ala Ala Thr Thr Thr Gly Cys Ala Ala Gly
    5480                5485                5490

Cys Thr Gly Cys Gly Gly Cys Thr Ala Ala Gly Gly Cys Gly Gly
    5495                5500                5505

Cys Gly Cys Cys Ala Gly Gly Cys Cys Ala Thr Ala Ala Thr Gly
    5510                5515                5520

Gly Cys Cys Cys Ala Ala Ala Thr Gly Cys Ala Ala Gly Ala Gly
    5525                5530                5535

Gly Ala Cys Ala Thr Thr Ala Gly Ala Ala Ala Thr Gly Thr Gly
    5540                5545                5550

Thr Thr Thr Gly Gly Thr Ala Ala Gly Ala Ala Cys Ala Thr Gly
    5555                5560                5565

Ala Ala Gly Cys Cys Gly Gly Ala Gly Gly Cys Ala Thr Ala Cys
    5570                5575                5580

Ala Ala Ala Cys Gly Ala Thr Thr Cys Ala Cys Ala Gly Ala Thr
    5585                5590                5595

Thr Thr Gly Ala Ala Gly Gly Ala Gly Gly Ala Ala Ala Ala Cys
    5600                5605                5610

Ala Ala Ala Cys Thr Gly Cys Ala Thr Cys Cys Ala Cys Cys Gly
    5615                5620                5625

Gly Ala Ala Gly Thr Gly Cys Ala Gly Cys Ala Gly Cys Cys
    5630                5635                5640

Gly Thr Gly Thr Ala Thr Gly Cys Cys Ala Ala Cys Cys Thr Thr
```

-continued

```
            5645                5650                5655

Gly Cys Thr Cys Thr Cys Ala Ala Gly Gly Cys Ala Thr Thr
        5660                5665                5670

Cys Cys Thr Ala Cys Gly Gly Ala Thr Cys Thr Gly Ala Gly Thr
        5675                5680                5685

Gly Gly Gly Ala Ala Ala Thr Ala Thr Cys Thr Gly Ala Gly Ala
        5690                5695                5700

Thr Thr Cys Ala Cys Ala Gly Ala Cys Cys Ala Cys Thr Ala
        5705                5710                5715

Thr Thr Gly Gly Ala Ala Cys Ala Gly Thr Ala Cys Cys Ala Ala
        5720                5725                5730

Ala Cys Cys Thr Ala Gly Thr Thr Thr Gly Gly Cys Cys Gly Ala
        5735                5740                5745

Thr Cys Cys Ala Thr Gly Ala Thr Thr Ala Thr Gly Thr Ala Ala
        5750                5755                5760

Thr Gly Cys Ala Thr Ala Thr Ala Gly Thr Thr Thr Thr Gly
        5765                5770                5775

Thr Cys Gly Ala Thr Gly Cys Thr Cys Ala Cys Cys Cys Gly Thr
        5780                5785                5790

Thr Thr Cys Gly Ala Gly Thr Cys Thr Gly Thr Cys Thr Cys Gly
        5795                5800                5805

Thr Ala Thr Cys Gly Thr Cys Thr Thr Ala Cys Gly Thr Ala Thr
        5810                5815                5820

Ala Ala Gly Thr Thr Cys Ala Ala Gly Cys Ala Thr Gly Thr Thr
        5825                5830                5835

Thr Ala Cys Cys Ala Gly Gly Thr Cys Thr Gly Thr Thr Ala Gly
        5840                5845                5850

Ala Ala Ala Cys Thr Cys Cys Thr Thr Thr Gly Thr Gly Ala Gly
        5855                5860                5865

Gly Gly Cys Ala Gly Gly Ala Cys Cys Thr Ala Thr Cys Gly
        5870                5875                5880

Thr Cys Thr Cys Gly Gly Thr Cys Cys Cys Gly Thr Thr Gly Thr
        5885                5890                5895

Thr Thr Cys Thr Ala Ala Gly Ala Gly Ala Cys Thr Gly Thr Ala
        5900                5905                5910

Cys Ala Gly Cys Cys Ala Ala Gly Cys Gly Cys Ala Gly Ala Ala
        5915                5920                5925

Thr Gly Gly Thr Gly Gly Cys Ala Thr Thr Ala Ala Cys Cys Ala
        5930                5935                5940

Thr Ala Ala Gly Ala Gly Gly Ala Thr Thr Cys Thr Gly Ala Thr
        5945                5950                5955

Cys Gly Gly Ala Cys Thr Thr Gly Gly Thr Cys Thr Ala Thr Thr
        5960                5965                5970

Gly Gly Cys Thr Ala Thr Thr Gly Gly Ala Ala Cys Cys Ala Cys
        5975                5980                5985

Cys Cys Thr Thr Thr Ala Cys Gly Gly Gly Ala Cys Ala Ala Cys
        5990                5995                6000

Cys Ala Ala Cys Cys Cys Thr Ala Cys Cys Ala Ala Gly Ala Cys
        6005                6010                6015

Thr Cys Cys Thr Ala Thr Thr Gly Cys Ala Thr Thr Thr Gly Thr
        6020                6025                6030

Gly Gly Ala Ala Cys Cys Ala Gly Cys Cys Ala Cys Gly Gly Ala
        6035                6040                6045
```

```
Ala Ala Gly Ala Gly Cys Gly Thr Thr Ala Gly Gly Ala
    6050            6055            6060

Cys Gly Gly Ala Gly Ala Cys Gly Thr Cys Thr Cys Thr Gly Thr
    6065            6070            6075

Gly Ala Thr Thr Thr Thr Thr Gly Thr Thr Cys Thr Cys Gly Gly
    6080            6085            6090

Ala Gly Gly Thr Cys Cys Ala Gly Gly Ala Gly Cys Thr Gly Gly
    6095            6100            6105

Ala Ala Ala Ala Gly Gly Thr Ala Cys Cys Ala Ala Thr Gly
    6110            6115            6120

Thr Gly Cys Cys Ala Ala Ala Cys Thr Ala Gly Thr Gly Ala Gly
    6125            6130            6135

Thr Ala Ala Thr Thr Ala Cys Gly Gly Ala Thr Thr Gly Thr
    6140            6145            6150

Thr Cys Ala Cys Cys Thr Gly Thr Cys Ala Gly Cys Thr Gly Gly
    6155            6160            6165

Ala Gly Ala Cys Thr Thr Gly Thr Thr Ala Cys Gly Thr Gly Cys
    6170            6175            6180

Ala Gly Ala Ala Cys Ala Gly Ala Ala Gly Ala Gly Gly Gly Ala
    6185            6190            6195

Gly Gly Gly Gly Thr Cys Thr Ala Ala Gly Thr Ala Thr Gly Gly
    6200            6205            6210

Ala Gly Ala Gly Ala Thr Gly Ala Thr Thr Cys Cys Cys Ala
    6215            6220            6225

Gly Thr Ala Thr Ala Thr Cys Ala Gly Ala Gly Ala Thr Gly Gly
    6230            6235            6240

Ala Cys Thr Gly Ala Thr Ala Gly Thr Ala Cys Cys Thr Cys Ala
    6245            6250            6255

Ala Gly Ala Gly Gly Thr Cys Ala Cys Cys Ala Thr Thr Gly Cys
    6260            6265            6270

Gly Cys Thr Cys Thr Thr Gly Gly Ala Gly Cys Ala Gly Gly Cys
    6275            6280            6285

Cys Ala Thr Gly Ala Ala Gly Gly Ala Ala Ala Ala Cys Thr Thr
    6290            6295            6300

Cys Gly Ala Gly Ala Ala Ala Gly Gly Gly Ala Ala Gly Ala Cys
    6305            6310            6315

Ala Cys Gly Gly Thr Thr Cys Thr Thr Gly Ala Thr Thr Gly Ala
    6320            6325            6330

Thr Gly Gly Ala Thr Thr Cys Cys Cys Thr Cys Gly Thr Ala Ala
    6335            6340            6345

Gly Ala Thr Gly Gly Ala Cys Cys Ala Gly Gly Cys Cys Ala Ala
    6350            6355            6360

Ala Ala Cys Thr Thr Thr Thr Gly Ala Gly Gly Ala Ala Ala Ala
    6365            6370            6375

Ala Gly Thr Cys Gly Cys Ala Ala Ala Gly Thr Cys Cys Ala Ala
    6380            6385            6390

Gly Gly Thr Gly Ala Cys Ala Cys Thr Thr Thr Cys Thr Thr
    6395            6400            6405

Thr Gly Ala Thr Thr Gly Thr Cys Cys Cys Gly Ala Ala Thr Cys
    6410            6415            6420

Ala Gly Thr Gly Cys Thr Cys Cys Thr Thr Gly Ala Gly Ala Gly
    6425            6430            6435
```

-continued

```
Ala Thr Thr Ala Cys Thr Thr Ala Ala Ala Ala Gly Ala Gly Gly
    6440            6445                6450

Ala Cys Ala Gly Ala Cys Ala Ala Gly Cys Gly Gly Ala Ala Gly
    6455            6460                6465

Ala Gly Ala Gly Gly Ala Thr Gly Ala Thr Ala Ala Thr Gly Cys
    6470            6475                6480

Gly Gly Ala Gly Ala Gly Thr Ala Thr Cys Ala Ala Ala Ala Ala
    6485            6490                6495

Ala Ala Gly Ala Thr Thr Cys Ala Ala Ala Cys Ala Thr Thr
    6500            6505                6510

Cys Gly Thr Gly Gly Ala Ala Ala Cys Thr Thr Cys Gly Ala Thr
    6515            6520                6525

Gly Cys Cys Thr Gly Thr Gly Gly Thr Gly Gly Ala Cys Thr Ala
    6530            6535                6540

Thr Thr Thr Cys Gly Gly Gly Ala Ala Gly Cys Ala Ala Gly Gly
    6545            6550                6555

Ala Cys Gly Cys Gly Thr Thr Thr Thr Gly Ala Ala Gly Gly Thr
    6560            6565                6570

Ala Thr Cys Thr Thr Gly Thr Gly Ala Cys Cys Ala Cys Cys Cys
    6575            6580                6585

Thr Gly Thr Gly Gly Ala Thr Cys Ala Ala Gly Thr Gly Thr Ala
    6590            6595                6600

Thr Thr Cys Ala Cys Ala Gly Gly Thr Ala Thr Gly Thr Thr Cys
    6605            6610                6615

Gly Gly Thr Gly Cys Thr Ala Ala Ala Ala Gly Ala Gly Ala Ala
    6620            6625                6630

Gly Gly Gly Gly Ala Thr Cys Thr Thr Thr Gly Cys Cys Gly Ala
    6635            6640                6645

Thr Ala Ala Cys Gly Ala Gly Ala Cys Gly Gly Ala Gly Ala Ala
    6650            6655                6660

Thr Ala Ala Ala Thr Ala Ala Ala Cys Ala Thr Thr Gly Thr Ala
    6665            6670                6675

Ala Thr Ala Ala Gly Ala Thr Thr Thr Ala Gly Ala Cys Thr Gly
    6680            6685                6690

Thr Gly Ala Ala Thr Gly Thr Cys Thr Ala Thr Gly Thr Ala
    6695            6700                6705

Ala Thr Ala Thr Thr Thr Thr Cys Gly Ala Gly Ala Thr Ala
    6710            6715                6720

Cys Thr Gly Thr Ala Thr Cys Thr Ala Thr Cys Thr Gly Gly Thr
    6725            6730                6735

Gly Thr Ala Cys Cys Gly Thr Ala Thr Cys Ala Cys Thr Cys Thr
    6740            6745                6750

Gly Gly Ala Cys Thr Thr Gly Cys Ala Ala Ala Cys Thr Cys Ala
    6755            6760                6765

Thr Thr Gly Ala Thr Thr Ala Cys Thr Thr Gly Thr Gly Cys Ala
    6770            6775                6780

Ala Thr Gly Gly Gly Cys Ala Gly Ala Ala Gly Gly Ala Thr
    6785            6790                6795

Ala Gly Cys Thr Cys Thr Ala Gly Ala Ala Ala Gly Ala Ala Gly
    6800            6805                6810

Ala Ala Gly Ala Ala Ala Ala Ala Gly Gly Ala Gly Cys Cys Gly
    6815            6820                6825

Cys Cys Thr Gly Ala Ala Gly Ala Gly Cys Thr Gly Gly Ala Thr
```

-continued

```
                6830                6835                6840

Cys Thr Thr Thr Cys Cys Gly Ala Gly Gly Thr Thr Gly Thr Thr
            6845                6850                6855

Cys Cys Ala Ala Cys Thr Thr Thr Thr Gly Gly Thr Thr Ala Thr
            6860                6865                6870

Gly Ala Gly Gly Ala Ala Thr Thr Thr Cys Ala Thr Gly Thr Thr
            6875                6880                6885

Gly Ala Gly Cys Ala Ala Gly Ala Gly Gly Ala Gly Ala Ala Thr
            6890                6895                6900

Cys Cys Gly Gly Thr Cys Gly Ala Thr Cys Ala Ala Gly Ala Cys
            6905                6910                6915

Gly Ala Ala Cys Thr Thr Gly Ala Cys Gly Gly Cys Cys Ala Thr
            6920                6925                6930

Ala Ala Thr Gly Gly Cys Cys Thr Ala Gly Cys Thr Thr Gly Gly
            6935                6940                6945

Cys Gly Thr Ala Ala Thr Cys Ala Thr Gly Gly Thr Cys Ala Thr
            6950                6955                6960

Ala Gly Cys Thr Gly Thr Thr Thr Cys Cys Thr Gly Thr Gly Thr
            6965                6970                6975

Gly Ala Ala Ala Thr Thr Gly Thr Thr Ala Thr Cys Cys Gly Cys
            6980                6985                6990

Thr Cys Ala Cys Ala Ala Thr Thr Cys Cys Ala Cys Ala Cys Ala
            6995                7000                7005

Ala Cys Ala Thr Ala Cys Gly Ala Gly Cys Cys Gly Gly Ala Ala
            7010                7015                7020

Gly Cys Ala Thr Ala Ala Ala Gly Thr Gly Thr Ala Ala Ala Gly
            7025                7030                7035

Cys Cys Thr Gly Gly Gly Gly Thr Gly Cys Cys Thr Ala Ala Thr
            7040                7045                7050

Gly Ala Gly Thr Gly Ala Gly Cys Thr Ala Ala Cys Thr Cys Ala
            7055                7060                7065

Cys Ala Thr Thr Ala Ala Thr Thr Gly Cys Gly Thr Thr Gly Cys
            7070                7075                7080

Gly Cys Thr Cys Ala Cys Thr Gly Cys Cys Cys Gly Cys Thr Thr
            7085                7090                7095

Thr Cys Cys Ala Gly Thr Cys Gly Gly Gly Ala Ala Ala Cys Cys
            7100                7105                7110

Thr Gly Thr Cys Gly Thr Gly Cys Cys Ala Gly Cys Thr Gly Cys
            7115                7120                7125

Ala Thr Thr Ala Ala Thr Gly Ala Ala Thr Cys Gly Gly Cys Cys
            7130                7135                7140

Ala Ala Cys Gly Cys Gly Cys Gly Gly Gly Gly Ala Gly Ala Gly
            7145                7150                7155

Gly Cys Gly Gly Thr Thr Thr Gly Cys Gly Thr Ala Thr Thr Gly
            7160                7165                7170

Gly Gly Cys Gly Cys Thr Cys Thr Thr Cys Cys Gly Cys Thr Thr
            7175                7180                7185

Cys Cys Thr Cys Gly Cys Thr Cys Ala Cys Thr Gly Ala Cys Thr
            7190                7195                7200

Cys Gly Cys Thr Gly Cys Gly Cys Thr Cys Gly Gly Thr Cys Gly
            7205                7210                7215

Thr Thr Cys Gly Gly Cys Thr Gly Cys Gly Gly Cys Gly Ala Gly
            7220                7225                7230
```

```
Cys Gly Gly Thr Ala Thr Cys Ala Gly Cys Thr Cys Ala Cys Thr
    7235             7240                7245

Cys Ala Ala Ala Gly Gly Cys Gly Gly Thr Ala Ala Thr Ala Cys
    7250             7255                7260

Gly Gly Thr Thr Ala Thr Cys Cys Ala Cys Ala Gly Ala Ala Thr
    7265             7270                7275

Cys Ala Gly Gly Gly Gly Ala Thr Ala Ala Cys Gly Cys Ala Gly
    7280             7285                7290

Gly Ala Ala Ala Gly Ala Ala Cys Ala Thr Gly Thr Gly Ala Gly
    7295             7300                7305

Cys Ala Ala Ala Ala Gly Gly Cys Cys Ala Gly Cys Ala Ala Ala
    7310             7315                7320

Ala Gly Gly Cys Cys Ala Gly Gly Ala Ala Cys Cys Gly Thr Ala
    7325             7330                7335

Ala Ala Ala Ala Gly Gly Cys Cys Gly Cys Gly Thr Thr Gly Cys
    7340             7345                7350

Thr Gly Gly Cys Gly Thr Thr Thr Thr Thr Cys Cys Ala Thr Ala
    7355             7360                7365

Gly Gly Cys Thr Cys Cys Gly Cys Cys Cys Cys Cys Cys Thr Gly
    7370             7375                7380

Ala Cys Gly Ala Gly Cys Ala Thr Cys Ala Cys Ala Ala Ala Ala
    7385             7390                7395

Ala Thr Cys Gly Ala Cys Gly Cys Thr Cys Ala Ala Gly Thr Cys
    7400             7405                7410

Ala Gly Ala Gly Gly Thr Gly Gly Cys Gly Ala Ala Ala Cys Cys
    7415             7420                7425

Cys Gly Ala Cys Ala Gly Gly Ala Cys Thr Ala Thr Ala Ala Ala
    7430             7435                7440

Gly Ala Thr Ala Cys Cys Ala Gly Gly Cys Gly Thr Thr Thr Cys
    7445             7450                7455

Cys Cys Cys Cys Thr Gly Gly Ala Ala Gly Cys Thr Cys Cys Cys
    7460             7465                7470

Thr Cys Gly Thr Gly Cys Gly Cys Thr Cys Thr Cys Cys Thr Gly
    7475             7480                7485

Thr Thr Cys Cys Gly Ala Cys Cys Cys Thr Gly Cys Cys Gly Cys
    7490             7495                7500

Thr Thr Ala Cys Cys Gly Gly Ala Thr Ala Cys Cys Thr Gly Thr
    7505             7510                7515

Cys Cys Gly Cys Cys Thr Thr Thr Cys Thr Cys Cys Cys Thr Thr
    7520             7525                7530

Cys Gly Gly Gly Ala Ala Gly Cys Gly Thr Gly Gly Cys Gly Cys
    7535             7540                7545

Thr Thr Thr Cys Thr Cys Ala Thr Ala Gly Cys Thr Cys Ala Cys
    7550             7555                7560

Gly Cys Thr Gly Thr Ala Gly Gly Thr Ala Thr Cys Thr Cys Ala
    7565             7570                7575

Gly Thr Thr Cys Gly Gly Thr Gly Thr Ala Gly Gly Thr Cys Gly
    7580             7585                7590

Thr Thr Cys Gly Cys Thr Cys Cys Ala Ala Gly Cys Thr Gly Gly
    7595             7600                7605

Gly Cys Thr Gly Thr Gly Thr Gly Cys Ala Cys Gly Ala Ala Cys
    7610             7615                7620
```

-continued

```
Cys Cys  Cys Cys Cys Gly Thr  Thr Cys Ala Gly Cys  Cys Cys Gly
    7625                 7630                 7635

Ala Cys  Cys Gly Cys Thr Gly  Cys Gly Cys Cys Thr  Thr Ala Thr
    7640                 7645                 7650

Cys Cys  Gly Gly Thr Ala Ala  Cys Thr Ala Thr Cys  Gly Thr Cys
    7655                 7660                 7665

Thr Thr  Gly Ala Gly Thr Cys  Cys Ala Ala Cys Cys  Cys Gly Gly
    7670                 7675                 7680

Thr Ala  Ala Gly Ala Cys Ala  Cys Gly Ala Cys Thr  Thr Ala Thr
    7685                 7690                 7695

Cys Gly  Cys Cys Ala Cys Thr  Gly Gly Cys Ala Gly  Cys Ala Gly
    7700                 7705                 7710

Cys Cys  Ala Cys Thr Gly Gly  Thr Ala Ala Cys Ala  Gly Gly Ala
    7715                 7720                 7725

Thr Thr  Ala Gly Cys Ala Gly  Ala Gly Cys Gly Ala  Gly Gly Thr
    7730                 7735                 7740

Ala Thr  Gly Thr Ala Gly Gly  Cys Gly Gly Thr Gly  Cys Thr Ala
    7745                 7750                 7755

Cys Ala  Gly Ala Gly Thr Thr  Cys Thr Thr Gly Ala  Ala Gly Thr
    7760                 7765                 7770

Gly Gly  Thr Gly Gly Cys Cys  Thr Ala Ala Cys Thr  Ala Cys Gly
    7775                 7780                 7785

Gly Cys  Thr Ala Cys Ala Cys  Thr Ala Gly Ala Ala  Gly Gly Ala
    7790                 7795                 7800

Cys Ala  Gly Thr Ala Thr Thr  Thr Gly Gly Thr Ala  Thr Cys Thr
    7805                 7810                 7815

Gly Cys  Gly Cys Thr Cys Thr  Gly Cys Thr Gly Ala  Ala Gly Cys
    7820                 7825                 7830

Cys Ala  Gly Thr Thr Ala Cys  Cys Thr Thr Cys Gly  Gly Ala Ala
    7835                 7840                 7845

Ala Ala  Ala Gly Ala Gly Thr  Thr Gly Gly Thr Ala  Gly Cys Thr
    7850                 7855                 7860

Cys Thr  Thr Gly Ala Thr Cys  Cys Gly Gly Cys Ala  Ala Ala Cys
    7865                 7870                 7875

Ala Ala  Ala Cys Cys Ala Cys  Cys Gly Cys Thr Gly  Gly Thr Ala
    7880                 7885                 7890

Gly Cys  Gly Gly Thr Gly Gly  Thr Thr Thr Thr Thr  Thr Thr Gly
    7895                 7900                 7905

Thr Thr  Thr Gly Cys Ala Ala  Gly Cys Ala Gly Cys  Ala Gly Ala
    7910                 7915                 7920

Thr Thr  Ala Cys Gly Cys Gly  Cys Ala Gly Ala Ala  Ala Ala Ala
    7925                 7930                 7935

Ala Ala  Gly Gly Ala Thr Cys  Thr Cys Ala Ala Gly  Ala Ala Gly
    7940                 7945                 7950

Ala Thr  Cys Cys Thr Thr Thr  Gly Ala Thr Cys Thr  Thr Thr Thr
    7955                 7960                 7965

Cys Thr  Ala Cys Gly Gly Gly  Gly Thr Cys Thr Gly  Ala Cys Gly
    7970                 7975                 7980

Cys Thr  Cys Ala Gly Thr Gly  Gly Ala Ala Cys Gly  Ala Ala Ala
    7985                 7990                 7995

Ala Cys  Thr Cys Ala Cys Gly  Thr Thr Ala Ala Gly  Gly Gly Ala
    8000                 8005                 8010

Thr Thr  Thr Thr Gly Gly Thr  Cys Ala Thr Gly Ala  Gly Ala Thr
```

-continued

```
                8015                8020                8025

Thr Ala Thr Cys Ala Ala Ala Ala Gly Gly Ala Thr Cys Thr
    8030                8035                8040

Thr Cys Ala Cys Cys Thr Ala Gly Ala Thr Cys Cys Thr Thr Thr
    8045                8050                8055

Thr Ala Ala Ala Thr Thr Ala Ala Ala Ala Thr Gly Ala Ala
    8060                8065                8070

Gly Thr Thr Thr Thr Ala Ala Ala Thr Cys Ala Ala Thr Cys Thr
    8075                8080                8085

Ala Ala Ala Gly Thr Ala Thr Ala Thr Ala Thr Gly Ala Gly Thr
    8090                8095                8100

Ala Ala Ala Cys Thr Thr Gly Gly Thr Cys Thr Gly Ala Cys Ala
    8105                8110                8115

Gly Thr Thr Ala Cys Cys Ala Ala Thr Gly Cys Thr Thr Ala Ala
    8120                8125                8130

Thr Cys Ala Gly Thr Gly Ala Gly Gly Cys Ala Cys Cys Thr Ala
    8135                8140                8145

Thr Cys Thr Cys Ala Gly Cys Gly Ala Thr Cys Thr Gly Thr Cys
    8150                8155                8160

Thr Ala Thr Thr Thr Cys Gly Thr Thr Cys Ala Thr Cys Cys Ala
    8165                8170                8175

Thr Ala Gly Thr Thr Gly Cys Cys Thr Gly Ala Cys Thr Cys Cys
    8180                8185                8190

Cys Cys Gly Thr Cys Gly Thr Gly Thr Ala Gly Ala Thr Ala Ala
    8195                8200                8205

Cys Thr Ala Cys Gly Ala Thr Ala Cys Gly Gly Gly Ala Gly Gly
    8210                8215                8220

Gly Cys Thr Thr Ala Cys Cys Ala Thr Cys Thr Gly Gly Cys Cys
    8225                8230                8235

Cys Cys Ala Gly Thr Gly Cys Thr Gly Cys Ala Ala Thr Gly Ala
    8240                8245                8250

Thr Ala Cys Cys Gly Cys Gly Ala Gly Ala Cys Cys Cys Ala Cys
    8255                8260                8265

Gly Cys Thr Cys Ala Cys Cys Gly Gly Cys Thr Cys Cys Ala Gly
    8270                8275                8280

Ala Thr Thr Thr Ala Thr Cys Ala Gly Cys Ala Ala Thr Ala Ala
    8285                8290                8295

Ala Cys Cys Ala Gly Cys Cys Ala Gly Cys Cys Gly Gly Ala Ala
    8300                8305                8310

Gly Gly Gly Cys Cys Gly Ala Gly Cys Gly Cys Ala Gly Ala Ala
    8315                8320                8325

Gly Thr Gly Gly Thr Cys Cys Thr Gly Cys Ala Ala Cys Thr Thr
    8330                8335                8340

Thr Ala Thr Cys Cys Gly Cys Cys Thr Cys Cys Ala Thr Cys Cys
    8345                8350                8355

Ala Gly Thr Cys Thr Ala Thr Thr Ala Ala Thr Thr Gly Thr Thr
    8360                8365                8370

Gly Cys Cys Gly Gly Gly Ala Ala Gly Cys Thr Ala Gly Ala Gly
    8375                8380                8385

Thr Ala Ala Gly Thr Ala Gly Thr Thr Cys Gly Cys Cys Ala Gly
    8390                8395                8400

Thr Thr Ala Ala Thr Ala Gly Thr Thr Thr Gly Cys Gly Cys Ala
    8405                8410                8415
```

```
Ala Cys Gly Thr Thr Gly Thr Thr Gly Cys Cys Ala Thr Thr Gly
8420                 8425                 8430

Cys Thr Ala Cys Ala Gly Gly Cys Ala Thr Cys Gly Thr Gly Gly
8435                 8440                 8445

Thr Gly Thr Cys Ala Cys Gly Cys Thr Cys Gly Thr Cys Gly Thr
8450                 8455                 8460

Thr Thr Gly Gly Thr Ala Thr Gly Gly Cys Thr Thr Cys Ala Thr
8465                 8470                 8475

Thr Cys Ala Gly Cys Thr Cys Cys Gly Gly Thr Thr Cys Cys Cys
8480                 8485                 8490

Ala Ala Cys Gly Ala Thr Cys Ala Ala Gly Gly Cys Gly Ala Gly
8495                 8500                 8505

Thr Thr Ala Cys Ala Thr Gly Ala Thr Cys Cys Cys Cys Cys Ala
8510                 8515                 8520

Thr Gly Thr Thr Gly Thr Gly Cys Ala Ala Ala Ala Ala Ala Gly
8525                 8530                 8535

Cys Gly Gly Thr Thr Ala Gly Cys Thr Cys Cys Thr Thr Cys Gly
8540                 8545                 8550

Gly Thr Cys Cys Thr Cys Cys Gly Ala Thr Cys Gly Thr Thr Gly
8555                 8560                 8565

Thr Cys Ala Gly Ala Ala Gly Thr Ala Ala Gly Thr Thr Gly Gly
8570                 8575                 8580

Cys Cys Gly Cys Ala Gly Thr Gly Thr Thr Ala Thr Cys Ala Cys
8585                 8590                 8595

Thr Cys Ala Thr Gly Gly Thr Thr Ala Thr Gly Gly Cys Ala Gly
8600                 8605                 8610

Cys Ala Cys Thr Gly Cys Ala Thr Ala Ala Thr Thr Cys Thr Cys
8615                 8620                 8625

Thr Thr Ala Cys Thr Gly Thr Cys Ala Thr Gly Cys Cys Ala Thr
8630                 8635                 8640

Cys Cys Gly Thr Ala Ala Gly Ala Thr Gly Cys Thr Thr Thr Thr
8645                 8650                 8655

Cys Thr Gly Thr Gly Ala Cys Thr Gly Gly Thr Gly Ala Gly Thr
8660                 8665                 8670

Ala Cys Thr Cys Ala Ala Cys Cys Ala Ala Gly Thr Cys Ala Thr
8675                 8680                 8685

Thr Cys Thr Gly Ala Gly Ala Ala Thr Ala Gly Thr Gly Thr Ala
8690                 8695                 8700

Thr Gly Cys Gly Gly Cys Gly Ala Cys Cys Gly Ala Gly Thr Thr
8705                 8710                 8715

Gly Cys Thr Cys Thr Thr Gly Cys Cys Cys Gly Gly Cys Gly Thr
8720                 8725                 8730

Cys Ala Ala Thr Ala Cys Gly Gly Gly Ala Thr Ala Ala Thr Ala
8735                 8740                 8745

Cys Cys Gly Cys Gly Cys Cys Ala Cys Ala Thr Ala Gly Cys Ala
8750                 8755                 8760

Gly Ala Ala Cys Thr Thr Thr Ala Ala Ala Ala Gly Thr Gly Cys
8765                 8770                 8775

Thr Cys Ala Thr Cys Ala Thr Thr Gly Gly Ala Ala Ala Ala Cys
8780                 8785                 8790
```

```
Gly Thr Thr Cys Thr Thr Cys Gly Gly Gly Cys Gly Ala Ala
    8795            8800            8805

Ala Ala Cys Thr Cys Thr Cys Ala Ala Gly Gly Ala Thr Cys Thr
    8810            8815            8820

Thr Ala Cys Cys Gly Cys Thr Gly Thr Thr Gly Ala Gly Ala Thr
    8825            8830            8835

Cys Cys Ala Gly Thr Thr Cys Gly Ala Thr Gly Thr Ala Ala Cys
    8840            8845            8850

Cys Cys Ala Cys Thr Cys Gly Thr Gly Cys Ala Cys Cys Cys Ala
    8855            8860            8865

Ala Cys Thr Gly Ala Thr Cys Thr Thr Cys Ala Gly Cys Ala Thr
    8870            8875            8880

Cys Thr Thr Thr Thr Ala Cys Thr Thr Thr Cys Ala Cys Cys Ala
    8885            8890            8895

Gly Cys Gly Thr Thr Thr Cys Thr Gly Gly Gly Thr Gly Ala Gly
    8900            8905            8910

Cys Ala Ala Ala Ala Ala Cys Ala Gly Gly Ala Ala Gly Gly Cys
    8915            8920            8925

Ala Ala Ala Ala Thr Gly Cys Cys Gly Cys Ala Ala Ala Ala Ala
    8930            8935            8940

Ala Gly Gly Gly Ala Ala Thr Ala Ala Gly Gly Gly Cys Gly Ala
    8945            8950            8955

Cys Ala Cys Gly Gly Ala Ala Ala Thr Gly Thr Thr Gly Ala Ala
    8960            8965            8970

Thr Ala Cys Thr Cys Ala Thr Ala Cys Thr Cys Thr Thr Cys Cys
    8975            8980            8985

Thr Thr Thr Thr Thr Cys Ala Ala Thr Ala Thr Thr Ala Thr Thr
    8990            8995            9000

Gly Ala Ala Gly Cys Ala Thr Thr Thr Ala Thr Cys Ala Gly Gly
    9005            9010            9015

Gly Thr Thr Ala Thr Thr Gly Thr Cys Thr Cys Ala Thr Gly Ala
    9020            9025            9030

Gly Cys Gly Gly Ala Thr Ala Cys Ala Thr Ala Thr Thr Thr Gly
    9035            9040            9045

Ala Ala Thr Gly Thr Ala Thr Thr Thr Ala Gly Ala Ala Ala Ala
    9050            9055            9060

Ala Thr Ala Ala Ala Cys Ala Ala Ala Thr Ala Gly Gly Gly Gly
    9065            9070            9075

Thr Thr Cys Cys Gly Cys Gly Cys Ala Cys Ala Thr Thr Thr Cys
    9080            9085            9090

Cys Cys Cys Gly Ala Ala Ala Ala Gly Thr Gly Cys Cys Ala Cys
    9095            9100            9105

Cys Thr Gly Ala Cys Gly Thr Cys Thr Ala Ala Gly Ala Ala Ala
    9110            9115            9120

Cys Cys Ala Thr Thr Ala Thr Thr Ala Thr Cys Ala Thr Gly Ala
    9125            9130            9135

Cys Ala Thr Thr Ala Ala Cys Cys Thr Ala Thr Ala Ala Ala Ala
    9140            9145            9150

Ala Thr Ala Gly Gly Cys Gly Thr Ala Thr Cys Ala Cys Gly Ala
    9155            9160            9165

Gly Gly Cys Cys Cys Thr Thr Thr Cys Gly Thr Cys
    9170            9175            9180
```